(12) United States Patent
Anderson et al.

(10) Patent No.: US 10,487,080 B2
(45) Date of Patent: Nov. 26, 2019

(54) NAPHTHYRIDINES AS INTEGRIN ANTAGONISTS

(71) Applicant: GlaxoSmithKline Intellectual Property Development Limited, Brentford, Middlesex (GB)

(72) Inventors: Niall Andrew Anderson, Stevenage (GB); Matthew Howard James Campbell-Crawford, Stevenage (GB); Ashley Paul Hancock, Stevenage (GB); Seble Lemma, Stevenage (GB); John Martin Pritchard, Stevenage (GB); Panayiotis Alexandrou Procopiou, Stevenage (GB); Steven Leslie Sollis, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/087,320

(22) PCT Filed: Mar. 20, 2017

(86) PCT No.: PCT/EP2017/056525
§ 371 (c)(1),
(2) Date: Sep. 21, 2018

(87) PCT Pub. No.: WO2017/162570
PCT Pub. Date: Sep. 28, 2017

(65) Prior Publication Data
US 2019/0112306 A1    Apr. 18, 2019

(30) Foreign Application Priority Data
Mar. 21, 2016  (GB) .................................. 1604680.7

(51) Int. Cl.
C07D 471/04    (2006.01)
A61K 31/4375    (2006.01)
A61P 11/00    (2006.01)

(52) U.S. Cl.
CPC ............ *C07D 471/04* (2013.01); *A61P 11/00* (2018.01)

(58) Field of Classification Search
CPC .......................... C07D 471/04; A61K 31/4375
USPC .......................................... 514/300; 546/122
See application file for complete search history.

(56) References Cited

U.S. PATENT DOCUMENTS

2004/0092454 A1    5/2004 Schadt et al.

FOREIGN PATENT DOCUMENTS

| WO | WO 99/30709 A1 | 6/1999 |
|---|---|---|
| WO | WO 99/31061 A1 | 6/1999 |
| WO | WO 00/72801 A2 | 12/2000 |
| WO | WO 00/78317 A1 | 12/2000 |
| WO | WO 01/24797 A1 | 4/2001 |
| WO | WO 01/34602 A2 | 5/2001 |
| WO | WO 01/096334 A2 | 12/2001 |
| WO | WO 02/07730 A1 | 1/2002 |
| WO | WO 02/22616 A2 | 3/2002 |
| WO | WO 02/053099 A2 | 7/2002 |
| WO | WO 03/039544 A1 | 5/2003 |
| WO | WO2004/058254 A1 | 7/2004 |
| WO | WO 2004/092454 A2 | 10/2004 |
| WO | WO 2005/082889 A1 | 9/2005 |
| WO | WO 2008/118455 A1 | 10/2008 |

(Continued)

OTHER PUBLICATIONS

Cho et al., "Pirfenidone: an anti-fibrotic and cytoprotective agent as therapy for progressive kidney disease", *Expert Opin. Investig. Drugs*, vol. 19, No. 2, pp. 275-283 (2010).
Goodman et al., "Integrins as therapeutic targets", *Trends in Pharmacological Sciences*, vol. 33, No. 7, pp. 405-412 (2012).
Hahm et al., "avB6 integrin Regulates Renal Fibrosis and Inflammation in Alport Mouse", *The American Journal of Pathology*, vol. 170, No. 1, pp. 110-125 (2007).

(Continued)

*Primary Examiner* — Niloofar Rahmani
(74) *Attorney, Agent, or Firm* — Jane F. Djung; Duke M. Fitch; Edward R. Gimmi

(57) ABSTRACT

The invention relates to compounds of Formula (I):

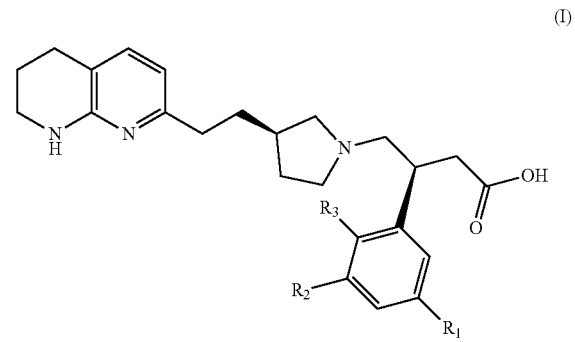

(I)

wherein $R_1$, $R_2$ and $R_3$ are as defined in the description and claims, or pharmaceutically acceptable salts thereof, having $\alpha_v\beta_6$ integrin antagonist activity. The invention also relates to pharmaceutical compositions including a compound of Formula (I), or a pharmaceutically acceptable salt thereof, and to the use of a compound of Formula (I), or a pharmaceutically acceptable salt thereof in therapy, including in the treatment of a disease or condition for which an $\alpha_v\beta_6$ integrin antagonist is indicated, in particular the treatment of idiopathic pulmonary fibrosis.

23 Claims, No Drawings

(56) References Cited

FOREIGN PATENT DOCUMENTS

| | | | |
|---|---|---|---|
| WO | WO 2009/018466 A1 | | 2/2009 |
| WO | WO 2009/055418 A1 | | 4/2009 |
| WO | WO 2011/111880 A1 | | 9/2011 |
| WO | WO 2014/154725 A1 | | 10/2014 |
| WO | WO 2015/048819 A1 | | 4/2015 |
| WO | 2016046225 | * | 3/2016 |
| WO | WO 2016/046225 A1 | | 3/2016 |
| WO | WO 2016/046226 A1 | | 3/2016 |
| WO | WO 2016/046230 A1 | | 3/2016 |
| WO | WO 2016/046241 A1 | | 3/2016 |
| WO | WO 2016/134223 A2 | | 8/2016 |
| WO | WO 2016/145258 A1 | | 9/2016 |
| WO | WO 2017/158072 A1 | | 9/2017 |
| WO | WO 2017/162570 A1 | | 9/2017 |
| WO | WO 2017/162572 A1 | | 9/2017 |

OTHER PUBLICATIONS

Horan et al., "Partial Inhibition of Integrin avB6 Prevents Pulmonary Fibrosis without Exacerbating Inflammation", *Am. J. Respir. Crit. Care Med.*, vol. 177, pp. 56-65 (2008).

Margadant, C. et al., "Integrin-Tgf-$\beta$ crosstalk in fibrosis, cancer, and wound healing", *EMBO Reports*, vol. 11, No. 2, pp. 97-105 (2010).

Popov et al, "Integrin avB6 is a marker of the progression of biliary and portal liver fibrosis and a novel target for antifibrotic therapies", *Journal of Hepatology*, vol. 48 pp. 453-464 (2008).

Trevillian et al., "$\alpha v\beta 6$ integrin expression in diseased and transplanted kidneys", *Kidney International*, vol. 66, pp. 1423-1433 (2004).

Whitman et al., "Nonpeptide $\alpha v\beta 3$ antagonists. Part 9: Improved pharmacokinetic profile through the use of an aliphatic, des-amide backbone", *Bioorganic & Medicinal Chemistry Letters*, vol. 14, No. 17, pp. 4411-4415 (2004).

Woodcock et al., "The treatment of idiopathic pulmonary fibrosis", *F1000Prime Reports*, vol. 6, No. 16, pp. 1-9 (2014).

International Search Report for International Application No. PCT/EP2014/056013, dated May 9, 2014, 4 pages.
International Search Report for International Application No. PCT/EP2015/071776, dated Nov. 23, 2015, 4 pages.
International Search Report for International Application No. PCT/EP2015/071777, dated Nov. 26, 2015, 4 pages.
International Search Report for International Application No. PCT/EP2015/071782, dated Nov. 2, 2015, 4 pages.
International Search Report for International application No. PCT/EP2015/071798, dated Nov. 10, 2015, 4 pages.
International Search Report for International application No. PCT/EP2017/056204, dated May 15, 2017, 5 pages.
International Search Report for International application No. PCT/EP2017/056525, dated May 2, 2017, 4 pages.
International Search Report for International application No. PCT/EP2017/056527, dated May 2, 2017, 5 pages.
Restriction Requirement for U.S. Appl. No. 14/778,095, USPTO, notification date Sep. 21, 2016, 9 pages.
Non-Final Office Action for U.S. Appl. No. 14/778,095, USPTO, notification date Mar. 29, 2017, 14 pages.
Notice of Allowance for U.S. Appl. No. 14/778,095, USPTO, dated Nov. 3, 2017, 11 pages.
Notice of Allowance for U.S. Appl. No. 15/514,407, USPTO, dated Nov. 6, 2017, 16 pages.
Notice of Allowance for U.S. Appl. No. 15/514,414, USPTO, dated Nov. 9, 2017, 19 pages.
Restriction Requirement for U.S. Appl. No. 15/514,416, USPTO, notification date Aug. 14, 2017, 12 pages.
Non-Final Office Action for U.S. Appl. No. 15/514,416, USPTO, notification date Nov. 2, 2017, 18 pages.
Final Office Action for U.S. Appl. No. 15/514,416, USPTO, notification date Mar. 27, 2018, 16 pages.
Notice of Allowance for U.S. Appl. No. 15/514,416, USPTO, dated Jul. 19, 2018, 11 pages.
Notice of Allowance for U.S. Appl. No. 15/514,399, USPTO, dated Dec. 15, 2017, 13 pages.
Notice of Allowance for U.S. Appl. No. 15/514,399, USPTO, dated Aug. 21, 2017, 11 pages.

* cited by examiner

NAPHTHYRIDINES AS INTEGRIN ANTAGONISTS

This application is a 371 of International Application No. PCT/EP2017/056525, filed 20 Mar. 2017, which claims the priority of GB Application No. 1604680.7, filed 21 Mar. 2016, which are incorporated herein in their entireties.

FIELD OF THE INVENTION

The present invention relates to pyrrolidine compounds being $\alpha_v\beta_6$ integrin antagonists, pharmaceutical compositions comprising such compounds and to their use in therapy, especially in the treatment of conditions for which an $\alpha_v\beta_6$ integrin antagonist is indicated, to the use of a compound in the manufacture of a medicament for the treatment of conditions in which an antagonist of $\alpha_v\beta_6$ integrin is indicated, and a method for the treatment of disorders in which antagonism of $\alpha_v\beta_6$ integrin is indicated in a human.

BACKGROUND OF THE INVENTION

Integrin superfamily proteins are heterodimeric cell surface receptors, composed of an alpha and beta subunit. At least 18 alpha and 8 beta subunits have been reported, which have been demonstrated to form 24 distinct alpha/beta heterodimers. Each chain comprises a large extracellular domain (>640 amino acids for the beta subunit, >940 amino acids for the alpha subunit), with a transmembrane spanning region of around 20 amino acids per chain, and generally a short cytoplasmic tail of 30-50 amino acids per chain. Different integrins have been shown to participate in a plethora of cellular biologies, including cell adhesion to the extracellular matrix, cell-cell interactions, and effects on cell migration, proliferation, differentiation and survival (Barczyk et al, *Cell and Tissue Research*, 2010, 339, 269).

Integrin receptors interact with binding proteins via short protein-protein binding interfaces. The integrin family can be grouped into sub-families that share similar binding recognition motifs in such ligands. A major subfamily is the RGD-integrins, which recognise ligands that contain an RGD (arginine-glycine-aspartic acid) motif within their protein sequence. There are 8 integrins in this sub-family, namely $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_5\beta_1$, $\alpha_8\beta_1$, where nomenclature demonstrates that $\alpha_v\beta_1$, $\alpha_v\beta_3$, $\alpha_v\beta_5$, $\alpha_v\beta_6$, * $\alpha_v\beta_8$ share a common $\alpha_v$ subunit with a divergent $\beta$ subunit, and $\alpha_v\beta_1$, $\alpha_5\beta_1$ & $\alpha_8\beta_1$ share a common $\beta_1$ subunit with a divergent a subunit. The $\beta_1$ subunit has been shown to pair with 11 different a subunits, of which only the 3 listed above commonly recognise the RGD peptide motif (Humphries et al, *Journal of Cell Science*, 2006, 119, 3901).

The 8 RGD-binding integrins have different binding affinities and specificities for different RGD-containing ligands. Ligands include proteins such as fibronectin, vitronectin, osteopontin, and the latency associated peptides (LAPs) of Transforming Growth Factor $\beta_1$ and $\beta_3$ (TGF$\beta_1$ and TGF$\beta_3$). Integrin binding to the LAPs of TGF$\beta_2$ and TGF$\beta_3$ has been shown in several systems to enable activation of the TGF$\beta_1$ and TGF$\beta_3$ biological activities, and subsequent TGF$\beta$-driven biologies (Worthington et al, *Trends in Biochemical Sciences*, 2011, 36, 47). The diversity of such ligands, coupled with expression patterns of RGD-binding integrins, generates multiple opportunities for disease intervention. Such diseases include fibrotic diseases (Margadant et al, EMBO reports, 2010, 11, 97), inflammatory disorders, cancer (Desgrosellier et al, *Nature Reviews Cancer*, 2010, 10, 9), restenosis, and other diseases with an angiogenic component (Weis et al, *Cold Spring. Harb. Perspect. Med.* 2011, 1, a 006478).

A significant number of $\alpha_v$ integrin antagonists (Goodman et al, *Trends in Pharmacological Sciences*, 2012, 33, 405) have been disclosed in the literature including inhibitory antibodies, peptides and small molecules. For antibodies these include the pan-$\alpha_v$ antagonists Intetumumab and Abituzumab (Gras, *Drugs of the Future*, 2015, 40, 97), the selective $\alpha_v\beta_3$ antagonist Etaracizumab, and the selective $\alpha_v\beta_6$ antagonist STX-100. Cilengitide is a cyclic peptide antagonist that inhibits both $\alpha_v\beta_3$ and $\alpha_v\beta_5$ and SB-267268 is an example of a compound (Wilkinson-Berka et al, *Invest. Ophthalmol. Vis. Sci.*, 2006, 47, 1600), that inhibits both $\alpha_v\beta_3$ and $\alpha_v\beta_5$. Invention of compounds to act as antagonists of differing combinations of $\alpha_v$ integrins enables novel agents to be generated tailored for specific disease indications.

Pulmonary fibrosis represents the end stage of several interstitial lung diseases, including the idiopathic interstitial pneumonias, and is characterised by the excessive deposition of extracellular matrix within the pulmonary interstitium. Among the idiopathic interstitial pneumonias, idiopathic pulmonary fibrosis (IPF) represents the commonest and most fatal condition with a typical survival of 3 to 5 years following diagnosis. Fibrosis in IPF is generally progressive, refractory to current pharmacological intervention and inexorably leads to respiratory failure due to obliteration of functional alveolar units. IPF affects approximately 500,000 people in the USA and Europe.

There are in vitro experimental, animal and IPF patient immunohistochemistry data to support a key role for the epithelially restricted integrin, $\alpha_v\beta_6$, in the activation of TGF$\beta$1. Expression of this integrin is low in normal epithelial tissues and is significantly up-regulated in injured and inflamed epithelia including the activated epithelium in IPF. Targeting this integrin, therefore, reduces the theoretical possibility of interfering with wider TGF$\beta$ homeostatic roles. Partial inhibition of the $\alpha_v\beta_6$ integrin by antibody blockade has been shown to prevent pulmonary fibrosis without exacerbating inflammation (Horan GS et al Partial inhibition of integrin $\alpha_v\beta_6$ prevents pulmonary fibrosis without exacerbating inflammation. Am J *Respir Crit Care Med* 2008 177: 56-65). Outside of pulmonary fibrosis, $\alpha_v\beta_6$ is also considered an important promoter of fibrotic disease of other organs, including liver and kidney (Reviewed in Henderson NC et al Integrin-mediated regulation of TGF$\beta$ in Fibrosis, Biochimica et Biophysica Acta—Molecular Basis of Disease 2013 1832:891-896), suggesting that an $\alpha_v\beta_6$ antagonist could be effective in treating fibrotic diseases in multiple organs.

Consistent with the observation that several RGD-binding integrins can bind to, and activate, TGF$\beta$, different $\alpha_v$ integrins have recently been implicated in fibrotic disease (Henderson NC et al Targeting of $\alpha_v$ integrin identifies a core molecular pathway that regulates fibrosis in several organs *Nature Medicine* 2013 Vol 19, Number 12: 1617-1627; Sarrazy V et al Integrins $\alpha$v$\beta$5 and $\alpha$v$\beta$3 promote latent TGF-$\beta$1 activation by human cardiac fibroblast contraction Cardiovasc Res 2014 102:407-417; Minagawa S et al Selective targeting of TGF-$\beta$ activation to treat fibroinflammatory airway disease *Sci Transl Med* 2014 Vol 6, Issue 241: 1-14; Reed NI et al . The $\alpha_v\beta_1$ integrin plays a critical in vivo role in tissue fibrosis *Sci Transl Med* 2015 Vol 7, Issue 288: 1-8). Therefore inhibitors against specific members of the RGD binding integrin families, or with specific selectivity fingerprints within the RGD binding integrin family, may be effective in treating fibrotic diseases in multiple organs.

SAR relationships of a series of integrin antagonists against $\alpha_v\beta_3$, $\alpha_v\beta_5$, $\alpha_v\beta_6$ and $\alpha_v\beta_8$ have been described (Macdonald, SJF et al. Structure activity relationships of $\alpha_v$ integrin antagonists for pulmonary fibrosis by variation in aryl substituents. ACS *MedChemLett* 2014, 5, 1207-1212. 19 Sept. 2014).

It is an object of the invention to provide $\alpha_v\beta_6$ antagonists, including those with activities against other $\alpha_v$ integrins, such as $\alpha_v\beta_1$, $\alpha_v\beta_3$, $\alpha_v\beta_5$ or $\alpha_v\beta_8$.

SUMMARY OF THE INVENTION

In a first aspect of the present invention, there is provided a compound of Formula (I):

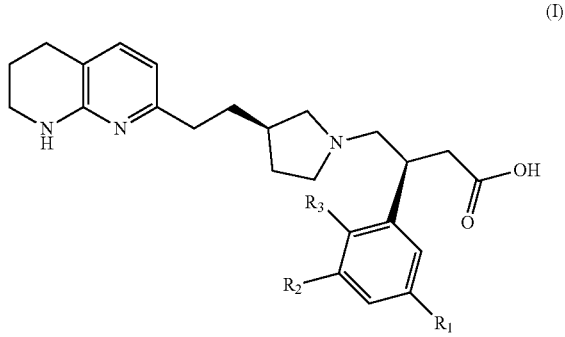

(I)

wherein
either $R_1$ and $R_2$ each independently represent hydrogen or a group —O—$CR_5R_6$—$CR_7R_8$—O($C_{1-3}$-alkyl)
  wherein $R_5$, $R_6$, $R_7$ and $R_8$ each independently represent hydrogen or methyl; or one of $R_5$ or $R_6$ represents —$CH_2OMe$;
  with the proviso that $R_1$ and $R_2$ cannot both represent hydrogen;
or $R_2$ represents hydrogen and $R_1$ represents
  (i) a group selected from

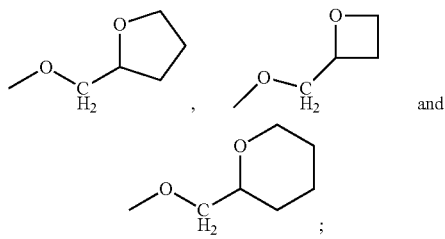

or
  (ii) a group selected from

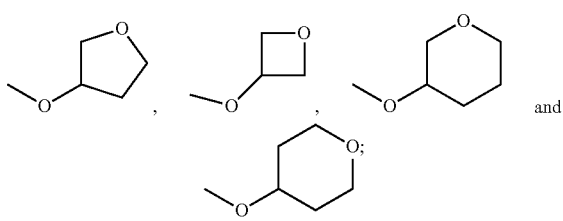

or
  (iii) a group selected from

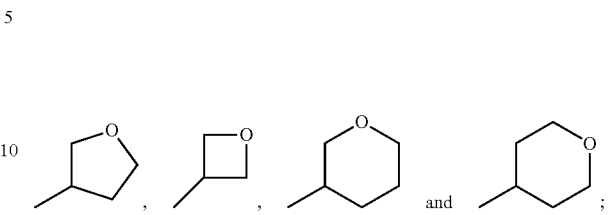

or $R_2$ represents hydrogen and $R_1$ represents or $R_2$ represents hydrogen and $R_1$ represents a group O($CH_2$)$_3$ OMe;

or one of $R_1$ and $R_2$ represents a group —O($CH_2$)$_2$Me and the other represents —O($CH_2$)$_2$F;

and $R_3$ represents hydrogen or fluoro; with the proviso that where $R_1$ and $R_2$ both represent other than hydrogen then $R_3$ represents hydrogen;

or a pharmaceutically acceptable salt thereof.

Compounds of Formula (I) and their pharmaceutically acceptable salts have $\alpha_v\beta_6$ integrin antagonist activity and are believed to be of potential use for the treatment of certain disorders. The term $\alpha_v\beta_6$ antagonist activity includes $\alpha_v\beta_6$ inhibitor activity herein.

In a second aspect of the present invention, there is provided a pharmaceutical composition comprising a compound of Formula (I) or a pharmaceutically acceptable salt thereof and a pharmaceutically acceptable carrier, diluent or excipient.

In a third aspect of the present invention, there is provided a compound of Formula (I), or a pharmaceutically acceptable salt thereof for use in therapy, in particular in the treatment of a disease or condition for which an $\alpha_v\beta_6$ integrin antagonist is indicated.

In a fourth aspect of the present invention, there is provided a method of treatment of a disease or condition for which an $\alpha_v\beta_6$ integrin antagonist is indicated in a human in need thereof which comprises administering to such human a therapeutically effective amount of compound of Formula (I) or a pharmaceutically acceptable salt thereof.

In a fifth aspect of the present invention, there is provided the use of a compound of Formula (I) or a pharmaceutically acceptable salt thereof in the manufacture of a medicament for the treatment of a disease or condition for which an $\alpha_v\beta_6$ integrin antagonist is indicated.

DETAILED DESCRIPTION OF THE INVENTION

The present invention relates to a compound of Formula (I):

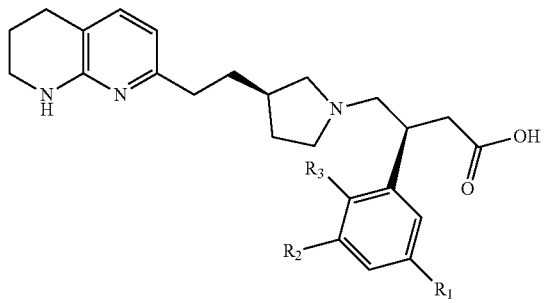

(I)

wherein
either $R_1$ and $R_2$ each independently represent hydrogen or a group —O—$CR_5R_6$—$CR_7R_8$—O($C_{1-3}$-alkyl) wherein $R_5$, $R_6$, $R_7$ and $R_8$ each independently represent hydrogen or methyl; or one of $R_5$ or $R_6$ represents —$CH_2$OMe;
  with the proviso that $R_1$ and $R_2$ cannot both represent hydrogen;
or $R_2$ represents hydrogen and $R_1$ represents
  (i) a group selected from

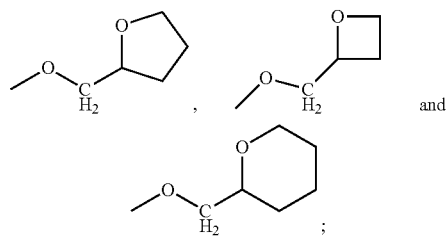

or
  (ii) a group selected from

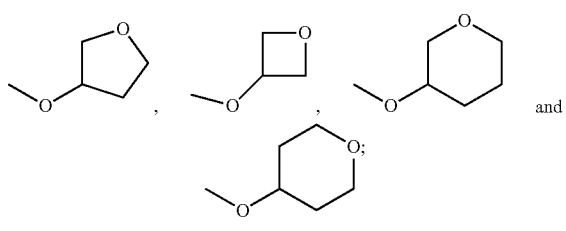

or
  (iii) a group selected from

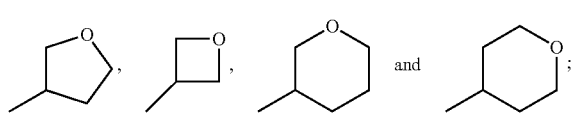

or $R_2$ represents hydrogen and $R_1$ represents

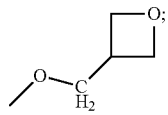

or $R_2$ represents hydrogen and $R_1$ represents a group —O($CH_2)_3$OMe;
or one of $R_1$ and $R_2$ represents a group —O($CH_2)_2$OMe and the other represents —O($CH_2)_2$F;
and $R_3$ represents hydrogen or fluoro; with the proviso that where $R_1$ and $R_2$ both represent other than hydrogen then $R_3$ represents hydrogen;
or a pharmaceutically acceptable salt thereof.

In an embodiment, the present invention relates to a compound of Formula (I) wherein either $R_1$ and $R_2$ each independently represent hydrogen or a group —O—$CR_5R_6$—$CR_7R_8$—O($C_{1-3}$-alkyl)
  wherein $R_5$, $R_6$, $R_7$ and $R_8$ each independently represent hydrogen or methyl; or one of $R_5$ or $R_6$ represents —$CH_2$OMe;
  with the proviso that $R_1$ and $R_2$ cannot both represent hydrogen;
or $R_2$ represents hydrogen and $R_1$ represents
  (i) a group selected from

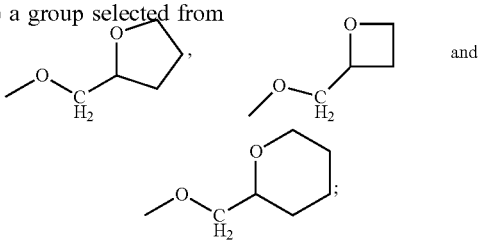

or
  (ii) a group selected from

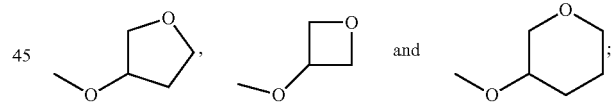

or
  (iii) a group selected from

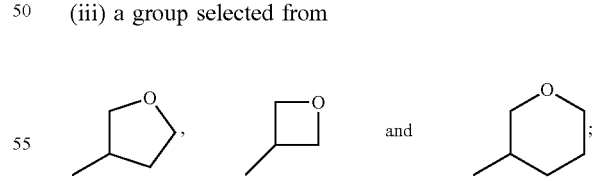

or $R_2$ represents hydrogen and $R_1$ represents

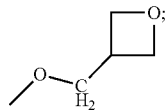

or $R_2$ represents hydrogen and $R_1$ represents a group —O(CH$_2$)$_3$OMe;

or one of $R_1$ and $R_2$ represents a group —O(CH$_2$)$_2$OMe and the other represents —O(CH$_2$)$_2$F;

and $R_3$ represents hydrogen or fluoro; with the proviso that where $R_1$ and $R_2$ both represent other than hydrogen then $R_3$ represents hydrogen;

or a pharmaceutically acceptable salt thereof.

In an embodiment, $R_1$ and $R_2$ each independently represent hydrogen or a group —O—CR$_5$R$_6$—CR$_7$R$_8$—O(C$_{1-3}$-alkyl) wherein $R_5$, $R_6$, $R_7$ and $R_8$ each independently represent hydrogen or methyl; or one of $R_5$ or $R_6$ represents —CH$_2$OMe; with the proviso that $R_1$ and $R_2$ cannot both represent hydrogen.

In an embodiment, $R_1$ and $R_2$ each independently represent hydrogen or a group —O—CR$_5$R$_6$—CR$_7$R$_8$—O(C$_{1-3}$-alkyl) wherein $R_5$, $R_6$, $R_7$ and $R_8$ each independently represent hydrogen or methyl; with the proviso that $R_1$ and $R_2$ cannot both represent hydrogen.

In an embodiment, one of $R_1$ and $R_2$ represents hydrogen and the other represents a group —O—CR$_5$R$_6$—CR$_7$R$_8$—O(C$_{1-3}$-alkyl) wherein $R_5$, $R_6$, $R_7$ and $R_8$ each independently represent hydrogen or methyl.

In an embodiment, both of $R_1$ and $R_2$ represents a group —O—CR$_5$R$_6$—CR$_7$R$_8$—O(C$_{1-3}$-alkyl) wherein $R_5$, $R_6$, $R_7$ and $R_8$ each independently represent hydrogen or methyl.

In an embodiment, one of $R_1$ and $R_2$ represents hydrogen and the other represents a group selected from 2-methoxyethoxy, 2-methoxypropoxy, 2-methoxy-2-methylpropoxy, (1-methoxypropan-2-yl)oxy, or (1-methoxy-2-methylpropan-2-yl)oxy. In a further embodiment, one of $R_1$ and $R_2$ represents hydrogen and the other represents a group selected from 2-methoxypropoxy or (1-methoxy-2-methylpropan-2-yl)oxy.

In a specific embodiment, one of $R_1$ and $R_2$ represents hydrogen and the other represents 2-isopropoxyethoxy.

In a specific embodiment, both of $R_1$ and $R_2$ represent 2-methoxyethoxy.

In an embodiment $R_2$ represents hydrogen and $R_1$ represents a group selected from

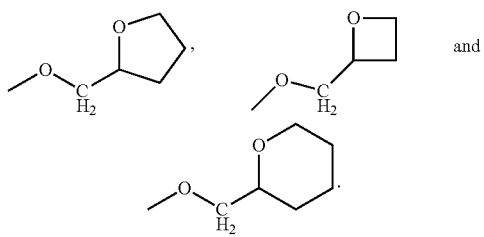

In a specific embodiment $R_2$ represents hydrogen and $R_1$ represents (tetrahydrofuran-2-yl)methoxy.

In an embodiment $R_2$ represents hydrogen and $R_1$ represents a group selected from

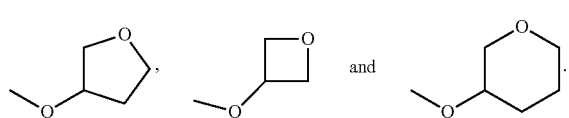

In an embodiment $R_2$ represents hydrogen and $R_1$ represents a group

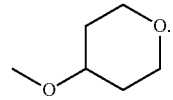

In a specific embodiment $R_2$ represents hydrogen and $R_1$ represents (tetrahydrofuran-3-yl)oxy.

In a specific embodiment $R_2$ represents hydrogen and $R_1$ represents (oxetan-3-yl)oxy.

In an embodiment $R_2$ represents hydrogen and $R_1$ represents a group selected from

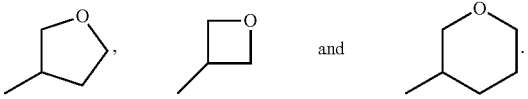

In a specific embodiment $R_2$ represents hydrogen and $R_1$ represents tetrahydrofuran-3-yl.

In a specific embodiment $R_2$ represents hydrogen and $R_1$ represents oxetan-3-yl.

In a specific embodiment $R_3$ represents hydrogen. In a further specific embodiment $R_3$ represents fluoro.

In an embodiment, $R_3$ represents fluoro, $R_2$ represents hydrogen; and $R_1$ is as defined above.

It is to be understood that the present invention covers all combinations of particular groups described hereinabove.

In an embodiment, specific compounds of this invention include:
(S)-3-(3-(2-methoxyethoxy)phenyl)-4-((R)-3-(2-(5,6,7,8-tetrahydro-1,8-naphthyridin-2-yl)ethyl)pyrrolidin-1-yl)butanoic acid;
(S)-3-(3-((R)-2-methoxypropoxy)phenyl)-4-((R)-3-(2-(5,6,7,8-tetrahydro-1,8-naphthyridin-2-yl)ethyl)pyrrolidin-1-yl)butanoic acid;
(S)-3-(3-((S)-2-methoxypropoxy)phenyl)-4-((R)-3-(2-(5,6,7,8-tetrahydro-1,8-naphthyridin-2-yl)ethyl)pyrrolidin-1-yl)butanoic acid;
(S)-3-(3-(2-methoxy-2-methylpropoxy)phenyl)-4-((R)-3-(2-(5,6,7,8-tetrahydro-1,8-naphthyridin-2-yl)ethyl)pyrrolidin-1-yl)butanoic acid;
3-(3-(((S)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid;
(S)-3-(3-((1-methoxy-2-methylpropan-2-yl)oxy)phenyl)-4-((R)-3-(2-(5,6,7,8-tetrahydro-1,8-naphthyridin-2-yl)ethyl)pyrrolidin-1-yl)butanoic acid;
(S)-3-(3-(((R)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid;
(S)-3-(3-(2-Isopropoxyethoxy)phenyl)-4-((R)-3-(2-(5,6,7,8-tetrahydro-1,8-naphthyridin-2-yl)ethyl)pyrrolidin-1-yl)butanoic acid;
(S)-3-(3,5-Bis(2-methoxyethoxy)phenyl)-4-((R)-3-(2-(5,6,7,8-tetrahydro-1,8-naphthyridin-2-yl)ethyl)pyrrolidin-1-yl)butanoic acid; or
(S)-3-(2-Fluoro-5-(2-methoxyethoxy)phenyl)-4-((R)-3-(2-(5,6,7,8-tetrahydro-1,8-naphthyridin-2-yl)ethyl)pyrrolidin-1-yl)butanoic acid;
or a pharmaceutically acceptable salt thereof.

In a further embodiment, specific compounds of this invention include:

(S)-4-((R)-3-(2-(5,6,7,8-tetrahydro-1,8-naphthyridin-2-yl) ethyl)pyrrolidin-1-yl)-3-(3-(((S)-tetrahydrofuran-3-yl) oxy)phenyl)butanoic acid; or (S)-4-((R)-3-(2-(5,6,7,8-tetrahydro-1,8-naphthyridin-2-yl) ethyl)pyrrolidin-1-yl)-3-(3-(((R)-tetrahydrofuran-3-yl) oxy)phenyl)butanoic acid;

or a pharmaceutically acceptable salt thereof.

In a further embodiment, specific compounds of this invention include:

(3S)-4-((R)-3-(2-(5,6,7,8-Tetrahydro-1,8-naphthyridin-2-yl) ethyl)pyrrolidin-1-yl)-3-(3-(tetrahydrofuran-3-yl)phenyl) butanoic acid (Isomer 1); or (3S)-4-((R)-3-(2-(5,6,7,8-Tetrahydro-1,8-naphthyridin-2-yl) ethyl)pyrrolidin-1-yl)-3-(3-(tetrahydrofuran-3-yl)phenyl) butanoic acid (Isomer 2);

or a pharmaceutically acceptable salt thereof.

In a further embodiment, specific compounds of this invention include:

(S)-4-((R)-3-(2-(5,6,7,8-Tetrahydro-1,8-naphthyridin-2-yl) ethyl)pyrrolidin-1-yl)-3-(3-(((R)-tetrahydrofuran-2-yl) methoxy)phenyl)butanoic acid; or (S)-4-((R)-3-(2-(5,6,7,8-tetrahydro-1,8-naphthyridin-2-yl) ethyl)pyrrolidin-1-yl)-3-(3-(((S)-tetrahydrofuran-2-yl) methoxy)phenyl)butanoic acid;

or a pharmaceutically acceptable salt thereof.

In a further embodiment, specific compounds of this invention include:

3-(3-((1,3-Dimethoxypropan-2-yl)oxy)phenyl)-4-((R)-3-(2-(5,6,7,8-tetrahydro-1,8-naphthyridin-2-yl)ethyl)pyrrolidin-1-yl)butanoic acid;

3-(3-(2-Fluoroethoxy)-5-(2-methoxyethoxy)phenyl)-4-((R)-3-(2-(5,6,7,8-tetrahydro-1,8-naphthyridin-2-yl)ethyl)pyrrolidin-1-yl)butanoic acid;

3-(3-(3-Methoxypropoxy)phenyl)-4-((R)-3-(2-(5,6,7,8-tetrahydro-1,8-naphthyridin-2-yl)ethyl)pyrrolidin-1-yl)butanoic acid; or 3-(3-(Oxetan-3-ylmethoxy)phenyl)-4-((R)-3-(2-(5,6,7,8-tetrahydro-1,8-naphthyridin-2-yl)ethyl)pyrrolidin-1-yl)butanoic acid;

or a pharmaceutically acceptable salt thereof.

In a further embodiment, specific compounds of this invention include:

(S)-3-(3-(Oxetan-3-yloxy)phenyl)-4-((R)-3-(2-(5,6,7,8-tetrahydro-1,8-naphthyridin-2-yl)ethyl)pyrrolidin-1-yl)butanoic acid;

(S)-4-((R)-3-(2-(5,6,7,8-Tetrahydro-1,8-naphthyridin-2-yl) ethyl)pyrrolidin-1-yl)-3-(3-((tetrahydro-2H-pyran-4-yl) oxy)phenyl)butanoic acid;

or a pharmaceutically acceptable salt thereof.

Compounds of Formula (I) have both a basic amine group and a carboxylic acid group and can consequently be in the form of a zwitterion, also known as an inner salt. Therefore, in an embodiment the compound of Formula (I) is in a zwitterion form.

It will be appreciated that the present invention covers compounds of Formula (I) as the parent compound and as pharmaceutically acceptable salts thereof. In one embodiment the invention relates to compounds of Formula (I). In another embodiment the invention relates to a pharmaceutically acceptable salt of a compound of Formula (I).

As used herein, the term 'pharmaceutically acceptable salt' refers to a salt that retains the desired biological activity of the subject compound and exhibits minimal undesired toxicological effects.

For a review of suitable pharmaceutically acceptable salts see Berge et al., *J. Pharm. Sci.*, 66: 1-19, (1977). Suitable pharmaceutically acceptable salts are also listed in P H Stahl and C G Wermuth, editors, *Handbook of Pharmaceutical Salts*; Properties, Selection and Use, Weinheim/Zurich: Wiley-VCH/VHCA, 2002.

Suitable pharmaceutically acceptable salts can include acid addition salts with inorganic acids such, for example, as hydrochloric acid, hydrobromic acid, nitric acid, phosphoric acid, or sulfuric acid, or with organic acids such, for example as methanesulfonic acid, ethanesulfonic acid, p-toluenesulfonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulfonic, naphthalenesulfonic such as 2-naphthalenesulfonic, hexanoic acid or acetylsalicylic acid. Suitable pharmaceutically acceptable salts can include base addition salts such as, for example, ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

In an embodiment the pharmaceutically acceptable salt is a maleate salt or a citrate salt. Typically, a pharmaceutically acceptable salt may readily be prepared by reaction with the appropriate acid or base, optionally in a suitable solvent such as an organic solvent. The resultant salt may be isolated by crystallisation and filtration or may be recovered by evaporation of the solvent.

Other non-pharmaceutically acceptable salts, e.g. formates, oxalates or trifluoroacetates, may be used, for example, in the preparation of the compounds of Formula (I) and their pharmaceutically acceptable salts.

The invention includes within its scope all possible stoichiometric and non-stoichiometric forms of the pharmaceutically acceptable salts of the compounds of Formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. The compounds of Formula (I) and pharmaceutically acceptable salts thereof may exist in solvated and unsolvated form.

The compounds of Formula (I) may be in crystalline or amorphous form. Furthermore, some of the crystalline forms of the compounds of Formula (I) may exist in different polymorphic forms. Polymorphic forms of compounds of Formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds of Formula (I) may contain one or more asymmetric centres as a result of the groups $R_1$ and $R_2$ as defined above, so that optical isomers, e.g. diastereoisomers may be formed. Accordingly, the present invention encompasses such isomers of the compounds of Formula (I) whether as individual isomers isolated such as to be substantially free of the other isomer (i.e. pure) or as mixtures.

An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography, HPLC or a combination of these techniques.

Compounds of Formula (I) may exist in one of several tautomeric forms. It will be understood that the present invention encompasses all tautomers of the compounds of Formula (I) whether as individual tautomers or as mixtures thereof.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_3)$alkyl" in the definition of $R_1$ and $R_2$ above refers to an unsubstituted alkyl moiety containing from 1 to 3 carbon atoms; exemplary alkyls include methyl, ethyl, n-propyl and isopropyl. In an embodiment the term "$(C_1-C_3)$alkyl" in the definition of $R_1$ and $R_2$ above represents methyl. In an embodiment the term "$(C_1-C_3)$alkyl" in the definition of $R_1$ and $R_2$ above represents isopropyl.

As used herein, the term "optionally" means that the subsequently described event(s) may or may not occur, and includes both event(s) that occur and event(s) that do not occur.

As used herein, the term "treatment" refers to alleviating the specified condition, eliminating or reducing one or more symptoms of the condition, slowing or eliminating the progression of the condition, and delaying the reoccurrence of the condition in a previously afflicted or diagnosed patient or subject.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, or amelioration of a disease, disorder, or side effect, or a decrease in the rate of advancement of a disease or disorder. The term also includes within its scope amounts effective to enhance normal physiological function.

Compound Preparation

The compounds of Formula (I) or their salts, including pharmaceutically acceptable salts, may be made by a variety of methods, including standard chemistry. Any previously defined variable will continue to have the previously defined meaning unless otherwise indicated. Illustrative general synthetic methods are set out below and then specific compounds of Formula (I) are prepared in the Examples.

Compounds of Formula (I) may be prepared by a process involving first deprotection i.e. cleavage of the ester group, followed by conversion to a salt, of a compound of Formula (II):

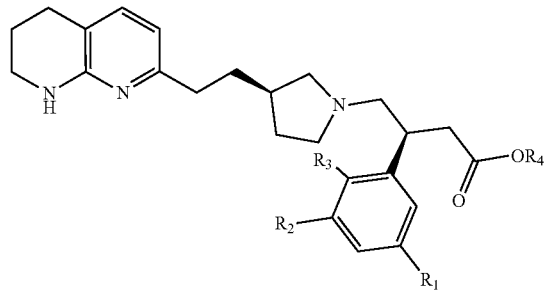

wherein $R_1$, $R_2$ and $R_3$ are each as hereinbefore defined, and $R_4$ is a $C_{1-6}$ alkyl group, for example methyl or tert-butyl.

The deprotection of a compound of Formula (II) where $R_4$ is methyl may be accomplished by base hydrolysis using for example aqueous lithium hydroxide, sodium hydroxide or potassium hydroxide in a suitable solvent, such as methanol, THF or 1,4-dioxane.

The deprotection of a compound of Formula (II) where $R_4$ is tert-butyl may be accomplished by acid cleavage using for example trifluoroacetic acid or HCl in a suitable solvent such as dichloromethane, 1,4-dioxane, or water.

After the cleavage of the ester group the resulting product may be converted to the required salt by methods well known to those skilled in the art.

In one embodiment the conversion of the zwitterion to the hydrochloride salt is achieved by treatment of a solution of the zwitterion in an inert organic solvent such as acetonitrile or acetone with an aqueous hydrochloric acid solution, concentration of the resulting salt solution and crystallisation from acetonitrile.

Compounds of Formula (II) may be prepared by a coupling process involving a compound of Formula (III),

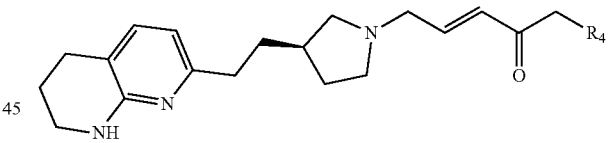

where $R_4$ is as defined previously and the geometry of the double bond may be (E) or mixture of (E) and (Z) isomers, preferably pure (E) isomer,
with a boronate ester or a boronic acid of Formula (IV)

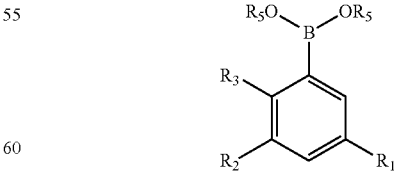

wherein $R_1$, $R_2$ and $R_3$ are each as hereinbefore defined, and each $R_5$ is hydrogen or $C_{1-4}$ alkyl, or both $R_5$ groups are linked to form a $C_{2-6}$ alkyl group.

The coupling reaction in the presence of (R)-BINAP provides a diastereoisomeric mixture with a predominant isomer. The diastereoisomers may be separated by a variety of separation techniques, including crystallisation, chromatography or preferably preparative chiral HPLC. The predominant diastereoisomer when using (R)-BINAP has the (S) configuration.

Compounds of Formula (IV) may be used as the pure boronic acid ($R_5$=H), or as a boronic acid ester (each $R_5$=alkyl group, or both $R_5$ are linked e.g. to form a pinacol ester), which may be converted in situ to the boronic acid in the presence of water and a base, such as potassium hydroxide. The methyl ester group of a compound of Formula (II) may be hydrolysed under the basic reaction conditions during the coupling process to provide a compound of Formula (I) directly without the need for a separate hydrolysis step.

Compounds of Formula (III) may be prepared by an alkylation reaction of a compound of Formula (V):

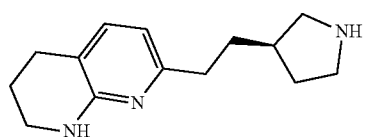

(V)

with (E)-($C_{1-6}$-alkyl) 4-bromobut-2-enoate (for example (E)-methyl 4-bromobut-2-enoate where $R_4$ is methyl or (E)-tert-butyl 4-bromobut-2-enoate where $R_4$ is tert-butyl (disclosed at page 32 of WO2014/154725), and in the presence of a base, such as diisopropylethylamine in a suitable solvent such as dichloromethane.

Alternatively, the alkylation of a compound of Formula (V) may be effected by coupling a compound of Formula (V) with (E)-($C_{1-6}$-alkyl) 4-acetoxybut-2-enoate, for example with (E)-methyl 4-acetoxybut-2-enoate where $R_4$ is methyl, or with tert-butyl (E)-tert-butyl 4-acetoxybut-2-enoate where $R_4$ is tert-butyl (respectively disclosed at pages 50 and 32 of WO2014/15475), in the presence of a palladium catalyst, such as 1,1'-bis(diphenylphosphino)ferrocene]dichloropalladium(II), in the presence of a base, such as diisopropylethylamine or triethylamine and in a suitable solvent, such as dichloromethane at ambient temperature.

Compounds of Formula (V) may be prepared by cleavage of the tert-butoxycarbonyl protecting group of a compound of Formula (VI) using an acid, such as hydrogen chloride in 1,4-dioxane.

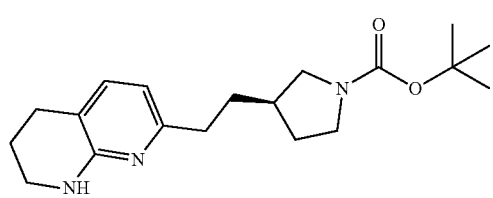

(VI)

Compounds of Formula (VI) may be prepared from a compound of Formula (VII):

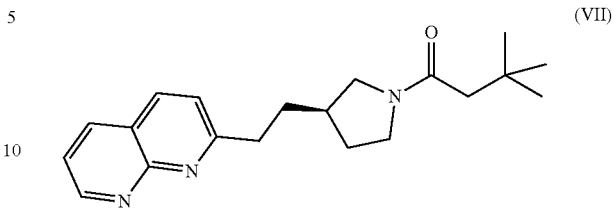

(VII)

by hydrogenation over a catalyst, such as 5% rhodium on carbon in a solvent, such as ethanol or ethyl acetate.

The compound of Formula (VII) [(R)-tert-Butyl 3-(2-(1, 8-naphthyridin-2-yl)ethyl)pyrrolidine-1-carboxylate] may be prepared by methods described in WO2014/154725, page 31, and further purified by re-crystallisation of the 4-toluenesulfonic acid salt, as described herein.

Compounds of Formula (IV), where both $R_5$ groups and the oxygen atoms to which they are attached represent a pinacol moeity, may be prepared from compounds of Formula (VIII):

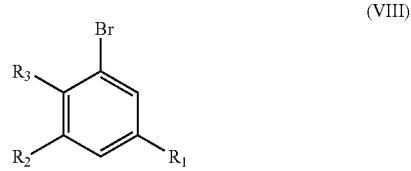

(VIII)

with bis(pinacolato)diboron (available from Aldrich), in the presence of a palladium catalyst, such as 1,1'-bis(diphenylphosphino)ferrocene]dichloropalladium(II) complex with dichloromethane [$PdCl_2$(dppf)-$CH_2Cl_2$ adduct] (available from Aldrich) and in the presence of potassium acetate in an inert solvent, such as 1,4-dioxane, at elevated temperature, for example 90° C., and in an inert atmosphere, such as nitrogen. Alternatively such compounds of Formula (IV) may be prepared using a palladium catalyst, such as tris (dibenzylideneacetone)dipalladium (available from Aldrich), and in the presence of a phosphine ligand, such as 2-dicyclohexylphosphino-2',4',6'-triisopropylbiphenyl (X-PHOS) (available from Aldrich), and in the presence of potassium acetate, in an inert solvent, such as 1,4-dioxane, at elevated temperature, for example 110° C., and in an inert atmosphere, such as nitrogen. Addition of water to the reaction mixture at the end of the reaction causes hydrolysis of the resulting pinacolato ester to provide the required boronic acid. Compounds of Formula (IV) where $R_5$ is hydrogen can alternatively be prepared by a three-step process involving reaction of a compound of Formula (VIII) with an organolithium reagent, such as n-butyllithium, in an inert solvent, such as THF or 2-methyl-tetrahydrofuran, at low temperature, such as between −60 and −78° C., and in an inert atmosphere of nitrogen or argon, followed by reaction with a trialkylborate ester such as tri(isopropyl) borate, and finally hydrolysis.

Compounds of Formula (VIII) may be prepared by methods as described herein. For example, compounds of Formula (VIII) where $R_1$ is attached to the phenyl ring via an oxygen may be prepared from 3-bromophenol by an alkylation reaction, for example reaction with an alkyl halide e.g. alkyl bromide or a sulfonate ester e.g. alkyl tosylate optionally in the presence of a base, in an inert solvent such as THF or DMF, and at a temperature between 20 and 60° C., or by reacting with an epoxide. Alternatively 3-bromophenol may be alkylated via a Mitsunobu reaction using an alcohol in the presence of a phosphine e.g. triphenylphosphine and an azodicarboxylate for example diisopropyl azodicarboxylate (DIAD), in an inert solvent, such as THF and at a temperature between 0 and 25° C. For example, compounds of formula (VIII) where $R_1$ is attached to the phenyl ring via a carbon atom may be prepared by addition of an appropriately substituted aryl lithium to a ketone to form a carbinol, which is then reduced using triethylsilane in the presence of TFA.

It will be appreciated that in any of the routes described above it may be advantageous to protect one or more functional groups. Examples of protecting groups and the means for their removal can be found in T. W. Greene 'Protective Groups in Organic Synthesis' (3rd edition, J. Wiley and Sons, 1999). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The absolute configuration of a compound of Formula (I) may be obtained following an independent enantioselective asymmetric synthesis from an intermediate of known absolute configuration. Alternatively an enantiomerically pure compound of Formula (I) may be converted into a compound whose absolute configuration is known. In either case comparison of spectroscopic data, optical rotation and retention times on an analytical chiral HPLC column may be used to confirm absolute configuration. A third option, where feasible, is determination of absolute configuration from an X-ray crystal structure.

Certain intermediate compounds of Formulae (II) and (VIII) are also believed to be novel and therefore form yet a further aspect of the invention.

Methods of Use

The compounds of Formula (I) and pharmaceutically acceptable salts thereof have $\alpha_v$ integrin antagonist activity, particularly $\alpha_v\beta_6$ receptor activity, and thus have potential utility in the treatment of diseases or conditions for which an $\alpha_v\beta_6$ antagonist is indicated.

The present invention thus provides a compound of Formula (I) or a pharmaceutically acceptable salt thereof for use in therapy. The compound of Formula (I) or pharmaceutically acceptable salt thereof can be for use in the treatment of a disease or condition for which an $\alpha_v\beta_6$ integrin antagonist is indicated.

The present invention thus provides a compound of Formula (I) or a pharmaceutically acceptable salt thereof for use in the treatment of a disease or condition for which an $\alpha_v\beta_6$ integrin antagonist is indicated.

Also provided is the use of a compound of Formula (I) or a pharmaceutically acceptable salt thereof in the manufacture of a medicament for the treatment of a disease or condition for which an $\alpha_v\beta_6$ integrin antagonist is indicated.

Also provided is a method of treating a disease or conditions for which an $\alpha_v\beta_6$ integrin antagonist is indicated in a subject in need thereof which comprises administering a therapeutically effective amount of compound of Formula (I) or a pharmaceutically acceptable salt thereof.

Suitably the subject in need thereof is a mammal, particularly a human.

Fibrotic diseases involve the formation of excess fibrous connective tissue in an organ or tissue in a reparative or reactive process. $\alpha_v\beta_6$ antagonists are believed to be useful in the treatment of a variety of such diseases or conditions including those dependent on $\alpha_v\beta_6$ integrin function and on activation of transforming growth factor beta via alpha v integrins. Accordingly, in one embodiment the disease or condition for which an $\alpha_v\beta_6$ antagonist is indicated is a fibrotic disease. Diseases may include but are not limited to pulmonary fibrosis (e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, ARDS associated fibrosis, acute lung injury, radiation-induced fibrosis, familial pulmonary fibrosis, pulmonary hypertension); renal fibrosis (diabetic nephropathy, IgA nephropathy, lupus nephritis, focal segmental glomerulosclerosis (FSGS), transplant nephropathy, autoimmune nephropathy, drug-induced nephropathy, hypertension-related nephropathy, nephrogenic systemic fibrosis); liver fibrosis (virally-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease, epidermolysis bullosa dystrophica, oral submucous fibrosis); ocular fibrosis (age-related macular degeneration (AMD), diabetic macular oedema, dry eye, glaucoma) corneal scarring, corneal injury and corneal wound healing, prevention of filter bleb scarring post trabeculectomy surgery; cardiac fibrosis (congestive heart failure, atherosclerosis, myocardial infarction, endomyocardial fibrosis, hypertrophic cardiomyopathy (HCM)) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection. There may be further benefit from additional inhibition of $\alpha_v\beta_1$, $\alpha_v\beta_5$ or $\alpha_v\beta_8$ integrins In addition, pre-cancerous lesions or cancers associated with $\alpha_v\beta_6$ integrins may also be treated (these may include but are not limited to endometrial, basal cell, liver, colon, cervical, oral, pancreas, breast and ovarian cancers, Kaposi's sarcoma, Giant cell tumours and cancer associated stroma). Conditions that may derive benefit from effects on angiogenesis may also benefit (e.g. solid tumours).

The term "disease or condition for which an $\alpha_v\beta_6$ antagonist is indicated", is intended to include any or all of the above disease states.

In one embodiment the disease or condition for which an $\alpha_v\beta_6$ antagonist is indicated is idiopathic pulmonary fibrosis.

In another embodiment the disease or condition for which an $\alpha_v\beta_6$ antagonist is indicated is selected from corneal scarring, corneal injury and corneal wound healing.

Compositions

While it is possible that for use in therapy, a compound of Formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of Formula (I) or a pharmaceutically acceptable salt thereof and a pharmaceutically acceptable carrier, diluent or excipient. The compound of Formula (I) and pharmaceutically acceptable salts thereof are as described above. The carrier, diluent or excipient must be acceptable in the sense of being compatible with the other ingredients of the composition and not deleterious to the recipient thereof.

In accordance with another aspect of the invention there is also provided a process for the preparation of a pharmaceutical composition including admixing a compound of the Formula (I), or a pharmaceutically acceptable salt thereof, with a pharmaceutically acceptable carrier, diluent or excipient. The pharmaceutical composition can be for use in the treatment of any of the conditions described herein.

Further provided is a pharmaceutical composition for the treatment of diseases or conditions for which an $\alpha_v\beta_6$ integrin antagonist is indicated comprising a compound of Formula (I) or a pharmaceutically acceptable salt thereof.

Further provided is a pharmaceutical composition comprising 0.01 to 3000 mg, in an embodiment 0.05 to 1000 mg, of a compound of Formula (I) or a pharmaceutically acceptable salt thereof and 0.1 to 2 g of a pharmaceutically acceptable carrier, diluent or excipient. Since the compounds of Formula (I) or pharmaceutically acceptable salts thereof are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vagina, ocular or parenteral (including subcutaneous, intramuscular, intravenous or intradermal) route. Such compositions may be prepared by any method known in the art of pharmacy, for example by bringing into association the active ingredient with the carrier, diluent or excipient.

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine particle size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like.

Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be prepared as an amorphous molecular dispersion in a polymer matrix, such as hydroxypropylmethyl cellulose acetate succinate, using a spray-dried dispersion (SDD) process to improve the stability and solubility of the drug substance.

The compounds of the invention may also be delivered using a liquid encapsulation technology to improve properties such as bioavailability and stability, in either liquid or semi-solid filled hard capsule or soft gelatin capsule formats.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base. The compounds of this invention can be administered as topical eye drops. The compounds of this invention can be administered via sub-conjunctival, intracameral or intravitreal routes which would necessitate administration intervals that are longer than daily.

Pharmaceutical formulations adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers and a carrier or diluent that has a time delay property. Representative examples of biodegradable compositions can include albumin, gelatin, starch, cellulose, dextrans, polysaccharides, poly (D, L-lactide), poly (D, L-lactide-co-glycolide), poly (glycolide), poly (hydroxybutyrate), poly (allwlcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Pharmaceutical compositions adapted for topical administration in the mouth include lozenges, pastilles and mouth washes.

Pharmaceutical compositions adapted for rectal administration may be presented as suppositories or as enemas.

In one embodiment the pharmaceutical composition is adapted for inhaled administration.

Dosage forms for nasal or inhaled administration may conveniently be formulated as aerosols, solutions, suspensions, gels or dry powders.

For compositions suitable and/or adapted for inhaled administration, it is preferred that the compound of the invention is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of the invention (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose and the compound of the invention. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

The compounds of the invention may be formulated for inhaled or intranasal administration as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

Compositions for inhaled or intranasal administration may also be administered to the lung and other regions of the respiratory tract by nebulisation. Such compositions may be aqueous solutions or suspensions. Solutions for inhalation by nebulisation may be formulated with the addition of agents such as acid or alkali, buffer salts, isotonicity adjusting agents, surfactants or antimicrobials, such as benzylalkonium chloride (BAC). The composition may be sterile and free of antimicrobial preservative. They may be sterilised, for example, by filtration or heating in an autoclave. They may be presented as a non-sterile solution. A single unit dose of a therapeutically effective amount of the compound of the present invention may be provided as a pre-mixed, premeasured formulation, in a single container.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. The compositions may be presented in unitdose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compounds of the invention may be administered in a long-acting parenteral (LAP) drug delivery system. Such drug delivery systems include formulations which aim to provide a slow release of drug once injected. LAP formulations may be particulate based, e.g. nano or micron sized polymeric spherical particles, which once injected would not be retrieved thus acting as a depot formulation; or small rod-like insert devices which may be retrieved if needed. Long acting particulate injectable formulations may be composed of an aqueous suspension of crystalline drug particle, where the drug has low solubility, thus providing a slow dissolution rate. Polymeric based LAP formulations are typically composed of a polymer matrix containing a drug (of hydrophilic or hydrophobic nature) homogeneously dispersed within the matrix. When LAP formulations are polymer based, the polymer widely used is poly-d,l-lactic-co-glycolic acid (PLGA) or versions thereof.

A therapeutically effective amount of a compound of Formula (I) or a pharmaceutically acceptable salt thereof (hereinafter a compound of the invention) will depend upon a number of factors including, for example, the age and weight of the subject, the precise condition requiring treatment and its severity, the nature of the formulation, and the route of administration, and will ultimately be at the discretion of the attendant physician or veterinarian.

In the pharmaceutical composition, each dosage unit for oral or parenteral administration may contain from 0.01 to 3000 mg, or 0.1 to 2000 mg, or more typically 0.5 to 1000 mg of a compound of the invention calculated as the zwitterion parent compound.

Each dosage unit for nasal or inhaled administration preferably contains from 0.001 to 50 mg, more preferably 0.01 to 5 mg, yet more preferably 1 to 50 mg, of a compound of the invention, calculated as the zwitterion parent compound.

For administration of a nebulised solution or suspension, a dosage unit typically contains from 1 to 15 mg which may suitably be delivered once daily, twice daily or more than twice daily. The compound of the invention may be provided in a dry or lyophilised powder for reconstitution in the pharmacy or by the patient, or may, for example, be provided in an aqueous saline solution.

The compounds of the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 50 mg per day, or 1 to 50 mg per day, of the compound of the invention, calculated as the zwitterion parent compound. This amount may be given in a single dose per day or more usually in a number (such as two, three, four, five or six) of sub-doses per day such that the total daily dose is the same. An effective amount of a salt thereof may be determined as a proportion of the effective amount of the compound of Formula (I) per se.

The compounds of the invention may be employed alone or in combination with other therapeutic agents. Combination therapies according to the present invention thus comprise the administration of at least one compound of Formula (I) or a pharmaceutically acceptable salt thereof, and the use of at least one other pharmaceutically active agent. Preferably, combination therapies according to the present invention comprise the administration of at least one compound of Formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, including therapies for allergic disease, inflammatory disease, autoimmune disease, anti-fibrotic therapies and therapies for obstructive airway disease, therapies for diabetic ocular diseases, and therapies for corneal scarring, corneal injury and corneal wound healing.

Anti-allergic therapies include antigen immunotherapy (such as components and fragments of bee venom, pollen, milk, peanut, CpG motifs, collagen, other components of extracellular matrix which may be administered as oral or sublingual antigens), anti-histamines (such as cetirizine, loratidine, acrivastine, fexofenidine, chlorphenamine), and corticosteroids (such as fluticasone propionate, fluticasone furoate, beclomethasone dipropionate, budesonide, ciclesonide, mometasone furoate, triamcinolone, flunisolide, prednisolone, hydrocortisone).

Anti-inflammatory therapies include NSAIDs (such as aspirin, ibuprofen, naproxen), leukotriene modulators (such as montelukast, zafirlukast, pranlukast), and other anti-inflammatory therapies (such as iNOS inhibitors, tryptase inhibitors, IKK2 inhibitors, p38 inhibitors (losmapimod, dilmapimod), elastase inhibitors, beta2 agonists, DP1 antagonists, DP2 antagonists, pI3K delta inhibitors, ITK inhibitors, LP (lysophosphatidic) inhibitors or FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); adenosine a2a agonists (such as adenosine and regadenoson), chemokine antagonists (such as CCR3 antagonists or CCR4 antagonists), mediator release inhibitors.

Therapies for autoimmune disease include DMARDS (such as methotrexate, leflunomide, azathioprine), biopharmaceutical therapies (such as anti-IgE, anti-TNF, anti-interleukins (such as anti-IL-1, anti-IL-6, anti-IL-12, anti-IL-17, anti-IL-18), receptor therapies (such as etanercept and similar agents); antigen non-specific immunotherapies (such as interferon or other cytokines/chemokines, cytokine/ chemokine receptor modulators, cytokine agonists or antagonists, TLR agonists and similar agents).

Other anti-fibrotic therapies includes inhibitors of TGFβ synthesis (such as pirfenidone), tyrosine kinase inhibitors targeting the vascular endothelial growth factor (VEGF), platelet-derived growth factor (PDGF) and fibroblast growth factor (FGF) receptor kinases (such as Nintedanib (BIBF-1120) and imatinib mesylate (Gleevec)), endothelin receptor antagonists (such as ambrisentan or macitentan), antioxidants (such as N-acetylcysteine (NAC); broad-spectrum antibiotics (such as cotrimoxazole, tetracyclines (minocycline hydrochloride)), phosphodiesterase 5 (PDE5) inhibitors (such as sildenafil), anti-αvβx antibodies and drugs (such as anti-αvβ6 monoclonal antibodies such as those described in WO2003100033A2 may be used in combination, intetumumab, cilengitide) may be used in combination.

Therapies for obstructive airway diseases include bronchodilators such as short-acting β2-agonists, such as salbutamol), long-acting β2-agonists (such as salmeterol, formoterol and vilanterol), short-acting muscarinic antagonists (such as ipratropium bromide), long-acting muscarinic antagonists, (such as tiotropium, umeclidinium).

In some embodiments, treatment can also involve combination of a compound of this invention with other existing modes of treatment, for example existing agents for treatment of diabetic ocular diseases, such as anti VEGF therapeutics e.g. Lucentis®, Avastin®, and Aflibercept and steroids, e.g., triamcinolone, and steroid implants containing fluocinolone acetonide.

In some embodiments, treatment can also involve combination of a compound of this invention with other existing modes of treatment, for example existing agents for treatment of corneal scarring, corneal injury or corneal wound healing, such as Gentel®, calf blood extract, Levofloxacin®, and Ofloxacin®.

The compounds and compositions of the invention may be used to treat cancers alone or in combination with cancer therapies including chemotherapy, radiotherapy, targeted agents, immunotherapy and cell or gene therapy.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

It will be appreciated that when the compound of the present invention is administered in combination with one or more other therapeutically active agents normally administered by the inhaled, intravenous, oral, intranasal, ocular topical or other route that the resultant pharmaceutical composition may be administered by the same route. Alternatively, the individual components of the composition may be administered by different routes.

The present invention will now be illustrated by way of example only.

Abbreviations

The following list provides definitions of certain abbreviations as used herein. It will be appreciated that the list is not exhaustive, but the meaning of those abbreviations not herein below defined will be readily apparent to those skilled in the art.

Ac (acetyl)
BCECF-AM (2',7'-bis-(2-carbontethyl)-5-(and-6)-carboxyfluorescein acetoxymethyl ester)
BEH (Ethylene Bridge Hybrid Technology)
Bu (butyl)
CHAPS (3-[(3-Cholamidopropyl)dimethylammonio]-1-propanesulfonate)
Chiralcel OD-H (cellulose tris(3,5-dimethylphenylcarbamate) coated on 5 μm silica gel)
Chiralcel OJ-H (cellulose tris(4-methylbenzoate) coated on 5 μm silica gel)
Chiralpak AD-H (amylose tris(3,5-dimethylphenylcarbamate) coated on 5 μm silica gel)
Chiralpak ID (amylose tris(3-chlorophenylcarbamate) immobilised on 5 μm silica gel)
Chiralpak AS (amylose tris((S)-alpha-methylbenzylcarbamate) coated on 5 μm silica gel)
CSH (Charged Surface Hybrid Technology)
CV (column volume)
DCM (dichloromethane)
DIAD (diisopropyl azodicarboxylate)
DIPEA (diisopropylethylamine)
DMF (N,N-dimethylformamide)
DMSO (dimethylsulfoxide)
Et (ethyl)
EtOH (ethanol)
EtOAc (ethyl acetate)
FID (flame ionisation detection)
h (hour/hours)
HCl (Hydrochloric acid)
HEPES (4-(2-hydroxyethyl)-1-piperazineethanesulfonic acid)
HPLC (high performance liquid chromatography)
LCMS (liquid chromatography mass spectrometry)
LiHMDS (lithium hexamethyldisilazide)
MDAP (mass directed auto-preparative HPLC)
Me (methyl)
MeCN (acetonitrile)
MeOH (methanol)
min minute/minutes
MS (mass spectrum)
PdCl$_2$(dppf)-CH$_2$Cl$_2$ [1,1'-Bis(diphenylphosphino)ferrocene]dichloropalladium(II), complex with dichloromethane
Ph (phenyl)
$^i$Pr (isopropyl)
(R)-BINAP (R)-(+)-2,2'-Bis(diphenylphosphino)-1,1'-binaphthalene
[Rh(COD)Cl]$_2$ [chloro(1,5-cyclooctadiene)rhodium (I) dinner]
Si (Silica)
SFC (supercritical fluid chromatography)
SPE (solid phase extraction)
TBME (tert-butyl methyl ether)
TEA (triethylamine)
TFA (trifluoroacetic acid)
THF (tetrahydrofuran)
TLC (thin layer chromatography)

All references to brine refer to a saturated aqueous solution of sodium chloride.

Experimental Details $^1$H-NMR spectra were recorded at 400 MHz unless otherwise noted. Multiplicities indicated are: s=singlet, d=doublet, t=triplet, q=quartet, quint=quintet, sxt=sextet, m=multiplet, dd=doublet of doublets, dt=doublet of triplets, etc. and br indicates a broad signal.

Analytical LCMS

Analytical LCMS was conducted on one of the following Systems A to C.

The UV detection to all systems was an averaged signal from wavelength of 220 nm to 350 nm and mass spectra were recorded on a mass spectrometer using alternate-scan positive and negative mode electrospray ionization.

Experimental details of LCMS Systems A, B and C as referred to herein are as follows:

System A

Column: 50 mm×2.1 mm ID, 1.7 µm Acquity UPLC BEH $C_{18}$ column

Flow Rate: 1 mL/min.

Temp.: 40° C.

Solvents: A: 10 mM ammonium bicarbonate in water adjusted to pH10 with ammonia solution B: Acetonitrile

| Gradient: | Time (min) | A% | B% |
|---|---|---|---|
| | 0 | 99 | 1 |
| | 1.5 | 3 | 97 |
| | 1.9 | 3 | 97 |
| | 2.0 | 99 | 1 |

System B

Column: 50 mm×2.1 mm ID, 1.7 µm Acquity UPLC CSH C18 column

Flow Rate: 1 mL/min.

Temp.: 40° C.

Solvents: A: 10 mM ammonium bicarbonate in water adjusted to pH10 with ammonia solution B: Acetonitrile

| Gradient: | Time (min) | A% | B% |
|---|---|---|---|
| | 0 | 97 | 3 |
| | 0.05 | 97 | 3 |
| | 1.5 | 5 | 95 |
| | 1.9 | 5 | 95 |
| | 2.0 | 97 | 3 |

System C

Column: 50 mm×2.1 mm ID, 1.7 µm Acquity UPLC BEH C18 column

Flow Rate: 1.0 mL/min

Temp.: 40° C.

Solvents: A: 0.05% v/v solution of formic acid in water

B: 0.05% v/v solution of formic acid in acetonitrile

| Gradient: | Time (min) | A% | B% |
|---|---|---|---|
| | 0 | 97 | 3 |
| | 1.5 | 0 | 100 |
| | 1.9 | 0 | 100 |
| | 2.0 | 97 | 3 |

PREPARATION OF INTERMEDIATES

Intermediate 1: (R)-tert-Butyl 3-(2-(1,8-naphthyridin-2-yl)ethyl)pyrrolidine-1-carboxylate

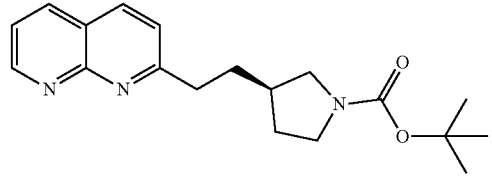 [SMILES: CC(C)(C)OC(=O)N1CC[C@@H](CCc2ccc3cccnc3n2)C1]

(R)-tert-Butyl 3-(2-(1,8-naphthyridin-2-yl)ethyl)pyrrolidine-1-carboxylate (40.09 g, 122 mmol) (WO2014/154725, page 31) was dissolved in THF (400 mL) at 20° C. The resulting mixture was treated with 4-methylbenzenesulfonic acid hydrate (23.29 g, 122 mmol) in THF (60 mL), which was added over 60 min and washed in with addition THF (20 mL). A slow precipitation of a purple solid, very small crystals, occurred during the addition. The resulting mixture was stirred at 18° C. for 3 h post addition before the resulting solid was collected by filtration and washed with THF (2×209 mL). The resulting wet cake was oven-dried over a weekend at 40° C. under vacuo. The dried solid (58.50 g) was slurried in water (580 mL) and TBME (580 mL) before the mixture was treated with sodium hydrogen carbonate (10.29 g, 122 mmol). The organic phase was washed with water (290 mL), and then passed through a 90 mm disc $R_{55}$SP Cuno cartridge (Lot 812411, Ref FD000058657, B0901) in a stainless steel housing, which had been primed with fresh TBME (150 mL) at a rate of 10 mL/min. Once all the solution had passed through the Cuno cartridge it was followed directly by a TBME line wash (150 mL). HPLC (Agilent Zorbax C18 column, 50 mm×3 mm, 1.7 µm) eluting with 0-95% (0.05% TFA in MeCN (B)—0.05% aqueous TFA (A)) over 2.5 min, followed by holding at 95%B for 0.2 min, and then holding at 0%B for the following 1.3 min): RT=1.90 min, 100%, column temperature 60° C., flow-rate=1.5 mL/min, detecting at 220 nm. $^{1}$H NMR (400 MHz, DMSO-$d_6$) δ 9.03 (1H, dd, J=4, 2 Hz), 8.43 (1H, dd, J 8, 2 Hz), 8.38 (1H, d, J 8.5 Hz), 7.58 (2H, m), 3.49-3.41 (1H, m), 3.39-3.30 (1H, m), 3.20-3.07 (1H, m), 3.01-2.95 (2H, m), 2.87-2.80 (1H, m), 2.22-1.93 (2H, m), 1.88 (2H, q, J 8 Hz), 1.58-1.43 (1H, m), 1.37 (9H, s).

Intermediate 2. (R)-tert-butyl 3-(2-(5,6,7,8-tetrahydro-1,8-naphthyridin-2-yl)ethyl)pyrrolidine-1-carboxylate

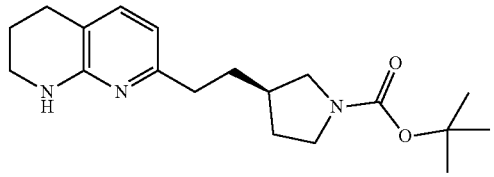 [SMILES: CC(C)(C)OC(=O)N1CC[C@@H](CCc2ccc3c(n2)NCCC3)C1]

A solution of (R)-tert-butyl 3-(2-(1,8-naphthyridin-2-yl)ethyl)pyrrolidine-1-carboxylate (Intermediate 1) (52 g, 159 mmol) in EtOAc (1500 mL) was hydrogenated over wet 5% Rh/C catalyst (wet, Degussa type, 32.7 g) at room temperature for 20 h. The catalyst was collected by filtration through Celite and the filtrate was concentrated in vacuo to give the title compound (52.6 g, 96%) as a brown oil: LCMS (System A) RT=1.25 min, 100%, ES+ve m/z 332 (M+H)⁺.

Intermediate 3. (R)-7-(2-(Pyrrolidin-3-yl)ethyl)-1,2,3,4-tetrahydro-1,8-naphthyridine

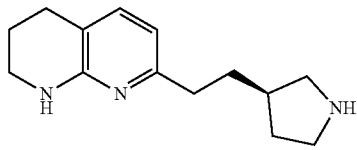 [SMILES: c1cc2c(nc1CC[C@@H]1CCNC1)NCCC2]

A solution of (R)-tert-butyl 3-(2-(5,6,7,8-tetrahydro-1,8-naphthyridin-2-yl)ethyl)pyrrolidine-1-carboxylate (Intermediate 2) (18.92 g, 57.1 mmol) in DCM (120 mL) in a cold water-bath was treated dropwise with 4M HCl in 1,4-dioxane (57.1 mL, 228 mmol) under nitrogen. Once addition was complete, the water bath was removed and the reaction mixture was stirred at room temperature overnight. The mixture was then concentrated in vacuo and the residue (15.5 g) was purified in several batches on SCX cartridges washing first with methanol and then eluting with 2M ammonia in methanol to give the title compound (8.94 g, 68%) as an orange oil: LCMS (System A) RT=0.70 min, 100%, ES+ve m/z 232 (M+H)⁺.

Intermediate 4. (R,E)-tert-Butyl 4-(3-(2-(5,6,7,8-tetrahydro-1,8-naphthyridin-2-yl)ethyl)pyrrolidin-1-yl)but-2-enoate

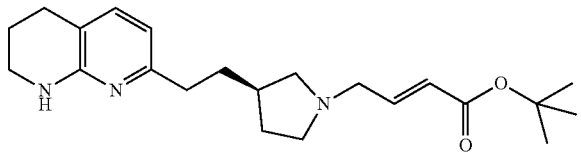 [SMILES: CC(C)(C)OC(=O)/C=C/CN1CC[C@@H](CCc2ccc3c(n2)NCCC3)C1]

A mixture of (R)-7-(2-(pyrrolidin-3-yl)ethyl)-1,2,3,4-tetrahydro-1,8-naphthyridine (Intermediate 3) (1.305 g, 5.64 mmol), (E)-tert-butyl 4-acetoxybut-2-enoate (WO20014154725) (1.13 g, 5.64 mmol), 1,1'-bis(diphenylphosphino)ferrocene]dichloropalladium(II) (0.207 g, 0.282 mmol) and DIPEA (2.96 mL, 16.92 mmol) in DCM (20 mL) were stirred for 3 h. The reaction mixture was partioned between ammonium chloride solution (50 mL) and DCM (50 mL). The aqueous layer was further extracted with DCM (50 mL). The combined organic layers were passed through a hydrophobic frit and concentrated in vacuo. The crude residue was purified by chromatography (KPNH, 110 g, 0-100% TBME-cyclohexane) eluting for 60 min. Product containing fractions were combined and concentrated to give the title compound (1.65 g, 79%) as a yellow oil (E:Z ratio 7.5:1). ¹H NMR δ (400 MHz, CDCl₃) 7.06 (d, J=7.3 Hz, 1H), 6.89 (dt, J=15.6, 6.2 Hz, 1H), 6.35 (d, J=7.3 Hz, 1H), 5.90 (dt, J=15.6, 1.6 Hz, 1H), 4.66-4.80 (m, 1H), 3.38-3.44 (m, 2H), 3.20 (ddd, J=6.2, 4.8, 1.8 Hz, 2H), 2.87 (dd, J=8.4, 7.4 Hz, 1H), 2.66-2.74 (m, 3H), 2.50-2.57 (m, J=8.2, 4.0, 4.0 Hz, 2H), 2.41-2.50 (m, J=8.7, 8.7, 6.0 Hz, 1H), 1.98-2.26 (m, J=8.6 Hz, 3H), 1.87-1.96 (m, J=11.7, 6.0, 6.0 Hz, 2H), 1.74 (q, J=7.6 Hz, 2H), 1.50 (s, 9H).

Intermediate 5. (S)-tert-Butyl 3-(3-(2-methoxyethoxy)phenyl)-4-((R)-3-(2-(5,6,7,8-tetrahydro-1,8-naphthyridin-2-yl)ethyl)pyrrolidin-1-yl)butanoate

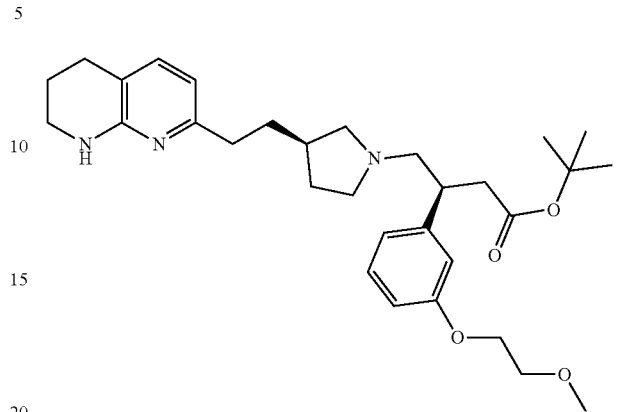

A mixture of (R,E)-tert-butyl 4-(3-(2-(5,6,7,8-tetrahydro-1,8-naphthyridin-2-yl)ethyl)pyrrolidin-1-yl)but-2-enoate (Intermediate 4) (4.36 g, 11.7 mmol), 2-(3-(2-methoxyethoxy)phenyl)-4,4,5,5-tetramethyl-1,3,2-dioxaborolane (available from Aldrich) (9.79 g, 35.2 mmol), aqueous KOH solution (6.18 mL, 23.5 mmol) were dissolved in 1,4-dioxane (50 mL). The flask was purged with nitrogen for 5 min and then (R)-BINAP (0.731 g, 1.17 mmol) and [Rh(COD)Cl]₂ (0.289 g, 0.587 mmol) were added. The reaction was heated to 90° C. for 2 h. After cooling, the solvent was removed in vacuo. The sample was re-dissolved in methanol and purified using a 100 g SCX cartridge, eluting with 1CV of MeOH and then 1CV of 2M ammonia in MeOH. The appropriate fractions were concentrated in vacuo to give a brown oil (4.8 g), which was separated by chiral HPLC on a Chiralcel OD-H Column (30 mm×25 cm), eluting with 40% EtOH-heptane, flow-rate 25 mL/min, detecting at 215 nm to give:
the major isomer: (S)-tert-butyl 3-(3-(2-methoxyethoxy)phenyl)-4-((R)-3-(2-(5,6,7,8-tetrahydro-1,8-naphthyridin-2-yl)ethyl)pyrrolidin-1-yl)butanoate (3.19 g, 52%): LCMS (System B) RT=1.45 min, 98%, ES+ve m/z 524 (M+H)⁺; Analytical Chiral HPLC on a Chiralcel OD-H Column (4.6 mm×250 mm) eluting with 50% EtOH-heptane RT=11.65 min, 99.5% and
the minor isomer: (R)-tert-butyl 3-(3-(2-methoxyethoxy)phenyl)-4-((R)-3-(2-(5,6,7,8-tetrahydro-1,8-naphthyridin-2-yl)ethyl)pyrrolidin-1-yl)butanoate (0.3 g, 5%): Analytical Chiral HPLC on a Chiralcel OD-H Column (4.6 mm×250 mm) eluting with 50% EtOH-heptane RT=8.1 min, 85%.

Intermediate 6. (R,E)-Methyl 4-(3-(2-(5,6,7,8-tetrahydro-1,8-naphthyridin-2-yl)ethyl)pyrrolidin-1-yl)but-2-enoate

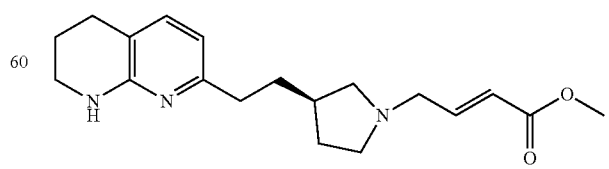

A solution of (R)-7-(2-(pyrrolidin-3-yl)ethyl)-1,2,3,4-tetrahydro-1,8-naphthyridine (Intermediate 3) (10.6 g, 45.8 mmol) in DCM (200 mL) was added DIPEA (14.40 mL, 82 mmol) under nitrogen. The reaction mixture was cooled to 0° C. and (E)-methyl 4-bromobut-2-enoate (5.39 mL, 45.8 mmol) was added dropwise. The reaction was stirred at room temperature for 3.75 h and then the reaction mixture was diluted with water (250 mL). The organic layer was separated and the aqueous layer was further extracted with DCM (2×100 mL). The combined organic fractions were dried (MgSO$_4$) and evapoarated in vacuo. The residue (13.94 g) was purified by chromatography on a silica cartridge (330 g) eluting with 0-100% EtOAc-(3:1 EtOAc-EtOH) containing 1% Et$_3$N. Appropriate fractions were combined and evaporated to give the title compound (7.66 g, 51%) as a yellow oil, which solidified on storage in the fridge. LCMS (System A) RT=1.02 min, 100%, ES+ve m/z 330 (M+H)$^+$.

Intermediate 7.
(R)-1-(3-Bromophenoxy)propan-2-ol

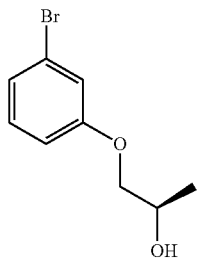

A stirred solution of 3-bromophenol (10 g, 57.8 mmol) in acetone (50 mL) was treated with (R)-2-methyloxirane (available from TCI) (16.79 g, 289 mmol) and K$_2$CO$_3$ (8.79 g, 63.6 mmol) at 0° C. in a sealed tube, and then the mixture was heated to 85° C. and stirred for 16 h. The reaction mixture was allowed to cool to room temperature and filtered. The filtrate was concentrated in vacuo, and the residue was partitioned between DCM (200 mL) and 1N aqueous NaOH solution (25 mL). The organic phase was washed with more NaOH (25 mL), water (50 mL), dried over Na$_2$SO$_4$, filtered and concentrated in vacuo to give the title compound (13 g, 94%) as a pale yellow liquid: MS ES+ve m/z 231, 233 (M+H)$^+$; Analytical chiral SFC on a YMC Amylose column (250 mm×4.6 mm) RT=2.42 min, 87%, CO$_2$, 20% co-solvent (0.5% diethylamine in methanol), 3 g/min, 100 Bar, 30° C., detecting at 225 nm.

Intermediate 8.
(R)-1-Bromo-3-(2-methoxypropoxy)benzene

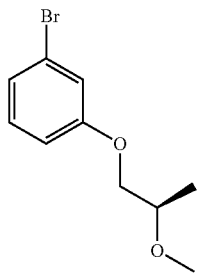

A stirred solution of (R)-1-(3-bromophenoxy)propan-2-ol (13 g, 56 mmol) in MeCN (130 mL) was treated with silver oxide (26.1 g, 113 mmol), followed by iodomethane (17.59 mL, 281 mmol) at 0° C. and the resulting mixture was stirred at 80° C. for 24 h in a sealed tube. The reaction mixture was cooled to room temperature, filtered, and the filtrate was concentrated in vacuo. The residue was diluted with DCM (10 mL), pre-adsorbed on to silica (60 g) and purified by column chromatography, eluting with 10% EtOAc in hexane. The corresponding fractions were collected and concentrated in vacuo to afford the title compound (9.5 g, 63%) as a pale yellow liquid: MS FID m/z 244, 246 (M$^+$).

Intermediate 9. (R)-2-(3-(2-methoxypropoxy)phenyl)-4,4,5,5-tetramethyl-1,3,2-dioxaborolane

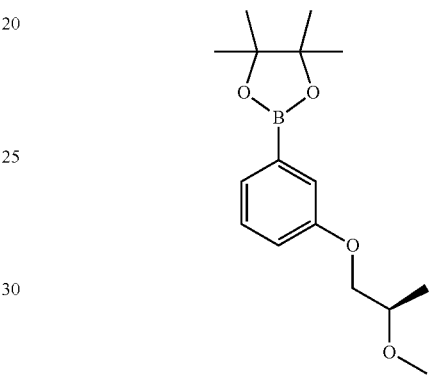

An argon degassed solution of (R)-1-bromo-3-(2-methoxypropoxy)benzene (Intermediate 8) (9.0 g, 36.7 mmol), bis(pinacolato)diboron (9.32 g, 36.7 mmol) in 1,4-dioxane (100 mL) was added potassium acetate (7.21 g, 73.4 mmol), followed by PdCl$_2$(dppf)-CH$_2$Cl$_2$ adduct (3.00 g, 3.67 mmol) and the resulting mixture was deoxygenated with argon for a further 20 min. The reaction mixture was heated and stirred at 90° C. for 16 h. The reaction mixture was filtered through celite and the filtrate was concentrated in vacuo. The residue was adsorbed on florisil and purified by chromatography eluting with 2% EtOAc—hexane to give the title compound (9 g, 73%) as a pale yellow liquid: MS FID m/z 292 (M$^+$).

Intermediate 10. Methyl 3-(3-((R)-2-methoxypropoxy)phenyl)-4-((R)-3-(2-(5,6,7,8-tetrahydro-1,8-naphthyridin-2-yl)ethyl)pyrrolidin-1-yl)butanoate

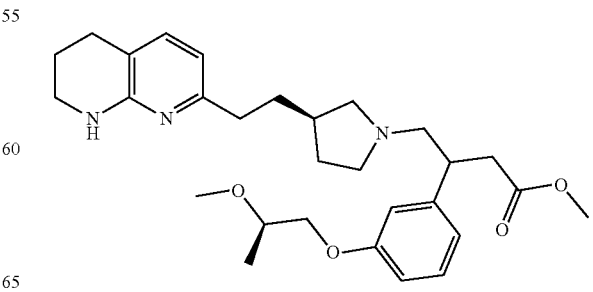

A stirred solution of (R,E)-methyl 4-(3-(2-(5,6,7,8-tetrahydro-1,8-naphthyridin-2-yl)ethyl)pyrrolidin-1-yl)but-2-enoate (Intermediate 6) (1.0 g, 3.0 mmol), (R)-2-(3-(2-methoxypropoxy)phenyl)-4,4,5,5-tetramethyl-1,3,2-dioxaborolane (Intermediate 9) (4.43 g, 15.2 mmol) and 3.8M aqueous KOH solution (2.4 mL, 9.1 mmol) in 1,4-dioxane (15 mL) was deoxygenated with argon for 25 min. In a separate vial a solution of (R)-BINAP (0.227 g, 0.364 mmol) and chloro(1,5-cyclooctadiene)rhodium(I) dimer (0.075 g, 0.15 mmol) in 1,4-dioxane (5 mL) was deoxygenated with argon for 20 min and then added to the above solution, and deoxygenation was continued for another 10 min. The resulting reddish reaction mixture was stirred at 90° C. for 18 h, cooled to room temperature, and filtered through Celite. The solid was washed with EtOAc (10 mL), and the filtrate and washings were concentrated in vacuo. The residue was diluted with DCM (10 mL), adsorbed on silica (20 g) and purified by chromatography eluting with 6% MeOH-DCM to give the title compound (800 mg, 50%) as a pale brown liquid: MS ES+ve m/z 496 (M+H)$^+$; Analytical chiral SFC on a Chiralcel OD-H column (250 mm×4.6 mm) RT=13.76 min, 80.1%, CO$_2$, 20% co-solvent (0.5% diethylamine in methanol), 3 g/min, 100 Bar, 30.2° C., detecting at 320 nm.

Intermediate 11.
(S)-1-(3-Bromophenoxy)propan-2-ol

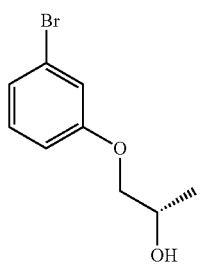

A stirred solution of 3-bromophenol (10 g, 57.8 mmol) in acetone (50 mL) was treated with (S)-2-methyloxirane (available from TCI) (20.47 mL, 289 mmol) and K$_2$CO$_3$ (8.79 g, 63.6 mmol) at 0° C. in a sealed tube, and then the mixture was heated to 85° C. and stirred for 16 h. The reaction mixture was allowed to cool to room temperature and filtered. The filtrate was concentrated in vacuo, and the residue was partitioned between DCM (10 mL) and water (10 mL). The organic phase was washed with water (10 mL), dried over Na$_2$SO$_4$, filtered and concentrated in vacuo to give the title compound (11 g, 72%) as a yellow oil: $^1$H NMR (CDCl$_3$, 400 MHz) δ 7.18-7.07 (m, 3H), 6.89-6.84 (m, 1H), 4.24-4.15 (m, 1H), 3.93 (dd, J=3, 9 Hz, 1H), 3.80 (dd, J=7.5, 9 Hz, 1H), 1.31-1.26 (m, 3H).

Intermediate 12.
(S)-1-Bromo-3-(2-methoxypropoxy)benzene

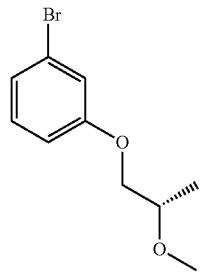

A stirred solution of (S)-1-(3-bromophenoxy)propan-2-ol (Intermediate 11) (11 g, 47.6 mmol) in MeCN (110 mL) was added silver oxide (11.03 g, 47.6 mmol), followed by iodomethane (14.88 mL, 238 mmol) at 0° C. and stirred at 80° C. for 24 h in a sealed tube. The reaction mixture was cooled to room temperature, filtered, and the filtrate was concentrated in vacuo. The residue was diluted with DCM (10 mL), adsorbed on to silica (60 g) and purified by column chromatography, eluting with 10% EtOAc in hexane. The corresponding fractions were collected and concentrated in vacuo to afford the title compound (7 g, 54%) as pale yellow liquid: MS FID m/z 244, 246 (M$^+$). Analytical Chiral HPLC on a Chiralpak AD-H column (250 mm×4.6 mm) RT=6.07 min, 87%, eluting with 5% EtOH in hexane, flow rate=1 mL/min, detecting at 210 nm.

Intermediate 13. (S)-2-(3-(2-Methoxypropoxy)phenyl)-4,4,5,5-tetramethyl-1,3,2-dioxaborolane An argon deoxygenated solution of (S)-1-bromo-3-(2-methoxypropoxy)benzene (Intermediate 12) (5.0 g, 20.4 mmol), potassium acetate (4.00 g, 40.8 mmol) and bis(pinacolato)diboron (5.70 g, 22.4 mmol) in 1,4-dioxane (100 mL) was added PdCl$_2$(dppf)-CH$_2$Cl$_2$ adduct (1.666 g, 2.40 mmol) and the resulting mixture was deoxygenated with argon for a further 20 min. The reaction mixture was heated and stirred at 90° C. for 16 h. The reaction mixture was filtered through Celite and the filtrate was concentrated in vacuo. The residue was adsorbed on silica and purified by silica column chromatography, eluting with 5% EtOAc in hexane. The corresponding fractions were collected and concentrated in vacuo to afford the title compound (3 g, 45%) as a pale yellow liquid: MS FID m/z 292 (M$^+$).

Intermediate 14. (S)-Methyl 3-(3-((S)-2-methoxypropoxy)phenyl)-4-((R)-3-(2-(5,6,7,8-tetrahydro-1,8-naphthyridin-2-yl)ethyl)pyrrolidin-1-yl)butanoate

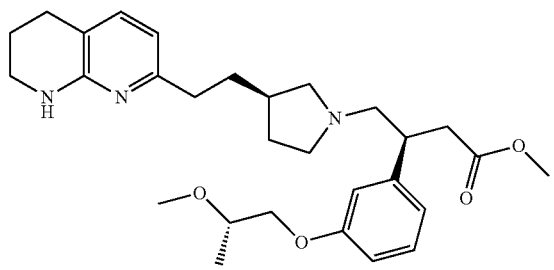 [SMILES: COC(=O)C[C@H](CN1CC[C@@H](CCc2ccc3c(n2)NCCC3)C1)c1cccc(OC[C@H](C)OC)c1]

A mixture of (R,E)-methyl 4-(3-(2-(5,6,7,8-tetrahydro-1,8-naphthyridin-2-yl)ethyl)pyrrolidin-1-yl)but-2-enoate (Intermediate 6) (500 mg, 1.52 mmol), aqueous 3.8M solution of KOH (1.997 mL, 7.59 mmol) and (S)-2-(3-(2-methoxypropoxy)phenyl)-4,4,5,5-tetramethyl-1,3,2-dioxaborolane (Intermediate) (2.21 g, 7.59 mmol) in 1,4-dioxane (20 mL) was deoxygenated with argon for 25 min whilst in a separate vial (R)-BINAP (113 mg, 0.182 mmol) and chloro(1,5-cyclooctadiene)rhodium(I) dimer (37.4 mg, 0.076 mmol) in 1,4-dioxane (20 mL) were deoxygenated with argon for 20 min and then added to the above solution with degassing with argon for another 10 min and then the solution was heatd to 90° C. for 16 h. The reaction mixture was concentrated in vacuo, the residue was dissolved in DCM (50 mL), adsorbed on to silica gel (10 g) and purified by column chromatography eluting with 6% MeOH-DCM. Appropriate fractions were combined and evaporated in vacuo to give the product (100 mg, 13%) as a mixture of diastereoisomers. The mixture was separated by preparative chiral SFC on a Chiralcel AD-H column (250 mm×21 mm), CO$_2$, 40% co-solvent (0.5% diethylamine in methanol), 60 g/min, 100 Bar, 30.2° C., detecting at 321 nm to give:
the major isomer: (40 mg, 5%) (S)-methyl 3-(3-((S)-2-methoxypropoxy)phenyl)-4-((R)-3-(2-(5,6,7,8-tetrahydro-1,8-naphthyridin-2-yl)ethyl)pyrrolidin-1-yl)butanoate (40 mg, 5%) MS ES+ve m/z 496 (M+H)$^+$; Analytical chiral SFC on a Chiralcel OD-H column (250 mm×4.6 mm) RT=2.72 min, 97.8%, CO$_2$, 50% co-solvent (0.5% diethylamine in methanol), 4 g/min, 100 Bar, 30° C., detecting at 324 nm and
the minor isomer: (20 mg, 2.5%) (R)-methyl 3-(3-((S)-2-methoxypropoxy)phenyl)-4-((R)-3-(2-(5,6,7,8-tetrahydro-1,8-naphthyridin-2-yl)ethyl)pyrrolidin-1-yl)butanoate (20 mg, 2%). Analytical chiral SFC on a Chiralcel OD-H column (250 mm×4.6 mm) RT=2.03 min, 99.3%, CO$_2$, 50% co-solvent (0.5% diethylamine in methanol), 4 g/min, 100 Bar, 30° C., detecting at 322 nm.

Intermediate 15. 1-(3-Bromophenoxy)-2-methylpropan-2-ol

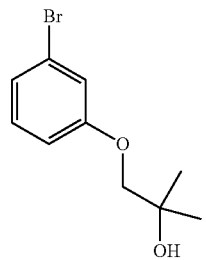

To a stirred solution of 3-bromophenol (5 g, 28.9 mmol) in acetone (50 mL) was added 2,2-dimethyloxirane(10.04 mL, 116 mmol) and K$_2$CO$_3$ (4.39 g, 31.8 mmol) at 0° C. in a sealed tube. The resulting mixture was heated to reflux and stirred for 16 h. The reaction mixture was filtered and the filtrate was concentrated under reduced pressure. The residue was diluted with DCM (100 mL) and washed with aq. 1N NaOH solution (2×50 mL), the organic layer was washed with brine solution (50 mL), dried over Na$_2$SO$_4$, filtered and concentrated to obtain the title compound (6 g, 80%) as a pale yellow liquid: MS FID m/z 244, 246 (M$^+$).

Intermediate 16. 1-bromo-3-(2-methoxy-2-methylpropoxy)benzene

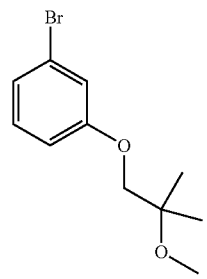

To a stirred solution of 1-(3-bromophenoxy)-2-methylpropan-2-ol (Intermediate 15) (5 g, 20.4 mmol) in MeCN (50 mL) was added silver oxide (4.73 g, 20.4 mmol), followed by iodomethane (6.38 mL, 102 mmol) at 0° C. and the resulting mixture was stirred at 80° C. for 16 h in a sealed tube. The reaction mixture was filtered and the solid was washed with EtOAc (20 mL), the filtrate was concentrated in vacuo. The residue was purified by column chromatography on silica gel (100-200 mesh) eluting with 5% EtOAc in hexane. The fractions were concentrated in vacuo to afford the title compound (2.5 g, 46%) as a colourless oil: NMR (CDCl$_3$, 400 MHz) δ 7.16-7.05 (3H, m), 6.87 (1H, m), 3.80 (2H, s), 3.29 (3H, s), 1.29 (6H, s).

Intermediate 17. 2-(3-(2-Methoxy-2-methylpropoxy)phenyl)-4,4,5,5-tetramethyl-1,3,2-dioxaborolane

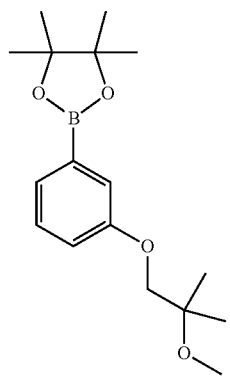 [SMILES: COC(C)(C)COc1cccc(B2OC(C)(C)C(C)(C)O2)c1]

To a stirred solution of 1-bromo-3-(2-methoxy-2-methylpropoxy)benzene (Intermediate 16) (2.4 g, 9.26 mmol) in 1,4-dioxane (30 mL) was added potassium acetate (1.82 g, 18.5 mmol) and 4,4,4',4',5,5,5',5'-octamethyl-2,2'-bi(1,3,2-dioxaborolane) (2.35 g, 9.26 mmol) and this was purged with nitrogen gas for 15 min then PdCl$_2$(dppf)-CH$_2$Cl$_2$ adduct (0.756 g, 0.926 mmol) was added and the reaction mixture was heated to 90° C. for 16 h. The reaction mixture was concentrated under reduced pressure and the residue was dissolved in DCM (15 mL) and adsorbed on silica gel (25 g) and purified by column chromatography, eluting with 10% EtOAc and petroleum ether (200 mL). The fractions were concentrated under reduced pressure to give the title compound (1.6 g, 50%) as a pale brown liquid: MS FID m/z 306 (M+).

Intermediate 18. Methyl 3-(3-(2-methoxy-2-methyl-propoxy)phenyl)-4-((R)-3-(2-(5,6,7,8-tetrahydro-1,8-naphthyridin-2-yl)ethyl)pyrrolidin-1-yl)butanoate

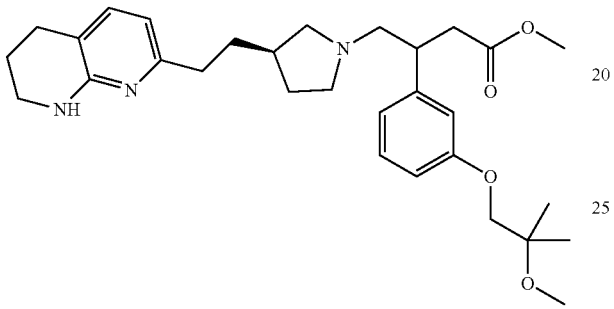

A stirred solution of (R,E)-methyl 4-(3-(2-(5,6,7,8-tetrahydro-1,8-naphthyridin-2-yl)ethyl)pyrrolidin-1-yl)but-2-enoate (Intermediate 6) (0.5 g, 1.518 mmol), 3M KOH (1.518 mL, 4.55 mmol) and 2-(3-(2-methoxy-2-methyl-propoxy)phenyl)-4,4,5,5-tetramethyl-1,3,2-dioxaborolane (Intermediate 17) (1.39 g, 4.55 mmol) in 1,4-dioxane (30 mL) was deoxygenated with argon for 25 min and in a separate vial (R)-BINAP (0.113 g, 0.182 mmol) and chloro(1,5-cyclooctadiene)rhodium(I) dimer (37 mg, 0.076 mmol) in dioxane were degassed with argon for 20 min and then added to the above solution and again degassed with argon for 10 min, and the mixture was stirred at 90° C. for 16 h. The reaction mixture was concentrated in vacuo, the residue was diluted with DCM (10 mL) and adsorbed on to silica gel (5 g) and purified by column chromatography eluting with 6% MeOH in DCM. The fractions were concentrated in vacuo to afford the title compound (160 mg, 20%) as a brown gum: MS ES+ve m/z 510 (M+H)+; Analytical chiral SFC on a Chiralcel OD-H column (250 mm×4.6 mm) RT=2.68 min, 84%, and RT=2.44 min, 12%, CO$_2$, 35% co-solvent (0.5% diethylamine in MeOH), 3 g/min, 100 Bar, 30.2° C., detecting at 322 nm.

Intermediate 19. (R)-1-Methoxypropan-2-yl 4-methylbenzenesulfonate

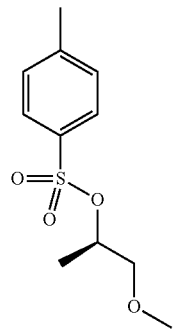 [SMILES: COC[C@@H](C)OS(=O)(=O)c1ccc(C)cc1]

To a solution of (R)-1-methoxypropan-2-ol (available from Combi-block) (5 g, 55 mmol) in DCM (50 mL) and pyridine (25 mL) was added 4-methylbenzenesulfonyl chloride (11.6 g, 61 mmol) and the reaction mixture was stirred at room temperature for 16 h. Ice (100 g) was added and the mixture was stirred for 1 h. The organic phase was separated and washed with 10% aq. H$_2$SO$_4$ (4×25 mL), water (30 mL), dried (Na$_2$SO$_4$), and then filtered through silica eluting with DCM (100 mL). The filtrate was concentrated under reduced pressure to give the title compound (7 g, 51%) as a colourless liquid: MS ES+ve m/z 245 (M+H)+; [α]D$^{25}$ −2° (c=1 in CHCl$_3$).

Intermediate 20. (S)-1-Bromo-3-((1-methoxypropan-2-yl)oxy)benzene

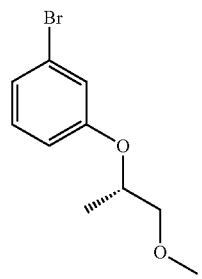

To a solution of 3-bromophenol (3.06 g, 17.7 mmol) in DMF (50 mL) was added potassium tert-butoxide (2.48 g, 22.1 mmol). This was cooled to 0° C. then (R)-1-methoxypropan-2-yl 4-methylbenzenesulfonate (Intermediate 19) (5.4 g, 22 mmol) was added and stirred at room temperature for 16 h. MeOH (1.8 mL) was added and the mixture was stirred for 4 h. Water (75 mL) was added and the mixture was stirred for 10 min. The mixture was extracted with petroleum ether (2×250 mL) and the combined organic solutions were washed with water (50 mL), dried (Na$_2$SO$_4$), filtered and concentrated under reduced pressure. The residue was dissolved in DCM (10 mL) adsorbed onto silica (5 g) and purified by chromatography eluting with 3% EtOAc-petroleum ether. The fractions were concentrated under reduced pressure to give the title compound (2.5 g, 46%) as a colourless liquid: MS ES+ve m/z 245, 247 (M+H)+.

Intermediate 21. (S)-2-(3-((1-Methoxypropan-2-yl)oxy)phenyl)-4,4,5,5-tetramethyl-1,3,2-dioxaborolane

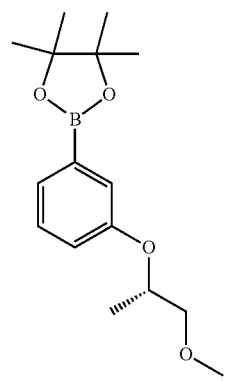

To a degassed solution of (S)-1-bromo-3-((1-methoxypropan-2-yl)oxy)benzene (Intermediate 20) (2.5 g, 10 mmol) in 1,4-dioxane (30 mL) was added KOAc (3.00 g, 30.6 mmol), 4,4,4',4',5,5,5',5'-octannethyl-2,2'-bi(1,3,2-dioxaborolane) (3.37 g, 13.26 mmol) and PdCl$_2$(dppf)-CH$_2$Cl$_2$ adduct (833 mg, 1.02 mmol) and the mixture was heated for 12 h at 90° C. The reaction mixture was cooled, diluted with EtOAc, filtered through a Celite pad, and the filtrate was concentrated under reduced pressure. The residue was adsorbed onto silica (1 g) and purified by chromatography on silica (10 g) eluting with 5% EtOAc-hexane to give the title compound (1.5 g, 43%) MS FID m/z 292 (M$^+$).

Intermediate 22. Methyl 3-(3-a(S)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoate

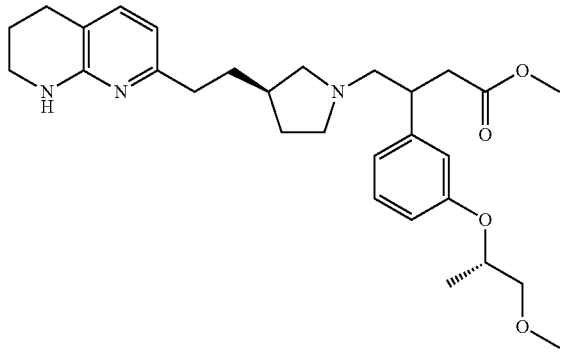 [SMILES: COC[C@H](C)Oc1cccc(C(CC(=O)OC)CN2CC[C@@H](CCc3ccc4c(n3)NCCC4)C2)c1]

A stirred solution of (R,E)-methyl 4-(3-(2-(5,6,7,8-tetrahydro-1,8-naphthyridin-2-yl)ethyl)pyrrolidin-1-yl)but-2-enoate (Intermediate 6) (300 mg, 0.911 mmol), (S)-2-(3-((1-methoxypropan-2-yl)oxy)phenyl)-4,4,5,5-tetramethyl-1,3,2-dioxaborolane (Intermediate 21) (798 mg, 2.73 mmol) in 1,4-dioxane (20 mL) was degassed with argon for 25 min. In a separate vial (R)-BINAP (68.0 mg, 0.11 mmol) and chloro(1,5-cyclooctadiene)rhodium(I) dimer (22 mg, 0.046 mmol) in 1,4-dioxane (15 mL) were degassed with argon for 20 min and then added to the above solution, degassing with argon continued for another 10 min. The resulting reddish reaction mixture was heated at 90° C. for 18 h, and then was filtered through a Celite bed, washed with 1,4 dioxane (30 mL), and the filtrate was concentrated in vacuo. The residue was dissolved in DCM (15 mL), adsorbed onto silica (3 g), and purified by chromatography on silica eluting with a gradient of 6-10% MeOH-DCM. The fractions were evaporated in vacuo to give the title compound (112 mg, 21%) as a light brown gum: MS ES+ve m/z 496 (M+H)$^+$.

Intermediate 23. (R)-3-(3-Bromophenoxy)tetrahydrofuran

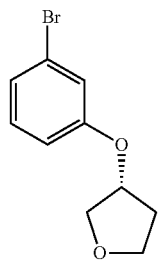 [SMILES: Brc1cccc(O[C@@H]2CCOC2)c1]

A solution of 3-bromophenol (10 g, 57.8 mmol), triphenylphosphine (22.74 g, 87 mmol), (S)-tetrahydrofuran-3-ol (available from Combi Blocks) (5.09 g, 57.8 mmol) in THF (100 mL) was treated at 0° C. with DIAD (11.24 mL, 57.8 mmol) and then the mixture was stirred at 25° C. for 16 h. The solvent was removed in vacuo and the residue was adsorbed on silica (50 g) and purified by column chromatography on silica eluting with 10% EtOAc-hexane. The fractions were concentrated in vacuo to give the title compound (8 g, 52%) as a colourless liquid: MS ES+ve m/z 243, 245 (M+H)$^+$; Analytical chiral SFC on a Chiralcel OJ-H column (250 mm×4.6 mm) RT=2.24 min, 98%, CO$_2$, 30% co-solvent (0.5% diethylamine in MeOH), 3 g/min, 100 Bar, 29.9° C., detecting at 272 nm.

Intermediate 24. (R)-4,4,5,5-tetramethyl-2-(3-((tetrahydrofuran-3-yl)oxy)phenyl)-1,3,2-dioxaborolane

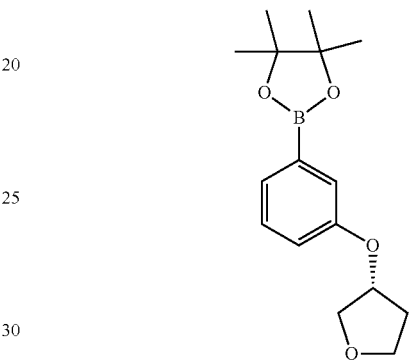

A solution of (R)-3-(3-bromophenoxy)tetrahydrofuran (Intermediate 23) (8 g, 33 mmol), potassium acetate (6.46 g, 65.8 mmol) and bis(pinacolato)diboron (9.19 g, 36.2 mmol) in 1,4-dioxane (80 mL) was deoxygenated with argon gas and then treated with PdCl$_2$(dppf)-CH$_2$Cl$_2$ adduct (1.34 g, 1.64 mmol). The solution was deoxygenated for a further 15 min by passing argon gas through the reaction mixture and then heated to 90° C. for 16 h. The reaction mixture was cooled to room temperature, filtered through a Celite pad and washed with 1,4-dioxane (10 mL). The filtrate and washings were combined and evaporated in vacuo. The residue was adsorbed onto silica (20 g) and purified by column chromatography on silica eluting with 10% EtOAc-hexane. The fractions were concentrated in vacuo to give the title compound (6 g, 54%) as a pale yellow liquid: MS FID 290 (M$^+$).

Intermediate 25. Methyl 4-((R)-3-(2-(5,6,7,8-tetrahydro-1,8-naphthyridin-2-yl)ethyl)pyrrolidin-1-yl)-3-(3-MS)-tetrahydrofuran-3-yl)oxy)phenyl)butanoate

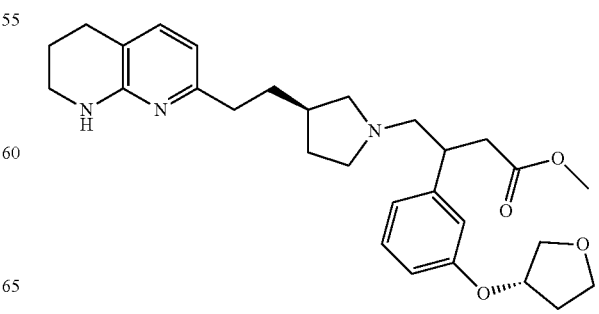

A solution of of (R,E)-methyl 4-(3-(2-(5,6,7,8-tetrahydro-1,8-naphthyridin-2-yl)ethyl)pyrrolidin-1-yl)but-2-enoate (Intermediate 6) (500 mg, 1.52 mmol), 3.8 M KOH (1.52 mL, 5.77 mmol), (R)-4,4,5,5-tetramethyl-2-(3-((tetrahydrofuran-3-yl)oxy)phenyl)-1,3,2-dioxaborolane (Intermediate 24) (2.20 g, 7.59 mmol) in 1,4-dioxane (20 mL) was deoxygenated by passing argon gas through the solution for 25 min. In a separate vial (R)-BINAP (113 mg, 0.182 mmol) and chloro(1,5-cyclooctadiene)rhodium (I) dimer (37.4 mg, 0.076 mmol) in 1,4-dioxane (20 mL) was deoxygenated by passing argon gas through the solution for 20 min. The two solutions were mixed and further deoxygenated with argon for another 10 min, and then heated to 90° C. for 16 h. The solvent was removed in vacuo and the residue was adsorbed onto silica (10 g) and purified by column chromatography on silica eluting with 6% MeOH-DCM. The fractions were evaporated in vacuo to give the title compound (200 mg, 25%) as a diasteroisomeric mixture: MS ES+ve m/z 494 (M+H)$^+$; Analytical chiral SFC on a Chiralcel OD-H column (250 mm×4.6 mm) RT=2.83 min, 78%, and RT=2.39 min, 10%, CO$_2$, 40% co-solvent (0.5% diethylamine in MeOH), 4 g/min, 100 Bar, 30° C., detecting at 210 nm.

Intermediate 26.
(S)-3-(3-Bromophenoxy)tetrahydrofuran

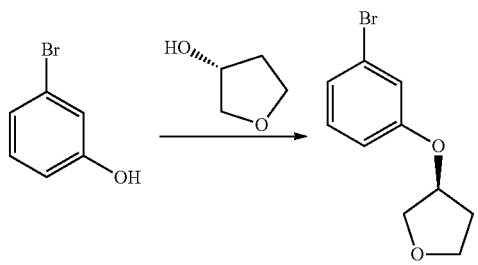

To a stirred solution of 3-bromophenol (10 g, 57.8 mmol), triphenylphosphine (22.74 g, 87 mmol), (R)-tetrahydrofuran-3-ol (5.09 g, 57.8 mmol) (available from Combi Blocks) in THF (100 mL) was added DIAD (11.24 mL, 57.8 mmol) at 0° C. and the resulting mixture was stirred at 25° C. for 16 h. The solvents were removed in vacuo, the residue was adsorbed onto silica (50 g) and purified by silica chromatography eluting with 10% EtOAc-hexane. The corresponding fractions were concentrated in vacuo and re-dissolved in DCM (100 mL), washed with 1M aqueous NaOH solution (2×25 mL) and water (50 mL), dried (Na$_2$SO$_4$) and concentrated in vacuo to afford the title compound (8 g, 56%) as a clear colourless liquid: [α]$_D^{25}$=+12° (c=1.0 in CHCl$_3$); Analytical chiral SFC on a YMC Amylose column (250 mm×4.6 mm) RT=2.82 min, 96%, CO$_2$, 25% co-solvent (0.5% diethylamine in MeOH), 3 g/min, 100 Bar, 30° C., detecting at 212 nm.

Intermediate 27. (S)-4,4,5,5-Tetramethyl-2-(3-((tetrahydrofuran-3-yl)oxy)phenyl)-1,3,2-dioxaborolane

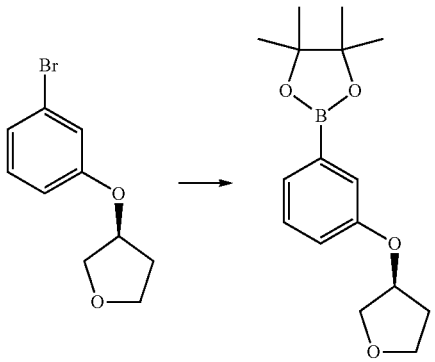 [SMILES: Brc1cccc(O[C@H]2CCOC2)c1 ; CC1(C)OB(c2cccc(O[C@H]3CCOC3)c2)OC1(C)C]

A solution of (S)-3-(3-bromophenoxy)tetrahydrofuran (Intermediate 26) (8 g, 33 mmol), potassium acetate (6.46 g, 65.8 mmol) and bis(pinacolato)diboron (9.19 g, 36.2 mmol) in 1,4-dioxane (80 mL) was deoxyganated with argon gas, treated with PdCl$_2$(dppf)-CH$_2$Cl$_2$ adduct (2.69 g, 3.29 mmol) at room temperature and the resulting mixture was deoxygenated with argon for a further 15 min. The reaction mixture was stirred at 90° C. for 16 h, cooled to room temperature and filtered through Celite. The solid was washed with 1,4-dioxane (10 mL). The filtrate washings were concentrated in vacuo, the residue was adsorbed on to silica (20 g) and purified by silica column chromatography eluting with 10% EtOAc-hexane. The corresponding fractions were collected and concentrated in vacuo to afford the title compound (6 g, 36%) as pale brown liquid: MS ES+ve m/z 291 (M+H)$^+$.

Intermediate 28. Methyl 4-((R)-3-(2-(5,6,7,8-tetrahydro-1,8-naphthyridin-2-yl)ethyl)pyrrolidin-1-yl)-3-(3-(((R)-tetrahydrofuran-3-yl)oxy)phenyl)butanoate

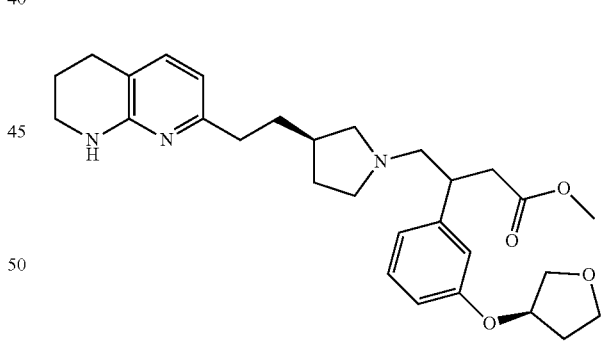

A solution of (R,E)-methyl 4-(3-(2-(5,6,7,8-tetrahydro-1,8-naphthyridin-2-yl)ethyl)pyrrolidin-1-yl)but-2-enoate (Intermediate 6) (500 mg, 1.518 mmol), (S)-4,4,5,5-tetramethyl-2-(3-((tetrahydrofuran-3-yl)oxy)phenyl)-1,3,2-dioxaborolane (Intermediate 27) (2.2 g, 7.59 mmol), 3.8 M aqueous KOH (1.997 mL, 7.59 mmol) in 1,4-dioxane (20 mL) was deoxygenated with argon gas for 25 min. In a separate vial (R)-BINAP (113 mg, 0.182 mmol) and chloro (1,5-cyclooctadiene)rhodium(I) dimer (37.4 mg, 0.076 mmol) in 1,4-dioxane (20 mL) were deoxygenated with argon for 20 min. The two solutions were mixed and further deoxygenated with argon for another 10 min, and then heated to 90° C. for 16 h. The solvent was removed in vacuo and the residue was adsorbed onto silica (10 g) and purified by column chromatography, eluting with 6% MeOH in DCM. The fractions were concentrated under vacuum to afford the title compound (250 mg, 29%) as a diasteroisomeric mixture: MS ES+ve m/z 494 (M+H)+; Analytical chiral SFC on a Chiralcel OD-H column (250 mm×4.6 mm) RT=2.42 min, 73%, and RT=2.08 min, 9%, $CO_2$, 50% co-solvent (0.5% diethylamine in MeOH), 4 g/min, 100 Bar, 30° C., detecting at 210 nm.

Intermediate 29.
1-Bromo-3,5-bis(2-methoxyethoxy)benzene

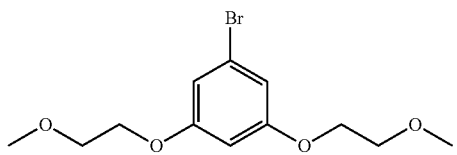

A solution of 5-bromobenzene-1,3-diol (2 g, 10.6 mmol) in DMF (20 mL) was treated with $K_2CO_3$ (5.85 g, 42.3 mmol) and 1-bromo-2-methoxyethane (3.24 g, 23.3 mmol) and the reaction mixture was stirred under nitrogen at room temperature for 12 h. The reaction mixture was partitioned between EtOAc (50 mL) and water (30 mL) and washed with brine solution (30 mL). The organic layer was dried ($Na_2SO_4$), filtered and concentrated under reduced pressure. The residue was adsorbed onto silica and purified by column chromatography on silica (20 g) eluting with 20% EtOAc-petroleum ether. The fractions were concentrated under reduced pressure to afford the title compound (2.0 g, 58%) as a colourless liquid: MS ES+ve m/z 305, 307 (M+H)+.

Intermediate 30. 2-(3,5-Bis(2-methoxyethoxy)phenyl)-4,4,5,5-tetramethyl-1,3,2-dioxaborolane

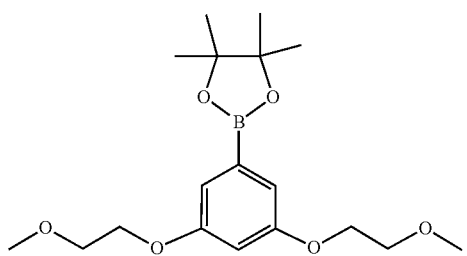

A solution of 1-bromo-3,5-bis(2-methoxyethoxy)benzene (Intermediate 29) (3.0 g, 9.8 mmol) and 4,4,4',4',5,5,5',5'-octamethyl-2,2'-bi(1,3,2-dioxaborolane) (3.00 g, 11.8 mmol), potassium acetate (2.89 g, 29.5 mmol) in 1,4-dioxane (30 mL) was deoxygenated with nitrogen gas for 15 min. $PdCl_2(dppf)$-$CH_2Cl_2$ adduct (1.606 g, 1.966 mmol) was added and the reaction mixture was heated at 100° C. overnight. The solvent was removed in vacuo and the residue was purified by column chromatography on silica (50 g), eluting with 30% EtOAc in hexane to afford the title compound (3.5 g, 96%) as a pale yellow liquid: MS ES+ve m/z 353 (M+H)+.

Intermediate 31. Methyl 3-(3,5-bis(2-methoxyethoxy)phenyl)-4-((R)-3-(2-(5,6,7,8-tetrahydro-1,8-naphthyridin-2-yl)ethyl)pyrrolidin-1-yl)butanoate

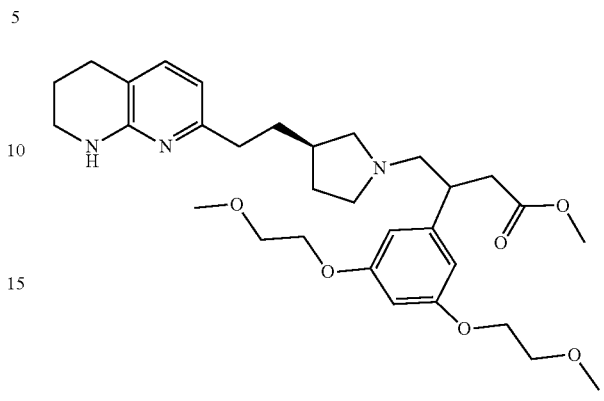

A solution of (R,E)-methyl 4-(3-(2-(5,6,7,8-tetrahydro-1,8-naphthyridin-2-yl)ethyl)pyrrolidin-1-yl)but-2-enoate (Intermediate 6) (300 mg, 0.911 mmol), 2-(3,5-bis(2-methoxyethoxy)phenyl)-4,4,5,5-tetramethyl-1,3,2-dioxaborolane (Intermediate 30) (962 mg, 2.73 mmol) and 3.8M aq. KOH solution (0.719 mL, 2.73 mmol) in 1,4-dioxane (6 mL) was deoxygenated with argon gas. Chloro(1,5-cyclooctadiene) rhodium (I) dimer (22.45 mg, 0.046 mmol) and (R)-BINAP (68.0 mg, 0.109 mmol) in 1,4-dioxane (4 mL) were added and the solution was deoxygenated for 10 min. The reaction mixture was heated to 90° C. for 3 h. The solvent was removed in vacuo and the residue (500 mg) was adsorbed onto silica (3 g) and purified by column chromatography on silica (12 g) eluting with 7% MeOH-DCM. The fractions were concentrated under reduced pressure and the residue (250 mg) was dissolved in DCM (1 mL) and further purified by preparative TLC on silica GF254 (mobile phase 5% MeOH-DCM). The compound was washed with 10% MeOH-DCM and the filtrate evaporated in vacuo to give the title compound (150 mg, 28%) as a brown gum: MS ES+ve m/z 556 (M+H)+; Analytical chiral SFC on a Chiralpak AS-H column (250 mm×4.6 mm) RT=2.31 min, 82%, and RT=3.09 min, 18%, $CO_2$, 20% co-solvent (0.5% diethylamine in MeOH), 3 g/min, 100 Bar, 30° C., detecting at 321 nm.

Intermediate 32.
(3-(Tetrahydrofuran-3-yl)phenyl)boronic acid

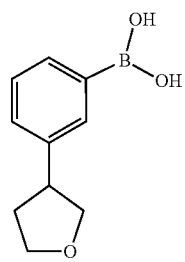 [SMILES: OB(O)c1cccc(C2CCOC2)c1]

To a stirred solution of 3-(3-iodophenyl)tetrahydrofuran (PR Guzzo et al US20120184531AA, page 52) (13 g, 47.4 mmol), triisopropylborate (17.62 mL, 76 mmol) in THF (150 mL) was added "BuLi (24.66 mL, 61.7 mmol) dropwise for 5 min at −78° C. After the addition was complete the reaction mixture was warmed to room temperature and stirred for 3 h. The reaction was quenched with 2M HCl (100 mL) and water (200 mL), EtOAc (250 mL) were added. The organic layer was separated and the aqueous layer was re-extracted with EtOAc (2×200 mL). The combined organic solutions were dried (Na₂SO₄), filtered, and concentrated under reduced pressure. The residue (10 g) was absorbed onto silica (20 g) and purified by column chromatography on silica gel (150 g), eluting with 0-50% EtOAc in petroleum ether. The fractions were combined and concentrated under reduced pressure, the residue (5 g) was washed with cold pentane (100 mL) to afford the title compound (4.2 g, 45%) as a brown gum: MS ES+ve m/z 193 (M+H)⁺.

Intermediate 33. (3S)-Methyl 4-((R)-3-(2-(5,6,7,8-tetrahydro-1,8-naphthyridin-2-yl)ethyl)pyrrolidin-1-yl)-3-(3-(tetrahydrofuran-3-yl)phenyl)butanoate Isomer 1 and Isomer 2

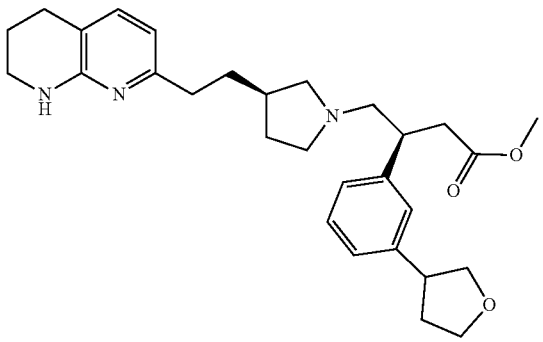 [SMILES: COC(=O)C[C@H](CN1CC[C@@H](CCc2ccc3c(n2)NCCC3)C1)c1cccc(C2CCOC2)c1]

An aqueous 3.8M KOH solution (1.198 mL, 4.55 mmol) was added to a mixture of (R,E)-methyl 4-(3-(2-(5,6,7,8-tetrahydro-1,8-naphthyridin-2-yl)ethyl)pyrrolidin-1-yl)but-2-enoate (Intermediate 6) (1 g, 3.04 mmol), (3-(tetrahydrofuran-3-yl)phenyl)boronic acid (Intermediate 32) (874 mg, 4.55 mmol), (R)-BINAP (0.378 g, 0.607 mmol) and chloro (1,5-cyclooctadiene)rhodium(I) dimer (0.150 g, 0.304 mmol) in 1,4-dioxane (10 mL). The mixture was stirred at 50° C. for 2 h, cooled and then partitioned between EtOAc (100 mL) and water (50 mL). The phases were separated and the organic phase was washed with brine (50 mL), dried (MgSO₄), filtered and evaporated in vacuo. The crude product was purified by column chromatography on silica gel KP-NH (100 g), eluting with 0-50% EtOAc-cyclohexane over 60 min to give crude product (900 mg) as a mixture of four diastereoisomers. This material was dissolved in EtOH (9 mL) and purified by HPLC on a Chiralcel OD-H column (30 mm×250 mm), eluting with 10% EtOH (containing 0.2%isopropylamine)-heptane (containing 0.2%isopropylamine), flow-rate=30 mL/min, detecting at 215 nm. This purification step removed impurities and the minor diastereoisomers, and gave the two major diastereoisomers as a mixture (550 mg), which was separated on a Chiralcel OJ-H column (30 mm×250 mm), eluting with 10% EtOH (containing 0.2%isopropylamine)-heptane (containing 0.2%isopropylamine), flow-rate=30 mL/min, detecting at 215 nm. Fractions with RT=46-50 min were combined and fractions with RT=64-78 min were combined. Fractions with RT=50-64 min were mixed fractions and were re-processed using the same Chiralcel OJ-H column. The fractions were concentrated under reduced pressure to give the two major isomers of the title compound differing at the tetrahydrofuran asymmetric centre:

Isomer 1 (100 mg, 7%): LCMS (System B) RT=1.31 min, 96.4%, ES+ve m/z 478 (M+H)⁺; Analytical chiral HPLC RT=36.0 min, 94.6% on a Chiralcel OJ-H column (4.6 mm×250 mm), eluting with 15% EtOH (containing 0.2%isopropylamine)-heptane (containing 0.2%isopropylamine), flow-rate=1 mL/min, detecting at 215 nm.

Isomer 2 (66 mg, 4%): LCMS (System B) RT=1.31 min, 100%, ES+ve m/z 478 (M+H)⁺; Analytical chiral HPLC RT=39.3 min, 97.2% on a Chiralcel OJ-H column (4.6 mm×250 mm), eluting with 15% EtOH (containing 0.2%isopropylamine)-heptane (containing 0.2%isopropylamine), flow-rate=1 mL/min, detecting at 215 nm.

Intermediate 34: Ethyl 2-(3-bromophenoxy)-2-methylpropanoate

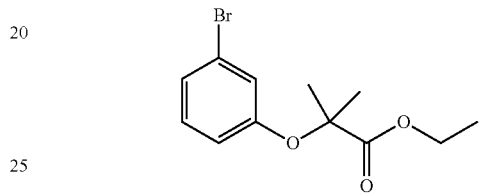

A solution of 3-bromophenol (25 g, 145 mmol), ethyl 2-bromo-2-methylpropanoate (23.49 mL, 159 mmol) in DMF (250 mL) was treated with potassium carbonate (39.9 g, 289 mmol) and the resulting suspension was stirred at 50° C. for 16 h. The reaction mixture was cooled to 25° C., diluted with water (200 mL) and extracted with EtOAc (3×100 mL). The organic extracts were washed with water (100 mL), dried (Na₂SO₄), filtered and the filtrate was concentrated under reduced pressure. The residue was adsorbed on to silica gel (50 g), and purified by column chromatography on silica gel eluting with 10% EtOAc in petroleum ether. The fractions were concentrated in vacuo to give the title compound (16 g, 38%) as a yellow liquid: MS FID m/z 286, 288 (M⁺).

Intermediate 35: 2-(3-Bromophenoxy)-2-methylpropan-1-ol

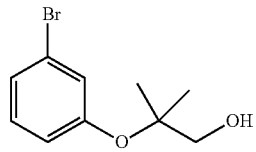

To a stirred solution of ethyl 2-(3-bromophenoxy)-2-methylpropanoate (Intermediate 34) (16 g, 55.7 mmol) in THF (150 mL) was added a 2M solution of lithium borohydride in THF (27.9 mL, 55.7 mmol) at 0° C. and the resulting mixture was stirred at room temperature for 8 h. The reaction mixture was cooled to 0° C. and quenched by addition of aqueous ammonium chloride solution (50 mL), and extracted with EtOAc (3×100 mL). The organic solution was washed with water (100 mL), brine (100 mL), dried (Na₂SO₄), filtered and concentrated in vacuo to give the title compound (10.8 g, 68%) as a pale yellow liquid: MS FID m/z 244, 246 (M⁺).

Intermediate 36: 1-Bromo-3-((1-methoxy-2-methyl-propan-2-yl)oxy)benzene

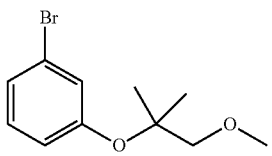

To a stirred solution of 2-(3-bromophenoxy)-2-methylpropan-1-ol (Intermediate 35) (10 g, 40.8 mmol) in THF (100 mL) was added sodium hydride (60% in oil; 1.632 g, 40.8 mmol) at 0° C., followed by iodomethane (3.83 mL, 61.2 mmol) and the resulting mixture was stirred at 25° C. for 3 h. The reaction mixture was cooled to 0° C. and quenched by adding chilled water (50 mL). The mixture was extracted with EtOAc (3×50 mL), and the combined organic extracts were dried (Na$_2$SO$_4$), filtered and concentrated in vacuo to give the title compound (10 g, 93%) as a yellow liquid: MS FID m/z 258, 260 (M$^+$).

Intermediate 37: 2-(3-((1-Methoxy-2-methylpropan-2-yl)oxy)phenyl)-4,4,5,5-tetramethyl-1,3,2-dioxaborolane

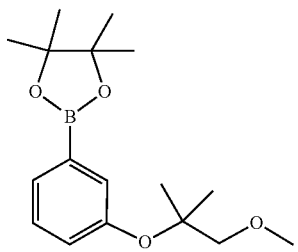

A solution of 1-bromo-3-((1-methoxy-2-methylpropan-2-yl)oxy)benzene (Intermediate 36) (10 g, 38.6 mmol), 4,4,4',4',5,5,5',5'-octamethyl-2,2'-bi(1,3,2-dioxaborolane) (9.80 g, 38.6 mmol) in 1,4-dioxane (100 mL) was deoxygenated with argon gas and then potassium acetate (7.57 g, 77 mmol) was added, followed by PdCl$_2$(dppf)-CH$_2$Cl$_2$ adduct (3.15 g, 3.86 mmol) and the resulting mixture was stirred at 100° C. for 18 h. The reaction mixture was cooled to 25° C., filtered through a Celite bed, the bed was washed with EtOAc (100 mL), and the filtrate was concentrated in vacuo. The residue was adsorbed on to slica gel (20 g) and purified by column chromatography on silica eluting with 10% EtOAc-hexane. The pure fractions were concentrated in vacuo to give the title compound (9.4 g, 75%) as a green liquid: MS FID m/z 306 (M$^+$).

Intermediate 38: (5)-Methyl 3-(3-((1-methoxy-2-methylpropan-2-yl)oxy)phenyl)-4-((R)-3-(2-(5,6,7,8-tetrahydro-1,8-naphthyridin-2-yl)ethyl)pyrrolidin-1-yl)butanoate

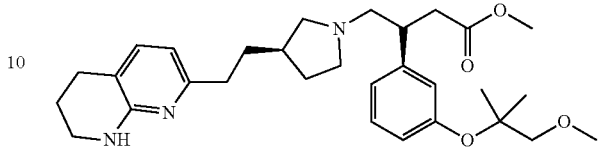

A stirred solution of (R,E)-methyl 4-(3-(2-(5,6,7,8-tetrahydro-1,8-naphthyridin-2-yl)ethyl)pyrrolidin-1-yl)but-2-enoate (Intermediate 6) (900 mg, 2.131 mmol), 2-(3-((1-methoxy-2-methylpropan-2-yl)oxy)phenyl)-4,4,5,5-tetramethyl-1,3,2-dioxaborolane (Intermediate 37) (3.26 g, 10.6 mmol) and aqueous KOH (3.8M, 1.682 mL, 6.39 mmol) in 1,4-dioxane (15 mL) was deoxygenated with argon for 25 min. In a separate vial a solution of (R)-BINAP (159 mg, 0.256 mmol) and chloro(1,5-cyclooctadiene)rhodium (I) dimer (52.5 mg, 0.107 mmol) in 1,4-dioxane (5 mL) was deoxygenated with argon for 15 min and added to the above solution. The mixture was deoxygenated with argon for another 10 min. The resulting reddish reaction mixture was stirred at 90° C. for 18 h. The reaction mixture was cooled to 25° C. and filtered through Celite pad. The Celite bed was washed with EtOAc (10 mL) and the combined filtrate and washing were concentrated in vacuo. The residue was adsorbed on to silica gel (10 g) and purified by column chromatography on silica gel eluting with 5% MeOH (containing 1% 2N ammonia in MeOH) in DCM. The fractions were concentrated in vacuo to give impure product (600 mg) which was further purified by column chromatography on silica, eluting with 25% EtOH-EtOAc. The fractions were concentrated in vacuo to give the title compound (350 mg, 29%) as a yellow oil: MS ES+ve m/z 510 (M+H)$^+$; Analytical chiral SFC on a Chiralcel OD-H column (250 mm×4.6 mm) RT=2.00 min, 81.5%, CO$_2$, 40% co-solvent (0.5% diethylamine in MeOH), 4 g/min, 100 Bar, 30° C., detecting at 210 nm.

Intermediate 39: (5)-1-Methoxypropan-2-yl 4-methylbenzenesulfonate

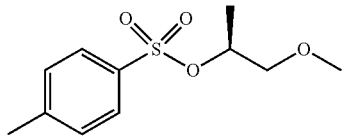

A solution of (S)-1-methoxypropan-2-ol (available from Combi-Blocks) (5 g, 55 mmol) in DCM (75 mL) and pyridine (12.5 mL, 155 mmol) was treated at room temperature with 4-methylbenzenesulfonyl chloride (12 g, 62.9 mmol) and the mixture was stirred for 16 h at room temperature. Ice (50 g) was added and the reaction mixture was stirred for 1 h. The organic layer was separated and washed with 10% aqueous sulfuric acid (12.5 mL×4), water (15 mL), and dried (Na$_2$SO$_4$). The residue was purified by column chromatography on silica gel eluting with DCM (100 mL) and the fractions were concentrated under reduced pressure to give the title compound (6.5 g, 48%) as a colourless liquid: MS ES+ve m/z 245 (M+H)⁺.

Intermediate 40: (R)-1-Bromo-3-((1-methoxypropan-2-yl)oxy)benzene

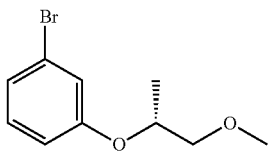

A solution of 3-bromophenol (3.5 g, 20.2 mmol) in DMF (25 mL) was treated with potassium tert-butoxide (2.57 g, 22.9 mmol) and cooled to 0° C. (S)-1-Methoxypropan-2-yl 4-methylbenzenesulfonate (Intermediate 39) (4.9 g, 20.1 mmol) was added and the mixture was stirred at room temperature for 16 h. MeOH (0.6 mL) was added and reaction mixture was stirred for 16 h. More MeOH (2.1 mL) was added and mixture stirred for 4 h. Water (25 mL) was added and the mixture was extracted with petroleum ether (125 mL×2). The organic phase was washed with water (15 mL), dried (Na$_2$SO$_4$), and concentrated in vacuo. The residue was adsorbed on to silica (25 g) and purified by chromatography eluting with 3% EtOAc-petroleum ether. The fractions were evaporated under reduced pressure to give the title compound (2.1 g, 42%) as a colourless liquid: MS ES+ve m/z 245, 247 (M+H)⁺.

Intermediate 41: (R)-2-(3-((1-Methoxypropan-2-yl)oxy)phenyl)-4,4,5,5-tetramethyl-1,3,2-dioxaborolane

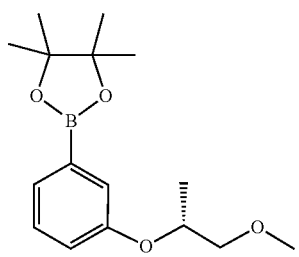

A solution of (R)-1-bromo-3-((1-methoxypropan-2-yl)oxy)benzene (Intermediate 40) (11 g, 45 mmol) in 1,4-dioxane (150 mL) was treated with potassium acetate (8.81 g, 90 mmol), 4,4,4',4',5,5,5',5'-octamethyl-2,2'-bis(1,3,2-dioxaborolane) (11.4 g, 45 mmol) and PdCl$_2$(dppf)-CH$_2$Cl$_2$ adduct (3.66 g, 4.49 mmol) and the mixture was heated for 16 h at 90° C. The reaction mixture was cooled, and filtered through a Celite pad. The filtrate was concentrated under reduced pressure and the residue was adsorbed on silica (10 g) and purified by column chromatography on silica eluting with 5% EtOAc-hexane. The fractions were concentrated under reduced pressure to give the title compound (8 g, 45%) as a yellow liquid: MS ES+ve m/z 293 (M+H)⁺; $[α]_D^{25}$=−14° (c=1.0 in CHCl$_3$).

Intermediate 42: (5)-Methyl 3-(3-(((R)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoate

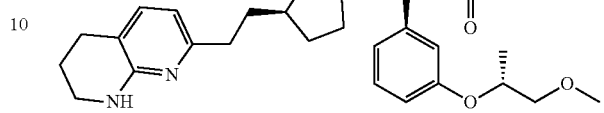

A solution of (R,E)-methyl 4-(3-(2-(5,6,7,8-tetrahydro-1,8-naphthyridin-2-yl)ethyl)pyrrolidin-1-yl)but-2-enoate (Intermediate 6) (1.0 g, 3.0 mmol), (R)-2-(3-((1-methoxypropan-2-yl)oxy)phenyl)-4,4,5,5-tetramethyl-1,3,2-dioxaborolane (Intermediate 41) (2.66 g, 9.11 mmol) and KOH aq solution (3.8 M, 2.4 mL, 9.1 mmol) in 1,4-dioxane (20 mL) was deoxygenated with argon for 25 min. In a separate vial a solution of (R)-BINAP (227 mg, 0.364 mmol) and chloro(1,5-cyclooctadiene)rhodium(I) dimer (75 mg, 0.15 mmol) in 1,4-dioxane (5 mL) was deoxygenated with argon for 20 min and then added to the above solution. Deoxygenation was continued with argon for another 10 min and the reddish reaction mixture was stirred at 90° C. for 18 h. The reaction mixture was filtered through a Celite bed, the bed was washed with 1,4 dioxane (10 mL), and the filtrate was concentrated in vacuo. The residue was dissolved in DCM (5 mL) and adsorbed on to silica (2.5 g) and purified by chromatography on silica eluting with 6-10% MeOH in DCM. The pure fractions were concentrated in vacuo to give the title compound (250 mg, 15%) as light brown gum: MS ES+ve m/z 496 (M+H)⁺.

Intermediate 43: 1-Bromo-3-(2-isopropoxyethoxy)benzene

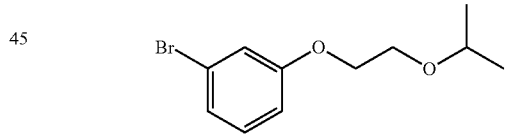

To a stirred solution of 3-bromophenol (8 g, 46 mmol), 2-isopropoxyethanol (6.35 mL, 55.5 mmol) and triphenylphosphine (15.77 g, 60.1 mmol) in THF (80 mL) was added DIAD (9.89 mL, 50.9 mmol) dropwise under argon at 0° C. Then the mixture was stirred at room temperature for 18 h. The mixture was quenched with water (50 mL) and concentrated under reduced pressure to remove THF. The water layer was extracted with EtOAc (2×200 mL) and the organic layer was dried (Na$_2$SO$_4$) and concentrated under reduced pressure. This residue (30 g) was adsorbed on to silica gel (60 g) and purified by column chromatography eluting with a gradient of 0-5% EtOAc in petroleum ether. The appropriate fractions were concentrated under reduced pressure to afford the title compound (6 g, 50%) as a colourless oil: $^1$H NMR (CDCl$_3$, 400 MHz) δ 7.15-7.05 (3H, m), 6.85 (1H, br d, J 8 Hz), 4.08 (2H, t, J 5 Hz), 3.76 (2H, t, J 5 Hz), 3.67 (1H, m), 1.20 (6H, d, J 6 Hz).

Intermediate 44: 2-(3-(2-Isopropoxyethoxy)phenyl)-4,4,5,5-tetramethyl-1,3,2-dioxaborolane

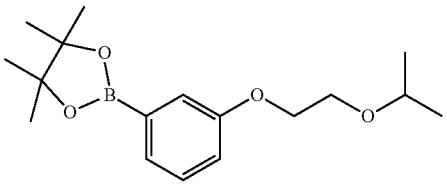 [SMILES: CC(C)OCCOc1cccc(B2OC(C)(C)C(C)(C)O2)c1]

A solution of 1-bromo-3-(2-isopropoxyethoxy)benzene (Intermediate 43) (5 g, 19 mmol), bis(pinacolato)diboron (5.88 g, 23.15 mmol) and potassium acetate (5.68 g, 57.9 mmol) in toluene (100 mL) was deoxygenated with argon for 15 min. PdCl$_2$(dppf) (0.706 g, 0.965 mmol) was added and again deoxygenated using argon for another 15 min. The mxiture was then heated to 100° C. overnight. The mixture was filtered through a Celite bed and the bed was washed with EtOAc. The filtrate was concentrated under reduced pressure and the residue was adsorbed on to Florosil (26 g) and purified by chromatography on Florosil (120 g) eluting with petroleum ether. The fractions were evaporated under reduced pressure to afford the title compound (5 g, 85%): MS ES+ve m/z 307 (M+H)$^+$.

Intermediate 45: Methyl 3-(3-(2-isopropoxyethoxy)phenyl)-4-((R)-3-(2-(5,6,7,8-tetrahydro-1,8-naphthyridin-2-yl)ethyl)pyrrolidin-1-yl)butanoate

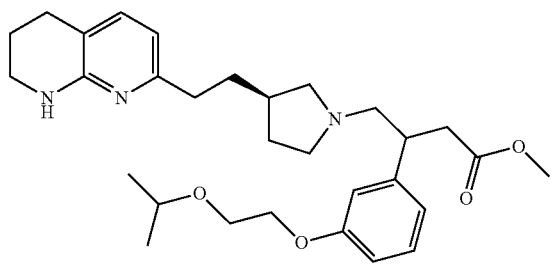 [SMILES: COC(=O)CC(CN1CC[C@@H](CCc2ccc3c(n2)NCCC3)C1)c1cccc(OCCOC(C)C)c1]

A stirred solution of (R)-BINAP (45.4 mg, 0.073 mmol) and Rh$_2$Cl$_2$(COD)$_2$ (14.97 mg, 0.030 mmol) in 1,4-dioxane (3 mL) was deoxygenated with argon for 15 min. In another flask a solution of (R,E)-methyl 4-(3-(2-(5,6,7,8-tetrahydro-1,8-naphthyridin-2-yl)ethyl)pyrrolidin-1-yl)but-2-enoate (Intermediate 6) (200 mg, 0.607 mmol), 2-(3-(2-isopropoxyethoxy)phenyl)-4,4,5,5-tetramethyl-1,3,2-dioxaborolane (Intermediate 44) (558 mg, 1.821 mmol) and aqueous KOH (3.8M, 0.479 mL, 1.821 mmol) in 1,4-dioxane (3 mL) was deoxygenated with argon for 15min. The two reaction mixtures were combined, deoxygenated for a further 15 min, and heated to 100° C. for 4 h under argon. After completion of reaction, the mixture was allowed warm to room temperature and filtered through a Celite bed and washed with DCM (25 mL). The filtrate and washings were concentrated under reduced pressure and the residue (400 mg) was adsorbed on to silica (1 g) and purified by column chromatography on silica eluting with a gradient of 0-15% MeOH in DCM. The appropriate fractions were collected and concentrated under reduced pressure. The product (100 mg) was purified further by preparative TLC eluting with 5% MeOH in DCM and running the plate twice. The appropriate fraction was removed and extracted with 5% MeOH in DCM and flitered. The filtrate was concentrated under reduced pressure to afford the title compound (70 mg, 19%) as a pale yellow gum: MS ES+ve m/z 510 (M+H)$^+$; Analytical chiral SFC on a Chiralcel OD-H column (250 mm×4.6 mm) RT=2.35 min, 85.5%, CO$_2$, 40% co-solvent (0.5% diethylamine in MeOH), 4 g/min, 100 Bar, 29.8° C., detecting at 323 nm.

Intermediate 46: (R)-2-((3-Bromophenoxy)methyl)tetrahydrofuran

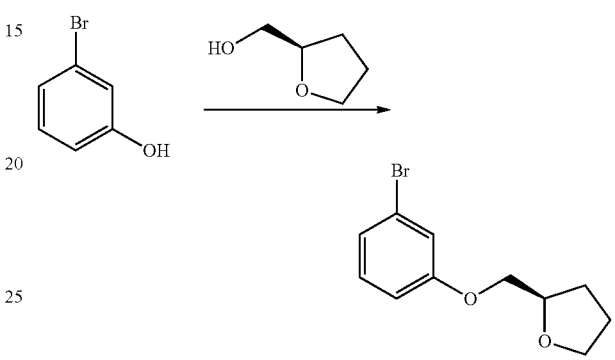

A stirred solution of 3-bromophenol (1 g, 5.78 mmol), triphenylphosphine (1.97 g, 7.51 mmol), (R)-(tetrahydrofuran-2-yl)methanol (0.708 g, 6.94 mmol) (available from Frapps) in THF (15 mL) was added DIAD (1.46 mL, 7.51 mmol) at 0° C. and the resulting mixture was stirred at 25° C. for 16 h. The reaction mixture was concentrated in vacuo and the residual solid was diluted with DCM (10 mL), adsorbed on to silica gel and purified by silica column chromatography, eluting with 5% EtOAc in hexane. The corresponding fractions were concentrated in vacuo to afford the title compound (1 g, 52%) as a yellow liquid: MS ES+ve m/z 257, 259 (M+H)$^+$.

Intermediate 47. (R)-4,4,5,5-Tetramethyl-2-(3-((tetrahydrofuran-2-yl)methoxy)phenyl)-1,3,2-dioxaborolane

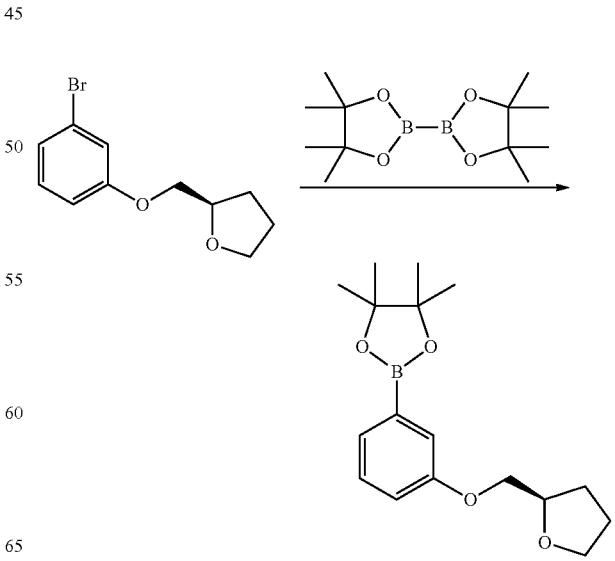

A solution of (R)-2-((3-bromophenoxy)methyl)tetrahydrofuran (Intermediate 46) (1 g, 3.89 mmol), potassium acetate (1.145 g, 11.67 mmol) and 4,4,4',4',5,5,5',5'-octamethyl-2,2'-bi(1,3,2-dioxaborolane) (1.481 g, 5.83 mmol) in 1,4-dioxane (15 mL) was deoxygenated with argon for 15 min. PdCl$_2$(dppf)-CH$_2$Cl$_2$ adduct (0.159 g, 0.194 mmol) was added and the reaction mixture was stirred at 100° C. for 18 h. The solvent was removed in vacuo and the residue was purified by column chromatography on silica (10 g), eluting with petroleum ether. The collected fractions were concentrated in vacuo to afford the title compound (1 g, 66%) as yellow liquid: MS ES+ve m/z 305 (M+H)$^+$.

Intermediate 48. Methyl 4-((R)-3-(2-(5,6,7,8-tetrahydro-1,8-naphthyridin-2-yl)ethyl)pyrrolidin-1-yl)-3-(3-(((R)-tetrahydrofuran-2-yl)methoxy)phenyl)butanoate

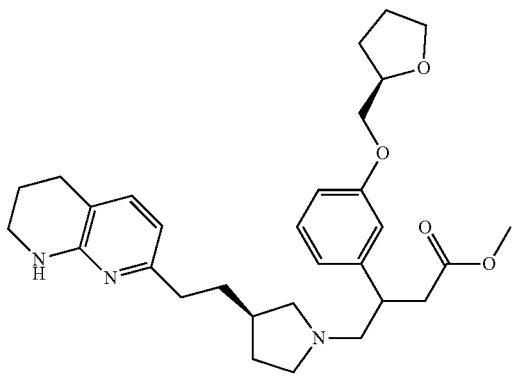 [SMILES: COC(=O)CC(CN1CC[C@@H](CCc2ccc3c(n2)NCCC3)C1)c1cccc(OC[C@H]2CCCO2)c1]

A stirred solution of (E)-methyl 4-(3-(2-(5,6,7,8-tetrahydro-1,8-naphthyridin-2-yl)ethyl)pyrrolidin-1-yl)but-2-enoate (Intermediate 6) (400 mg, 1.21 mmol) in1,4-dioxane (5 mL) was treated with (R)-4,4,5,5-tetramethyl-2-(3-((tetrahydrofuran-2-yl)methoxy)phenyl)-1,3,2-dioxaborolane (Intermediate 47) (1.847 g, 6.07 mmol) and aqueous KOH (3.8M, 0.639 mL, 2.428 mmol) and the solution was deoxygenated with argon for 15-20 min. In a separate vessel (R)-BINAP (91 mg, 0.146 mmol) and chloro(1,5-cyclooctadiene)rhodium(I) dimer (29.9 mg, 0.061 mmol) in 1,4-dioxane (5 mL) were deoxygenated with argon for 15 min. This solution was added to the initial vessel and deoxygenation was continued for another 15 min. The resulting reddish reaction mixture was stirred at 90° C. for 12 h. The reaction mixture was cooled to room temperature, and the solvent was removed under reduced pressure. The residue was purified by column chromatography on a 40 g silica column eluting with 20% MeOH-DCM to afford the title compound (220 mg, 36%) as a pale yellow gum: MS ES+ve m/z 508 (M+H)$^+$. Analytical chiral SFC on a Chiralcel OD-H column (250 mm×4.6 mm) RT=2.27 min, 32.9%, and RT=2.80 min, 52.4% CO$_2$, 40% co-solvent (0.5% diethylamine in MeOH), 5 g/min, 100 Bar, 30.4° C., detecting at 322 nm. Intermediate 49. (S)-2-((3-Bromophenoxy)methyl)tetrahydrofuran

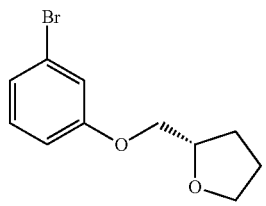 [SMILES: Brc1cccc(OC[C@@H]2CCCO2)c1]

A stirred solution of 3-bromophenol (1 g, 5.78 mmol), triphenylphosphine (1.971 g, 7.51 mmol), (S)-(tetrahydrofuran-2-yl)methanol (available from Alfa Aesar) (0.708 g, 6.94 mmol) in THF (15 mL) was treated with DIAD (1.46 mL, 7.51 mmol) at 0° C. and stirred at 25° C. for 16 h. The reaction mixture was concentrated in vacuo, 1N aqueous NaOH solution (10 mL) added and extracted with DCM (2×30 mL), and purified by silica column chromatography, eluting with 5% EtOAc in hexane. The corresponding fractions were concentrated in vacuo to afford the title compound (1 g, 67%) as a yellow liquid: MS ES+ve m/z 257, 259 (M+H)$^+$.

Intermediate 50. (S)-4,4,5,5-Tetramethyl-2-(3-((tetrahydrofuran-2 yl)methoxy)phenyl)-1,3,2-dioxaborolane

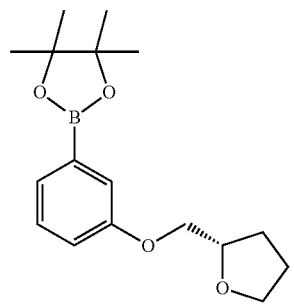 [SMILES: CC1(C)OB(c2cccc(OC[C@@H]3CCCO3)c2)OC1(C)C]

A solution of (S)-2-((3-bromophenoxy)methyl)tetrahydrofuran (Intermediate 49) (1 g, 3.89 mmol), potassium acetate (1.145 g, 11.67 mmol) and bis(pinacolato)diboron (1.481 g, 5.83 mmol) in 1,4-dioxane (15 mL) was deoxygenated with argon for 15 min, then was treated with PdCl$_2$(dppf)-CH$_2$Cl$_2$ adduct (0.159 g, 0.194 mmol). The reaction mixture was stirred at 100° C. for 18 h. The solvent was removed in vacuo to afford the crude product. The crude product was dissolved in DCM (30 mL) then purified by silica column chromatography (50 g column), eluting with 5% EtOAc in petroleum ether, and the collected fractions were concentrated in vacuo to afford the title compound (1 g, 85%) as a yellow liquid: MS ES+ve m/z 305 (M+H)$^+$.

Intermediate 51. Methyl 4-((R)-3-(2-(5,6,7,8-tetra-hydro-1,8-naphthyridin-2-yl)ethyl)pyrrolidin-1-yl)-3-(3-(((S)-tetrahydrofuran-2-yl)methoxy)phenyl)butanoate

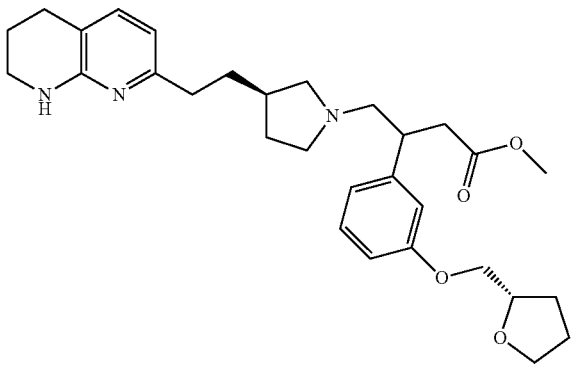 [SMILES: COC(=O)CC(CN1CC[C@@H](CCc2ccc3c(n2)NCCC3)C1)c1cccc(OC[C@@H]2CCCO2)c1]

A mixture of (R,E)-methyl 4-(3-(2-(5,6,7,8-tetrahydro-1,8-naphthyridin-2-yl)ethyl)pyrrolidin-1-yl)but-2-enoate (Intermediate 6) (1.0 g, 3.04 mmol), (S)-4,4,5,5-tetramethyl-2-(3-((tetrahydrofuran-2-yl)methoxy-phenyl)-1,3,2-dioxaborolane (Intermediate 50) (2.77 g, 9.11 mmol), KOH (3.8M, 1.6 mL, 6.1 mmol) were dissolved in 1,4-dioxane (10 mL). The flask was purged with nitrogen for 5 min and then (R)-BINAP (189 mg, 0.304 mmol) and chloro(1,5-cyclooctadiene)rhodium(I) dimer (75 mg, 0.15 mmol) were added. The reaction mixture was heated to 90° C. for 2 h, cooled and concentrated in vacuo. The residue was dissolved in DCM (10 mL), adsorbed on to silica and purified by column chromatography eluting with 20% MeOH-DCM. The fractions were concentrated and the residue was dissolved in MeOH (4 mL) and passed through an SCX cartridge (2 g), eluting with 2CV of methanol and then 2CV of 2M ammonia in methanol. The appropriate fractions were concentrated in vacuo to give the title compound (250 mg, 14%) as a pale brown oil: MS ES+ve m/z 508 (M+H)+. The compound is a mixture of two diastereoisomers at the benzylic centre with the major isomer having the S-configuration and the following characterising data. Analytical chiral SFC on a Chiralcel OD-H column (250 mm×4.6 mm) RT=3.08 min, 13.2%, RT=5.8 min, 73.8%, and $CO_2$, 40% co-solvent (0.5% diethylamine in MeOH), 4 g/min, 100 Bar, 30° C., detecting at 245 nm.

The following Intermediate compounds were prepared by similar procedures to those described above via a coupling reaction of the corresponding pinacol ester and the compound of Formula (III) (Intermediate 6) wherein $R^4$ represents methyl:

| Intermediate | Formula | Characterising data |
| --- | --- | --- |
| 52 | 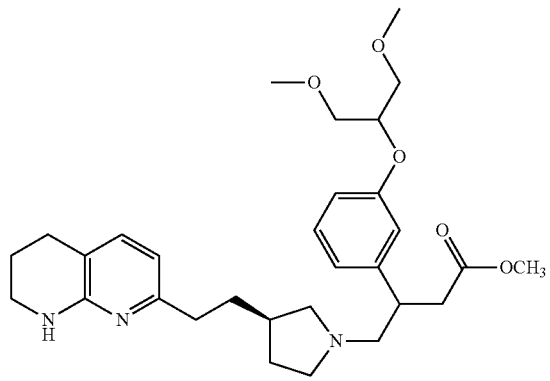 [SMILES: COCC(COC)Oc1cccc(C(CC(=O)OC)CN2CC[C@@H](CCc3ccc4c(n3)NCCC4)C2)c1] | MS ES+ve m/z 526 (M + H)+. Analytical chiral SFC on a Chiralcel OD-H column (250 mm × 4.6 mm) RT = 1.52 min, 34.8% and RT = 1.70 min, 51.2%, $CO_2$, 40% co-solvent (0.5% diethylamine in MeOH), 5 g/min, 100 Bar, detecting at 322 nm at 28° C. |
| 53 | 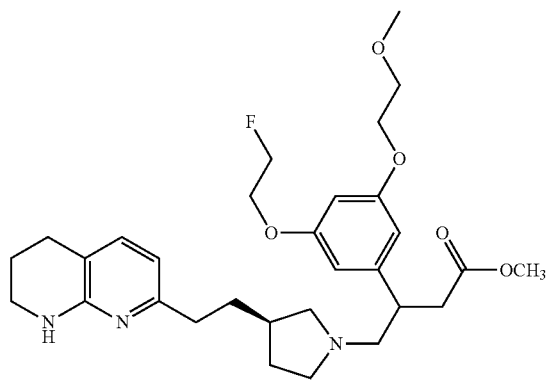 [SMILES: COCCOc1cc(OCCF)cc(C(CC(=O)OC)CN2CC[C@@H](CCc3ccc4c(n3)NCCC4)C2)c1] | MS ES+ve m/z 544 (M + H)+ |

| Intermediate | Formula | Characterising data |
|---|---|---|
| 54 | | MS ES+ve m/z 496 (M + H)+. Analytical chiral SFC on a Chiralcel OD-H column (250 mm × 4.6 mm) RT = 2.29 min, 14.1% and RT = 2.61 min, 80.5%, $CO_2$, 40% co-solvent (0.5% diethylamine in MeOH), 4 g/min, 100 Bar, detecting at 321 nm at 31° C. |
| 55 | | MS ES+ve m/z 494 (M + H)+ |

Intermediate 56:
1-Bromo-3-((1,3-dimethoxypropan-2-yl)oxy)benzene.

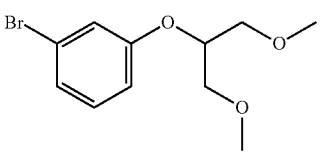

To a solution of 3-bromophenol (6 g, 34.7 mmol) and 1,3-dimethoxypropan-2-ol (5.00 g, 41.6 mmol) in THF (150 mL) was added triphenylphosphine (13.64 g, 52.0 mmol) and the reaction mixture cooled to 0° C. followed by dropwise addition of DIAD (6.74 mL, 34.7 mmol). The reaction was allowed to warm to room temperature, then stirred for 12 h. The reaction mixture was concentrated in vacuo. The obtained residue was dissolved in EtOAc (50 mL), washed with water (50 mL) and brine (50 mL), dried over $Na_2SO_4$, concentrated in vacuo and subjected to silica column chromatography (50 g column), eluting with 20% EtOAc in petroleum ether. The relevant fractions were combined and concentrated in vacuo affording the title compound (4.0 g, 42%) as a yellow liquid: MS ES+ve m/z 275 (M+H)+.

Intermediate 57:
2-(3-Bromophenoxy)propane-1,3-diol.

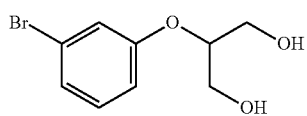 [SMILES: OCC(CO)Oc1cccc(Br)c1]

To a solution of 1-bromo-3-((1,3-dimethoxypropan-2-yl)oxy)benzene (Intermediate 56) (11 g, 40.0 mmol) in DCM (100 mL) cooled to 0° C. was added boron tribromide (11.34 mL, 120 mmol) dropwise and stirred for 0.5 h. The reaction was quenched with addition of ice-water (20 mL). The layers were separated, the aqueous layer basified with 10% aqueous $NaHCO_3$ solution (50 mL) and extracted with DCM (3×70 mL). The combined organic layers were washed with water (50 mL) and brine (50 mL), dried over $Na_2SO_4$, concentrated in vacuo and subjected to silica column chromatography (25 g column) eluting with 30% EtOAc in petroleum ether. The relevant fractions were combined and concentrated in vacuo to afford the title compound (8.2 g, 83%) as an off white solid: $^1$H NMR (400 MHz, $CDCl_3$) δ 7.20-7.10 (m, 3H), 6.93 (d, J=7.5 Hz, 1H), 4.43 (quin, J=4.7 Hz, 1H), 3.97-3.86 (m, 4H), 3.71 (t, J=6.3 Hz, 1H), 3.51-3.43 (m, 1H).

Intermediate 58: 2-(3-Bromophenoxy)-3-hydroxypropyl 4-methylbenzenesulfonate.

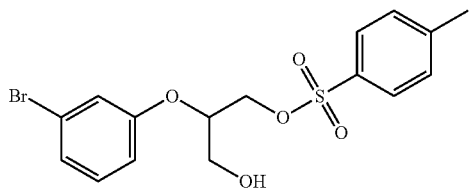 [SMILES: Cc1ccc(S(=O)(=O)OCC(CO)Oc2cccc(Br)c2)cc1]

To a solution of 2-(3-bromophenoxy)propane-1,3-diol (Intermediate 57) (8.2 g, 33.2 mmol) in THF (100 mL) cooled to 0° C. was added NaH (1.327 g, 33.2 mmol) and tosyl chloride (6.33 g, 33.2 mmol) and stirred 0.5 h. The reaction was quenched with addition of ice water (20 mL) and EtOAc (100 mL). The layers were separated and the organic layer washed with water (50 mL), brine (30 mL), dried over $Na_2SO_4$, concentrated in vacuo and subjected to silica column chromatography (25 g column) eluting with 30% EtOAc in petroleum ether. The relevant fractions were combined and concentrated in vacuo to afford the title compound (6.2 g, 47%) as a colourless liquid: MS ES+ve m/z 401, 403 (M+H)$^+$.

Intermediate 59: 3-(3-Bromophenoxy)oxetane.

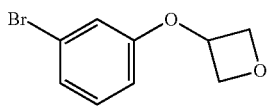 [SMILES: Brc1cccc(OC2COC2)c1]

To a solution of 2-(3-Bromophenoxy)-3-hydroxypropyl 4-methylbenzenesulfonate (Intermediate 58) (6.1 g, 15.20 mmol) in THF (60 mL) cooled to 0° C. was added NaH (0.730 g, 18.24 mmol) and stirred for 23 h at 40° C. The reaction was quenched with dropwise addition of 10% aqueous $NaHCO_3$ solution (15 mL) and extracted with EtOAc (3×50 mL). The combined organic layers were washed with water (20 mL), brine (20 mL), dried over $Na_2SO_4$, concentrated in vacuo and subjected to silica column chromatography eluting with 25% EtOAc in petroleum ether. The relevant fractions were combined and concentrated in vacuo to afford the title compound (1.3 g, 35%) as a colourless liquid: MS FID m/z 228, 230 (M$^+$).

Intermediate 60: 4,4,5,5-Tetramethyl-2-(3-(oxetan-3-yloxy)phenyl)-1,3,2-dioxaborolane.

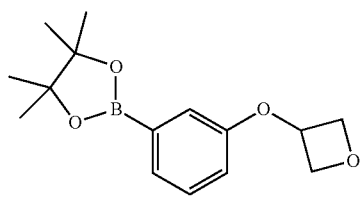 [SMILES: CC1(C)OB(c2cccc(OC3COC3)c2)OC1(C)C]

To a solution of 3-(3-bromophenoxy)oxetane (Intermediate 59) (1.0 g, 4.37 mmol) in 1,4-dioxane (20 mL) was added bis(pinacolato)diboron (1.330 g, 5.24 mmol), potassium acetate (1.285 g, 13.10 nnnnol). The reaction mixture was deoxygenated with $N_2$ for 5 min and $PdCl_2(dppp-CH_2Cl_2$ adduct (0.713 g, 0.873 mmol) added. The reaction mixture was stirred at 90° C. for 12 h. The reaction mixture was concentrated in vacuo, dissolved in EtOAc (100 mL), washed with water (30 mL), brine (30 mL), dried over $Na_2SO_4$, concentrated in vacuo and subjected to silica column chromatography (54 g column) eluting with 20% EtOAc in petroleum ether. The relevant fractions were combined and concentrated in vacuo to afford the title compound (950 mg, 68%) as a colourless liquid: MS FID m/z 276 (M$^+$).

Intermediate 61: (S)-Methyl 3-(3-(oxetan-3-yloxy)phenyl)-4-((R)-3-(2-(5,6,7,8-tetrahydro-1,8-naphthyridin-2-yl)ethyl)pyrrolidin-1-yl)butanoate

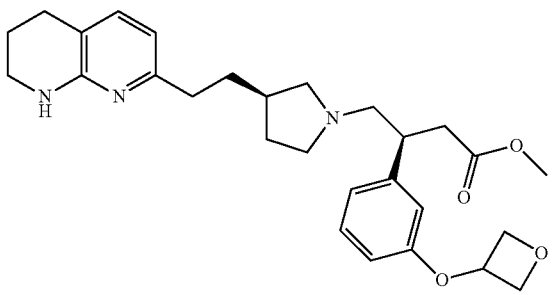 [SMILES: COC(=O)C[C@H](CN1CC[C@@H](CCc2ccc3c(n2)NCCC3)C1)c1cccc(OC2COC2)c1]

A mixture of (R,E)-methyl 4-(3-(2-(5,6,7,8-tetrahydro-1,8-naphthyridin-2-yl)ethyl)pyrrolidin-1-yl)but-2-enoate (Intermediate 6) (750 mg, 2.28 mmol), 4,4,5,5-tetramethyl-2-(3-(oxetan-3-yloxy)phenyl)-1,3,2-dioxaborolane (Intermediate 60) (1257 mg, 4.55 mmol), chloro(1,5-cyclooctadiene)rhodium(I) dimer (56.1 mg, 0.114 mmol), 3.8M KOH (1.198 mL, 4.55 mmol) and (R)-BINAP (142 mg, 0.228 mmol) in 1,4-dioxane (10 mL) were combined and degased with argon for 30 min. The resulting red solution was heated at 90° C. for 2 h. The reaction mixture was concentrated in vacuo and the crude material was purified by column chromatography using a 40 g column eluting with 20-30% MeOH-DCM. The appropriate fractions were combined to give the title compound (0.4 g, 27%) as yellow gum: MS ES+ve m/z 480 (M+H)$^+$.

Intermediate 62. 4-(3-Bromophenoxy)tetrahydro-2H-pyran.

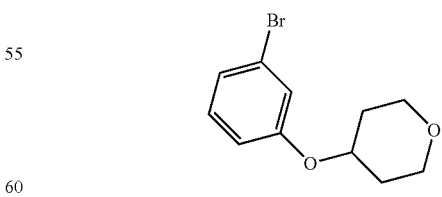

To a cooled, 5° C., solution of 3-bromophenol (7.63 g, 44.1 mmol), tetrahydro-2H-pyran-4-ol (5.41 g, 52.9 mmol) (available from Sigma Aldrich) and triphenylphosphine (23.13 g, 88 mmol) in THF (200 mL) was added DIAD (17.15 mL, 88 mmol) dropwise over 15 min. The reaction mixture was allowed to warm to room temperature and stirred under N₂ for 20 h. The solvent was removed in vacuo and the residue was dissolved in DCM and subjected to silica column chromatography (340 g column) eluting with 0-25% EtOAc in cyclohexane. The relevant fractions were combined and concentrated in vacuo. The residue was dissolved in TBME and washed with 2N sodium hydroxide solution. The organic phase was dried (MgSO₄) and evaporated in vacuo to give (4.89 g) as a colourless oil. The oil was dissolved in DCM and subjected to silica column chromatography (70 g column) eluting with 0-25% EtOAc in cyclohexane. The relevant fractions were combined and concentrated in vacuo to give the title compound (3.88 g, 34%) as a colourless oil; ¹H NMR (CDCl₃, 400 MHz) δ 7.16-7.05 (3H, m), 6.84 (1H, m), 4.50-4.42 (1H, m), 4.01-3.94 (2H, m), 3.62-3.54 (2H, m), 2.05-1.96 (2H, m), 1.83-1.73 (2H, m).

Intermediate 63. (3-((Tetrahydro-2H-pyran-4-yl)oxy)phenyl)boronic acid.

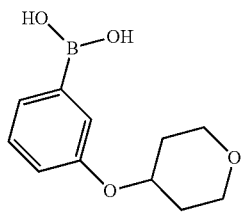 [SMILES: OB(O)c1cccc(OC2CCOCC2)c1]

A solution of 4-(3-bromophenoxy)tetrahydro-2H-pyran (Intermediate 62) (3.88 g, 15.09 mmol) in THF (70 mL) under N₂ was cooled to −70° C. To this was added dropwise 1.6M BuLi solution in hexanes (11.79 mL, 18.86 mmol) and the reaction mixture was stirred at −70° C. for 30 min. To this was added triisopropyl borate (5.26 mL, 22.64 mmol) and the reaction mixture was stirred at −70° C. for 1 h. The reaction mixture was allowed to warm to room temperature and then quenched with 2N aqueous hydrochloric acid (20 mL). The reaction mixture was separated between TBME (50 mL) and 2N aqueous hydrochloric acid (50 mL). The aqueous phase was extracted with TBME (50 mL). The combined organic phases were washed with brine (50 mL) and dried (MgSO₄). The solvent was removed in vacuo. The residue was dissolved in DCM and applied to a 100 g silica cartridge. This was eluted with a gradient of 0-100% TBME in cyclohexane over 20 min, followed by 0-40% MeOH in TBME over 30 min. The relevant fractions were combined and evaporated in vacuo. The residue was treated with heptane (30 mL) and the solvent was removed in vacuo to give the title compound as a white solid (2.60 g, 78%). MS ES-ve m/z 221 (M-H)⁺.

Intermediate 64. tert-Butyl (S)-4-((R)-3-(2-(5,6,7,8-tetrahydro-1,8-naphthyridin-2-yl)ethyl)pyrrolidin-1-yl)-3-(3-((tetrahydro-2H-pyran-4-yl)oxy)phenyl)butanoate

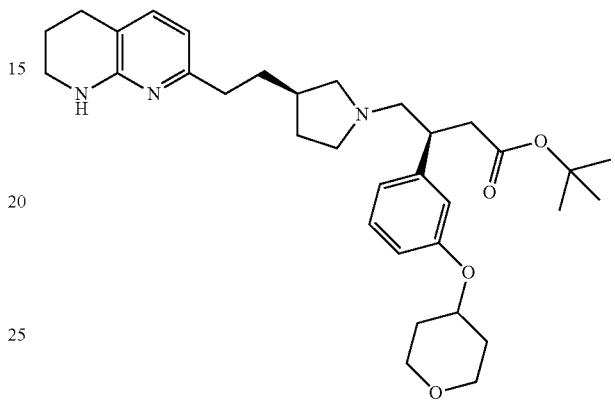

tert-Butyl (R,E)-4-(3-(2-(5,6,7,8-tetrahydro-1,8-naphthyridin-2-yl)ethyl)pyrrolidin-1-yl)but-2-enoate (Intermediate 4) (176 mg, 0.474 mmol) was dissolved in 1,4-dioxane (3 mL), and the solution was added to (3-((tetrahydro-2H-pyran-4-yl)oxy)phenyl)boronic acid (Intermediate 63) (316 mg, 1.421 mmol) followed by chloro(1,5-cyclooctadiene)rhodium(1) dimer (11.68 mg, 0.024 mmol), (R)-BINAP (35.4 mg, 0.057 mmol) and 3.8M KOH (0.312 mL, 1.184 mmol). The mixture was degassed (nitrogen bubbled through) and stirred under an inert atmosphere at 90° C. for 3 h. LCMS showed 1:1 conversion to product and this went no further after an additional 2 h. (3-((Tetrahydro-2H-pyran-4-yl)oxy)phenyl)boronic acid (316 mg, 1.42 mmol), chloro (1,5-cyclooctadiene) rhodium(I) dimer (11.68 mg, 0.024 mmol), (R)-BINAP (35.4 mg, 0.057 mmol), 3.8M KOH (0.312 mL, 1.184 mmol) were all added again to the reaction mixture. 2M Hydrochloric acid (20 mL), and TBME (11 mL) were added to the solution and the two phases were separated. The aqueous phase was basified with solid sodium bicarbonate then extracted with ethyl acetate. The organic phase was washed with brine and dried (MgSO₄) and evaporated (125 mg). This was then dissolved in 1:1 DMSO-MeOH and purified by MDAP. The appropriate fractions were mixed together to give the title compound (96.2 mg, 37%): LCMS (System B) RT=1.50 min, 97%, ES+ve m/z 550 (M+H)⁺; Analytical chiral HPLC RT=9.69 min, 90.1% and RT=15.6 min, 9.9% on a Chiralpak IC column (250 mm×4.6 mm), eluting with 20% EtOH/heptane containing 0.1%isopropylamine, flow-rate=1.0 mL/min, at room temperature, detecting at 235 nm.

PREPARATION OF EXAMPLES

Example 1

(S)-3-(3-(2-methoxyethoxy)phenyl)-4-((R)-3-(2-(5,6,7,8-tetrahydro-1,8-naphthyridin-2-yl)ethyl)pyrrolidin-1-yl)butanoic acid

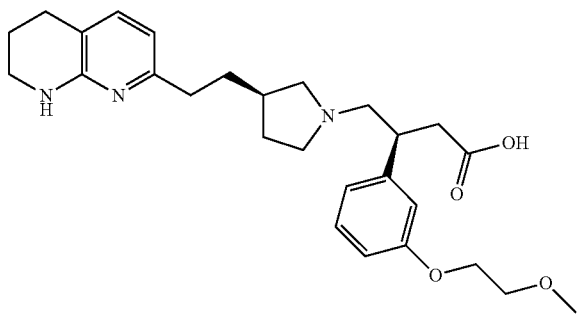 [SMILES: COCCOc1cccc([C@H](CC(=O)O)CN2CC[C@@H](CCc3ccc4c(n3)NCCC4)C2)c1]

(S)-tert-Butyl 3-(3-(2-methoxyethoxy)phenyl)-4-((R)-3-(2-(5,6,7,8-tetrahydro-1,8-naphthyridin-2-yl)ethyl)pyrrolidin-1-yl)butanoate (Intermediate 5) (3.19 g, 6.09 mmol) was dissolved in DCM (30 mL) and TFA (4.69 mL, 60.9 mmol) added. The reaction was stirred at room temperature for 1.5 h. The solvent was evaporated in vacuo and then the residue re-dissolved in ethanol and purified by SPE (SCX) eluting with EtOH (2CV) and then 2M ammonia/methanol (2CV). The basic fractions were combined and evaporated in vacuo to give the title compound (2.759, 97%) as a yellow solid: LCMS (System B) RT=0.82 min, 97%, ES+ve m/z 468 (M+H)$^+$; NMR (CDCl$_3$, 600 MHz) δ includes 7.25-7.19 (1H, m), 7.12 (1H, d, J=7 Hz), 6.80.-6.76 (3H, m), 6.29 (1H, d, J=7 Hz), 4.12 (2H, m), 3.76 (2H, m), 3.45 (3H, s), 3.44-3.39 (4H, m), 3.02-2.93 (2H, m), 2.80-2.67 (5H, m), 2.58-2.42 (3H, m), 2.20-2.10 (1H, m), 2.07-2.00 (1H, m), 1.95-1.84 (3H, m), 1.62-1.56 (1H, m), 1.48-1.40 (1H, m).

Example 2

(S)-3-(3-((R)-2-methoxypropoxy)phenyl)-4-((R)-3-(2-(5,6,7,8-tetrahydro-1,8-naphthyridin-2-yl)ethyl)pyrrolidin-1-yl)butanoic acid

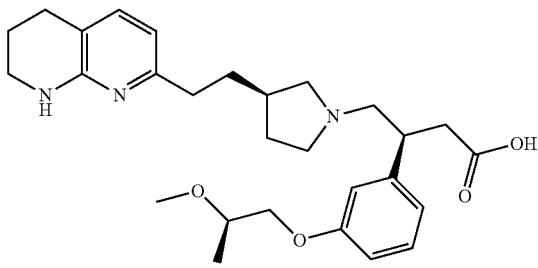 [SMILES: CO[C@H](C)COc1cccc([C@H](CC(=O)O)CN2CC[C@@H](CCc3ccc4c(n3)NCCC4)C2)c1]

A stirred solution of (S)-methyl 3-(3-((R)-2-methoxypropoxy)phenyl)-4-((R)-3-(2-(5,6,7,8-tetrahydro-1,8-naphthyridin-2-yl)ethyl)pyrrolidin-1-yl)butanoate (Intermediate 10) (800 mg, 1.61 mmol) in THF (3 mL) was treated with a solution of lithium hydroxide (193 mg, 8.07 mmol) in water (5.0 mL) and the reaction was stirred at room temperature for 16 h. The solvents were removed under reduced pressure and the residue was purified by preparative HPLC on a Kinetex C18 column (150 mm×30 mm, 5 mm, i.d. 5 μm packing diameter) eluting with a gradient of MeCN-aqueous 10 mM ammonium bicarbonate solution. Appropriate fractions were combined and evaporated in vacuo to give a diastereisomeric mixture (92:8) of the title compound (400 mg, 51%). The mixture was separated by preparative chiral SFC on a Chiralpak AS-H column (250 mm×21 mm), CO$_2$, 50% co-solvent (0.5% isopropylamine in isopropanol), 70 g/min, 100 Bar, 30.2° C., detecting at 318 nm to give the title compound (110 mg, 26%) as a pale yellow solid: MS ES+ve m/z 482 (M+H)$^+$; $^1$H NMR δ (CDCl$_3$, 400 MHz) 7.23-7.17 (2H, m), 7.10 (1H, d, J=7 Hz), 6.81-6.74 (3H, m), 6.28 (1H, d, J=7 Hz), 3.97 (1H, dd, J=9.5, 6 Hz), 3.88 (1H, dd, J=9.5, 4.5 Hz), 3.75-3.67 (1H, m), 3.45 (3H, s), 3.43-3.32 (4H, m), 3.01-2.90 (2H, m), 2.79-2.65 (5H, m), 2.53-2.39 (3H, m), 2.30-1.81 (6H, m), 1.62-1.51 (1H, m), 1.48-1.37 (1H, m), 1.27 (3H, d, J 6 Hz). Analytical chiral SFC on a Chiralpak AS-H column (250 mm×4.6 mm) RT=2.55 min, 98.6%, CO$_2$, 50% co-solvent (0.5% isopropylamine in isopropanol), 4 g/min, 100 Bar, 30.1° C., detecting at 319 nm.

Example 3

(S)-3-(3-((S)-2-methoxypropoxy)phenyl)-4-((R)-3-(2-(5,6,7,8-tetrahydro-1,8-naphthyridin-2-yl)ethyl)pyrrolidin-1-yl)butanoic acid

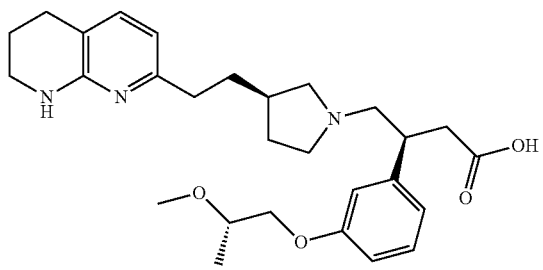 [SMILES: CO[C@@H](C)COc1cccc([C@H](CC(=O)O)CN2CC[C@@H](CCc3ccc4c(n3)NCCC4)C2)c1]

To a stirred solution of (S)-methyl 3-(3-((S)-2-methoxypropoxy)phenyl)-4-((R)-3-(2-(5,6,7,8-tetrahydro-1,8-naphthyridin-2-yl)ethyl)pyrrolidin-1-yl)butanoate (Intermediate 14, major isomer) (30 mg, 0.061 mmol) in THF (3 mL) was added a solution of LiOH (48.5 mg, 2.03 mmol) in water (2.0 mL) and the reaction mixture was stirred at room temperature for 16 h. The solvent was removed under reduced pressure and the residue was blended with a previous batch (31 mg) and purified by preparative HPLC on an Xbridge C18 column (150 mm×19 mm) eluting with a gradient of MeCN-10 mM ammonium bicarbonate solution to give the title compound (26 mg, 83%) as a pale yellow gum: MS ES+ve m/z 482 (M+H)$^+$; $^1$H NMR (DMSO-d$_6$, 400 MHz) includes δ 7.18 (1H, t, J=8 Hz), 7.02 (1H, d, J=7 Hz), 6.82-6.74 (3H, m), 6.28-6.23 (2H, m), 3.94-3.85 (2H, m), 3.68-3.60 (2H, m), 3.31 (3H, s), 3.26-3.11 (4H, m), 2.91-2.66 (5H, m), 2.60 (2H, t, J 6 Hz), 2.44-2.30 (4H, m), 2.09-1.85 (2H, m), 1.78-1.55 (4H, m), 1.40-1.30 (1H, m), 1.17 (3H, d, J=6 Hz). Analytical chiral SFC on a Chiralpak AD-H column (250 mm×4.6 mm) RT=3.30 min, 99.4%, CO$_2$, 40% co-solvent (0.5% diethylamine in methanol), 4 g/min, 100 Bar, 29.9° C., detecting at 324 nm.

Example 4

(S)-3-(3-(2-methoxy-2-methylpropoxy)phenyl)-4-((R)-3-(2-(5,6,7,8-tetrahydro-1,8-naphthyridin-2-yl)ethyl)pyrrolidin-1-yl)butanoic acid

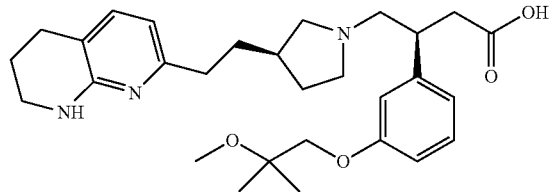 [SMILES: COC(C)(C)COc1cccc([C@H](CC(=O)O)CN2CC[C@@H](CCc3ccc4c(n3)NCCC4)C2)c1]

A mixture of methyl 3-(3-(2-methoxy-2-methylpropoxy)phenyl)-4-((R)-3-(2-(5,6,7,8-tetrahydro-1,8-naphthyridin-2-yl)ethyl)pyrrolidin-1-yl)butanoate (Intermediate 18) (150 mg, 0.294 mmol) and lithium hydroxide monohydride (35.2 mg, 1.47 mmol) in THF (0.3 mL), MeOH (0.2 mL) and water (0.1 mL) was stirred at room temperature for 18 h. The solvents were removed in vacuo and the residue was diluted with water (3 mL) and adjusted to pH 2 with 1N HCl. The water was removed in vacuo below 50° C. and the residue was purified by preparative HPLC on an Xbridge column (150 mm×3.0 mm) eluting with 20% increasing to 50% MeCN-aqueous 5 mM ammonium bicarbonate over 10 min. Appropriate fractions were combined and evaporated in vacuo to give the product (35 mg, 24%) as a pale brown solid: MS ES+ve m/z 496 (M+H)$^+$; $^1$H NMR (DMSO-d$_6$, 400 MHz) includes δ 7.16 (1H, t, J=8 Hz), 7.01 (1H, d, J=7.5 Hz), 6.81-6.73 (3H, m), 6.26-6.21 (2H, m), 3.80 (2H, s), 3.25-3.20 (2H, m), 3.19-3.12 (1H, m), 3.16 (3H, s), 2.84-2.62 (3H, m), 2.59 (2H, t, J=6 Hz), 2.39 (2H, t, J 8 Hz), 2.35-2.22 (2H, m), 2.05-1.96 (1H, m), 1.93-1.82 (1H, m), 1.78-1.70 (2H, m), 1.65-1.54 (2H, m), 1.37-1.28 (1H, m), 1.20 (6H, s). Analytical chiral SFC on a Chiralpak AS-H column (250 mm×4.6 mm) RT=1.83 min, 98%, CO$_2$, 40% co-solvent (0.5% diethylamine in methanol), 3 g/min, 100 Bar, 29.8° C., detecting at 324 nm.

Example 5

3-(3-(((S)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid

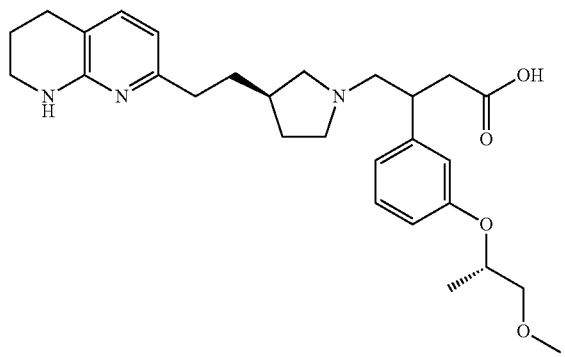 [SMILES: COC[C@H](C)Oc1cccc(C(CC(=O)O)CN2CC[C@@H](CCc3ccc4c(n3)NCCC4)C2)c1]

To a stirred solution of methyl 3-(3-(((S)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoate (Intermediate 22) (112 mg, 0.226 mmol) in THF (9 mL) was added LiOH (5.41 mg, 0.226 mmol) dissolved in water (3 mL) and the mixture was stirred at room temperature for 12 h. The reaction mixture was concentrated under reduced pressure. The residue (150 mg) was combined with 50 mg obtained from another reaction and purified by preparative HPLC on a Kromasil column (250 mm×25 mm) eluting with a gradient of MeCN—aq. ammonium bicarbonate to give 25 mg of a diastereoisomeric mixture (1:1). The mixture was separated by preparative chiral SFC on Chiralcel OD-H column (250 mm×21 mm) CO$_2$, 40% co-solvent (0.5% diethylamine in MeOH), 70 g/min, 100 Bar, 30.2° C., detecting at 324 nm to give the two diastereoisomers of the title compound:

Isomer 1 (17 mg, 15%): MS ES+ve m/z 482 (M+H)$^+$; Analytical chiral SFC RT=6.47 min, 98.8% on (R, R) Whelk-01 column (250 mm×4.6 mm) CO$_2$, 50% co-solvent (0.5% diethylamine in MeOH), 4 g/min, 100 Bar, 29.8° C., detecting at 323 nm; $^1$H NMR (DMSO-d$_6$, 400 MHz) includes δ 7.18 (1H, t, J=8 Hz), 7.04 (1H, d, J=7 Hz), 6.84-6.75 (3H, m), 6.26 (1H, d, J=7 Hz), 4.63-4.55 (1H, m), 3.48 (1H, dd, J 10.5, 6 Hz), 3.42 (1H, dd, J 10.5, 4 Hz), 2.60 (2H, t, J=6 Hz), 2.42 (2H, t, J=7.5 Hz), 1.78-1.71 (2H, m), 1.66-1.58 (2H, m), 1.20 (3H, d, J=6Hz)

Isomer 2 (10.4 mg, 9%): MS ES+ve m/z 482 (M+H)$^+$; Analytical chiral SFC RT=7.48 min, 96% on (R, R) Whelk-01 column (250 mm×4.6 mm) CO$_2$, 50% co-solvent (0.5% diethylamine in MeOH), 4 g/min, 100 Bar, 30.1° C., detecting at 323 nm.

Example 6

(S)-4-((R)-3-(2-(5,6,7,8-tetrahydro-1,8-naphthyridin-2-yl)ethyl)pyrrolidin-1-yl)-3-(3-(((S)-tetrahydrofuran-3-yl)oxy)phenyl)butanoic acid

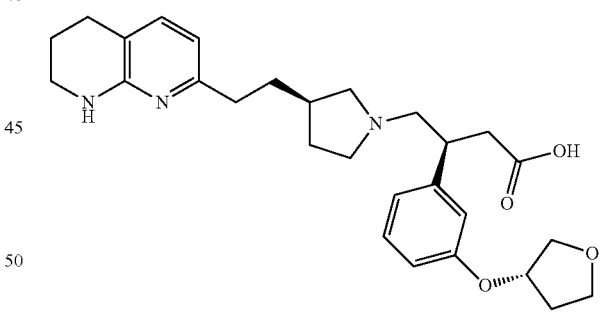

A solution of lithium hydroxide (48.5 mg, 2.03 mmol) was added dropwise to a solution of methyl 4-((R)-3-(2-(5,6,7,8-tetrahydro-1,8-naphthyridin-2-yl)ethyl)pyrrolidin-1-yl)-3-(3-(((S)-tetrahydrofuran-3-yl)oxy)phenyl)butanoate (Intermediate 25) (200 mg, 0.41 mmol) and the mixture was stirred for 16 h at room temperature. The solvent was removed in vacuo and the residue was purified by preparative HPLC on a Kinetex column (150 mm×30 mm) using a gradient of 70-100% 10 mM aqueous ammonium bicarbonate MeCN to give the product (180 mg) as a diastereoisomeric mixture (87:12) by analytical chiral SFC. The diastereoisomers were separated by preparative chiral SFC on a Chiralpak AD-H column (250 mm×21 mm) CO$_2$, 50% co-solvent (0.5% diethylamine in MeOH), 70 g/min, 100 Bar, detecting at 320 nm. The fractions were concentrated in vacuo and the residue was dissolved in MeOH (5 mL) and applied to a SCX cartridge washing with MeOH (2CV) and then eluting with 2M ammonia in MeOH to give the title compound (36 mg, 20%) as a pale brown solid: LCMS (System B) RT=0.83 min, 93%, ES+ve m/z 480 (M+H)$^+$; $^1$H NMR (DMSO-d$_6$, 400 MHz) δ 7.19 (1H, t, J 7.8 Hz), 7.02 (1H, d, J 7 Hz), 6.84-6.71 (3H, m), 6.30 (2H, m), 5.00 (1H, m), 3.93-3.71 (5H, m), 3.29-3.11 (4H, m), 2.89-2.66 (5H, m), 2.64-2.57 (2H, m), 2.45-2.16 (5H, m), 2.05-1.85 (3H, m), 1.80-1.70 (2H, m), 1.68-1.55 (2H, m), 1.41-1.30 (1H, m). Analytical chiral SFC on a Chiralpak AD-H column (250 mm×4.6 mm) RT=6.91 min, 97.5%, CO$_2$, 40% co-solvent (0.5% diethylamine in EtOH), 4 g/min, 100 Bar, 30.2° C., detecting at 320 nm.

Example 7

(S)-4-((R)-3-(2-(5,6,7,8-tetrahydro-1,8-naphthyridin-2-yl)ethyl)pyrrolidin-1-yl)-3-(3-(((R)-tetrahydrofuran-3-yl)oxy)phenyl)butanoic acid

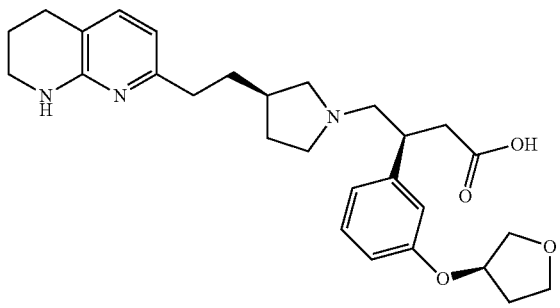 [SMILES: O=C(O)C[C@H](CN1CC[C@@H](CCc2ccc3c(n2)NCCC3)C1)c1cccc(O[C@@H]2CCOC2)c1]

A stirred solution of methyl 4-((R)-3-(2-(5,6,7,8-tetrahydro-1,8-naphthyridin-2-yl)ethyl)pyrrolidin-1-yl)-3-(3-(((R)-tetrahydrofuran-3-yl)oxy)phenyl)butanoate (Intermediate 28) (250 mg, 0.506 mmol) in THF (10 mL) and water (10 mL) was treated with LiOH (60.6 mg, 2.53 mmol) at 0° C. and the resulting mixture was stirred at 25° C. for 24 h. The solvents were removed in vacuo and the residue was purified by preparative HPLC on a Sunfire column (150 mm×19 mm) using a gradient of 10-40% MeCN —10 mM aqueous ammonium bicarbonate to give the product (150 mg) as a diastereoisomeric mixture. The diastereoisomers were separated by preparative chiral SFC on a Chiralpak AD-H column (250 mm×21 mm) CO$_2$, 50% co-solvent (0.5% isopropylamine in isopropanol), 75 g/min, 100 Bar, detecting at 319 nm. The fractions were concentrated in vacuo to give the title compound (130 mg, 83%) as a pale yellow foam: MS ES+ve m/z 480 (M+H)$^+$; $^1$H NMR (CDCl$_3$+D$_2$O, 400 MHz) δ 7.21 (1H, br t, J=7.8 Hz), 7.12 (1H, br d, J 7.5 Hz), 6.80 (1H, br d, J=7.8 Hz), 6.74-6.68 (2H, m), 6.28 (1H, d, J=7.5 Hz), 4.94-4.89 (1H, m), 4.74-4.65 (3H, m), 4.03-3.87 (4H, m), 3.47-3.38 (3H, m+t), 3.02-2.93 (2H, m), 2.78-2.67 (5H, m), 2.52-2.40 (2H, m), 2.27-1.98 (4H, m), 1.94-1.81 (3H, m), 1.62-1.52 (1H, m), 1.48-1.38 (1H, m). Analytical chiral SFC on a Chiralpak AS-H column (250 mm×4.6 mm) RT=3.45 min, 98.9%, CO$_2$, 50% co-solvent (0.5% isopropylamine in isopropanol), 4 g/min, 100 Bar, 29.9° C., detecting at 319 nm.

Example 8

(S)-3-(3,5-Bis(2-methoxyethoxy)phenyl)-4-((R)-3-(2-(5,6,7,8-tetrahydro-1,8-naphthyridin-2-yl)ethyl)pyrrolidin-1-yl)butanoic acid

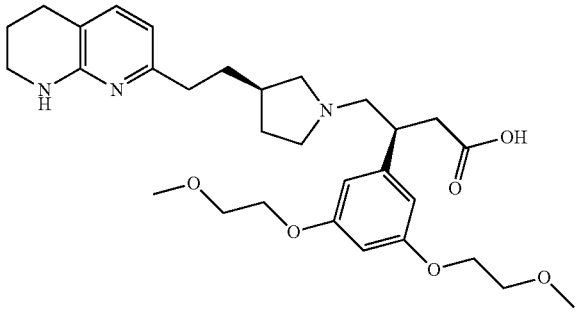 [SMILES: COCCOc1cc(OCCOC)cc([C@H](CC(=O)O)CN2CC[C@@H](CCc3ccc4c(n3)NCCC4)C2)c1]

A solution of methyl 3-(3,5-bis(2-methoxyethoxy)phenyl)-4-((R)-3-(2-(5,6,7,8-tetrahydro-1,8-naphthyridin-2-yl)ethyl)pyrrolidin-1-yl)butanoate (Intermediate 31) (110 mg, 0.198 mmol) in THF (0.6 mL), MeOH (0.4 mL) and water (0.2 mL) was treated with lithium hydroxide (14.22 mg, 0.594 mmol). The reaction mixture was stirred at room temperature for 18 h. The reaction mixture was concentrated under reduced pressure and the residue was neutralised with 1N HCl solution. The mixture was concentrated under reduced pressure and the residue (150 mg) was purified by preparative HPLC on an XTerra C18 column (250 mm×19 mm) eluting with a gradient of 10-60% MeCN in 5 mM aq. ammonium bicarbonate. The fractions were lyophilised in a freeze-drier overnight to give the title compound (60 mg, 54%) as a brown gum: MS ES+ve m/z 542 (M+H)$^+$; $^1$H NMR (DMSO-d$_6$, 400 MHz) includes δ 7.01 (1H, d, J=7.5 Hz), 6.40-6.36 (2H, m), 6.34 (1H, m), 6.26-6.22 (2H, m), 4.07-4.00 (4H, m), 3.65-3.60 (4H, m), 3.30 (6H, s), 3.25-3.20 (2H, m), 3.14-3.06 (1H, m), 2.89-2.65 (3H, m), 2.59 (2H, t, J=6 Hz), 2.42-2.27 (3H, m), 2.07-1.98 (1H, m), 1.95-1.85 (1H, m), 1.78-1.71 (2H, m), 1.65-1.55 (2H, m). Analytical chiral SFC on a Chiralpak AS-H column (250 mm×4.6 mm) RT=3.13 min, 83% and RT=4.47 min, 15%, CO$_2$, 40% co-solvent (0.5% diethylamine in MeOH), 4 g/min, 100 Bar, 29.9° C., detecting at 325 nm.

Example 9

(3S)-4-((R)-3-(2-(5,6,7,8-Tetrahydro-1,8-naphthyridin-2-yl)ethyl)pyrrolidin-1-yl)-3-(3-(tetrahydrofuran-3-yl)phenyl)butanoic acid Isomer 1

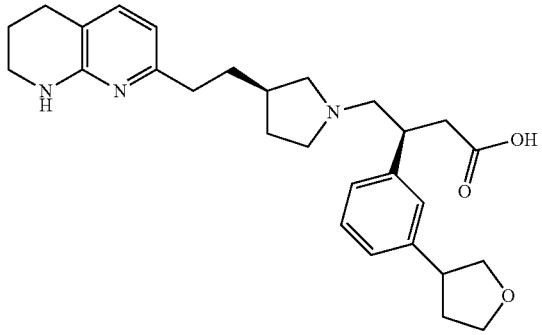 [SMILES: O=C(O)C[C@H](CN1CC[C@@H](CCc2ccc3c(n2)NCCC3)C1)c1cccc(C2CCOC2)c1]

2M NaOH in MeOH solution (209 μL, 0.419 mmol) was added to (3S)-methyl 4-((R)-3-(2-(5,6,7,8-tetrahydro-1,8- naphthyridin-2-yl)ethyl)pyrrolidin-1-yl)-3-(3-(tetrahydrofuran-3-yl)phenyl)butanoate (Intermediate 33, Isomer 1) (100 mg, 0.209 mmol) in DCM (1 mL). The mixture was left to stand at room temperature for 3 days and then the solvents were removed. The residue was dissolved in DMSO (1 mL) and purified by MDAP on an Xbridge column (100 mm×30 mm i.d. 5 μm packing diameter) using a gradient of MeCN in aqueous 10 mM ammonium bicarbonate solution. The solvent was removed under a stream of nitrogen in the Radleys blow-down apparatus to give the title compound (63 mg, 65%) as a white solid: LCMS (System B) RT=0.84 min, 100%, ES+ve m/z 464 (M+H)$^+$; $^1$H NMR (600 MHz, DMSO-d$_6$): δ 7.19-7.24 (m, 1H), 7.13 (s, 1H), 7.10 (d, J=7.5 Hz, 1H), 7.07 (d, J=7.5 Hz, 1H), 7.02 (d, J=7.0 Hz, 1H), 6.23-6.27 (m, 2H), 4.01 (t, J=8.0Hz, 1H), 3.93 (td, J=8.0, 4.5 Hz, 1H), 3.78 (q, J=8.0 Hz, 1H), 3.52 (t, J=8.0 Hz, 2H), 3.33 (quin, J=8.0 Hz, 1H), 3.21-3.25 (m, 2H), 3.14-3.20 (m, 1H), 2.86 (dd, J=12.0, 10.0 Hz, 1H), 2.74-2.81 (m, 2H), 2.67-2.73 (m, 1H), 2.60 (t, J=6.0 Hz, 2H), 2.56 (td, J=9.0, 5.5 Hz, 1H), 2.47-2.49 (m, 1H), 2.35-2.43 (m, 3H), 2.33 (dd, J=9.3, 7.2 Hz, 1H), 2.28 (dtd, J=12.0, 7.8, 4.5 Hz, 1H), 1.98-2.07 (m, 1H), 1.86-1.94 (m, 2H), 1.74 (quin, J=6.0 Hz, 2H), 1.54-1.67 (m, 2H), 1.30-1.39 (m, 1H).

Example 10

(3S)-4-((R)-3-(2-(5,6,7,8-Tetrahydro-1,8-naphthyridin-2-yl)ethyl)pyrrolidin-1-yl)-3-(3-(tetrahydrofuran-3-yl)phenyl)butanoic acid Isomer 2

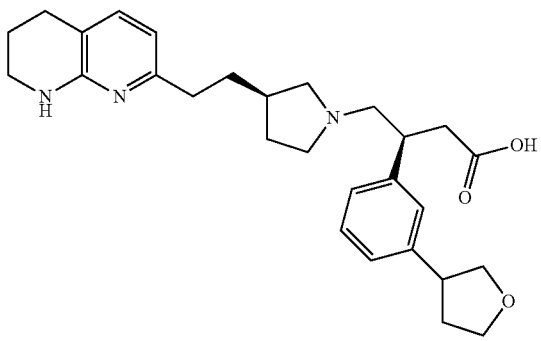 [SMILES: O=C(O)C[C@H](CN1CC[C@@H](CCc2ccc3c(n2)NCCC3)C1)c1cccc(C2CCOC2)c1]

2M NaOH in MeOH solution (138 μL, 0.276 mmol) was added to (3S)-methyl 4-((R)-3-(2-(5,6,7,8-tetrahydro-1,8-naphthyridin-2-yl)ethyl)pyrrolidin-1-yl)-3-(3-(tetrahydrofuran-3-yl)phenyl)butanoate (Intermediate 33, Isomer 2) (66 mg, 0.138 mmol) in DCM (0.69 mL). The mixture was left to stand at room temperature for 3 days and then the solvents were removed. The residue was dissolved in DMSO (1 mL) and purified by MDAP on an Xbridge column (100 mm×30 mm i.d. 5 μm packing diameter) using a gradient of MeCN in aqueous 10 mM ammonium bicarbonate solution. The solvent was removed under a stream of nitrogen in the Radleys blow-down apparatus to give the title compound (40 mg, 62%) as a white solid: LCMS (System B) RT=0.84 min, 100%, ES+ve m/z 464 (M+H)$^+$; $^1$H NMR (600 MHz, DMSO-d$_6$) δ 7.22 (t, J=7.5 Hz, 1H), 7.14 (s, 1H), 7.10 (br d, J=7.5 Hz, 1H), 7.07 (br d, J=7.5 Hz, 1H), 7.02 (br d, J=7.0 Hz, 1H), 6.20-6.30 (m, 2H), 3.99-4.04 (m, 1H), 3.90-3.96 (m, 1H), 3.75-3.82 (m, 1H), 3.52 (br t, J=8.0 Hz, 1H), 3.30-3.37 (m, 1H), 3.21-3.26 (m, 2H), 3.14-3.20 (m, 1H), 2.83-2.91 (m, 1H), 2.74-2.82 (m, 2H), 2.68-2.74 (m, 1H), 2.57-2.62 (m, 2H), 2.53-2.60 (m, 1H), 2.47-2.52 (m, 1H), 2.38-2.43 (m, 2H), 2.36-2.41 (m, 1H), 2.31-2.36 (m, 1H), 2.24-2.31 (m, 1H), 1.99-2.08 (m, 1H), 1.85-1.95 (m, 2H), 1.71-1.78 (m, 2H), 1.55-1.67 (m, 2H), 1.30-1.40 (m, 1H).

Example 11

(S)-3-(3-((1-methoxy-2-methylpropan-2-yl)oxy)phenyl)-4-((R)-3-(2-(5,6,7,8-tetrahydro-1,8-naphthyridin-2-yl)ethyl)pyrrolidin-1-yl)butanoic acid

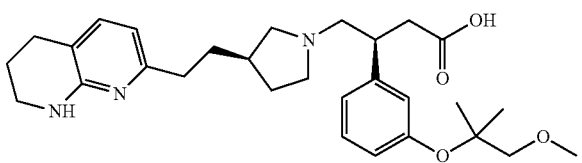 [SMILES: COCC(C)(C)Oc1cccc([C@H](CC(=O)O)CN2CC[C@@H](CCc3ccc4c(n3)NCCC4)C2)c1]

A stirred solution of (S)-methyl 3-(3-((1-methoxy-2-methylpropan-2-yl)oxy)phenyl)-4-((R)-3-(2-(5,6,7,8-tetrahydro-1,8-naphthyridin-2-yl)ethyl)pyrrolidin-1-yl)butanoate (Intermediate 38) (250 mg, 0.491 mmol) in THF (4 mL) was treated with a solution of LiOH (58.7 mg, 2.45 mmol) in water (1 mL) and the mixture was stirred for 18 h. The solvents were removed in vacuo and the residue was purified by HPLC on a Kinetex column (150 mm×30 mm) eluting with a gradient of 20-60% MeCN-aqueous 10 mM ammonium bicarbonate solution, flow-rate 30 mL/min. The fractions were concentrated in vacuo and the residue (80 mg), which was a diastereoisomeric mixture (86:11), was separated by chiral SFC on a Chiralpak AD-H column (250 mm×30 mm) eluting with 50% EtOH-hexane, flow-rate=42 mL/min, detecting at 248 nm. The fractions were evaporated in vacuo to give the title compound (16 mg, 6%) as a yellow oil: LCMS (System B) RT=0.93 min, 96%, ES+ve m/z 496 (M+H)$^+$; $^1$H NMR (CDCl$_3$, 400 MHz) includes δ 7.21 (1H, t, J 8 Hz), 7.13 (1H, d, J=7.5 Hz), 6.93 (1H, d, J=7.5 Hz), 6.90-6.84 (2H, m), 6.30 (1H, d, J=7 Hz), 3.45 (3H, s), 3.44-3.38 (2H, m), 2.98 (2H, t, J=11.5 Hz), 2.79-2.68 (4H, m), 2.56-2.42 (4H, m), 2.37-2.24 (1H, m), 2.21-2.11 (1H, m), 2.10-2.00 (1H, m), 1.96-1.85 (4H, m), 1.65-1.55 (1H, m), 1.50-1.40 (1H, m), 1.31 (6H, s). Analytical chiral SFC on a Chiralcel OD-H column (250 mm×4.6 mm) RT=3.76 min, 97.5%, CO$_2$, 40% co-solvent (0.5% diethylamine in MeOH), 4 g/min, 100 Bar, 30° C., detecting at 326 nm.

Example 12

(S)-3-(3-(((R)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid

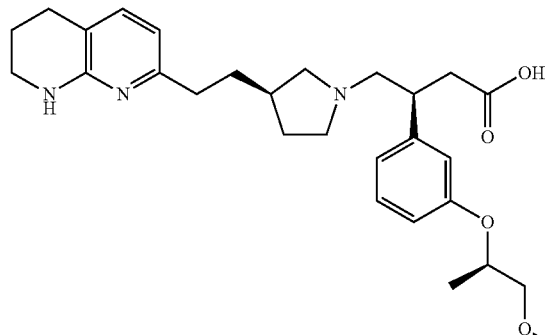

A solution of (S)-methyl 3-(3-(((R)-1-methoxpropan-2-yl)oxy)phenyl)-4-((R)-3-(2-(5,6,7,8-tetrahydro-1,8-naphthyridin-2-yl)ethyl)pyrrolidin-1-yl)butanoate (Intermediate 42) (400 mg, 0.81 mmol) in THF (15 mL) was treated with LiOH (38.7 mg, 1.61 mmol) dissolved in water (10 mL) and the reaction mixture was stirred at room temperature for 12 h. The reaction mixture was concentrated under reduced pressure and the residue (500 mg). The mixture was purified by HPLC on a Kromasil C18 column (250 mm×25 mm) eluting with a gradient of 10-60% MeCN in 10 mM aqueous ammonium bicarbonate, flow-rate=16 mL/min, at ambient temperature. The fractions were concentrated to give 200 mg of the product as a diastereoisomeric mixture in the ratio of 81:18. The mixture was separated by preparative chiral SFC on a (R, R)-Whelk column (250 mm×30 mm) $CO_2$, 50% co-solvent (0.5% isopropylamine in MeOH), 120 g/min, 100 Bar, detecting at 325 nm. The fractions were concentrated to give 50 mg of the major diastereoisomer MS ES+ve m/z 482 (M+H)$^+$. The compound was then further purified by HPLC on an XBridge C18 column (150 mm×19 mm) eluting with a gradient of 10-60% MeCN in 10 mM aqueous ammonium bicarbonate, flow-rate=16 mL/min, at ambient temperature. The fractions were evaporated under reduced pressure to give the title compound (36.4 mg, 9%) as a yellow gum: MS ES+ve m/z 482 (M+H)$^+$; $^1$H NMR (DMSO-$d_6$, 400 MHz) includes δ 7.16 (1H, t, J=7.5 Hz), 7.01 (1H, d, J=7.5 Hz), 6.81-6.73 (3H, m), 6.27-6.23 (2H, m), 4.62-4.54 (1H, m), 3.48 (1H, dd, J=10.5, 6 Hz), 3.42 (1H, dd, J=10.5, 4 Hz), 2.88-2.66 (5H, m), 2.60 (2H, t, J=6 Hz), 2.40 (2H, t, J=7.5 Hz), 1.78-1.70 (2H, m), 1.68-1.54 (2H, m), 1.19 (3H, d, J 6Hz). Analytical chiral SFC on (R, R) Whelk column (250 mm×4.6 mm) RT=5.16 min, 98.6%, $CO_2$, 50% co-solvent (0.5% diethylamine in MeOH), 4 g/min, 100 Bar, 29.8° C., detecting at 324 nm.

Example 13

(S)-3-(3-(2-Isopropoxyethoxy)phenyl)-4-((R)-3-(2-(5,6,7,8-tetrahydro-1,8-naphthyridin-2-yl)ethyl)pyrrolidin-1-yl)butanoic acid

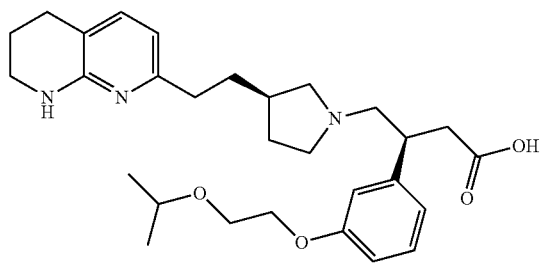 [SMILES: CC(C)OCCOc1cccc([C@H](CC(=O)O)CN2CC[C@@H](CCc3ccc4c(n3)NCCC4)C2)c1]

A stirred solution of methyl 3-(3-(2-isopropoxyethoxy)phenyl)-4-((R)-3-(2-(5,6,7,8-tetrahydro-1,8-naphthyridin-2-yl)ethyl)pyrrolidin-1-yl)butanoate (Intermediate 45) (44 mg, 0.086 mmol) in MeOH (3 mL), THF (2 mL) and water (1 mL) was treated with LiOH (6.20 mg, 0.259 mmol) and the mixture was stirred at room temperature for 16 h. After completion of the reaction, the mixture was concentrated under reduced pressure. The residue was neutralised with 1N HCl solution and the solvents removed under reduced pressure. The residue (100 mg) was purified by preparative HPLC on an XTerra C18 column (250 mm×19 mm) eluting with a gradient of 20-60% MeCN in 5 mM aq. ammonium bicarbonate, flow-rate=20 mL/min, at ambient temperature. The fractions were lyophilised in a freeze-drier overnight to afford the title compound (21.5 mg, 49%): MS ES+ve m/z 496 (M+H)$^+$; $^1$H NMR (DMSO-$d_6$, 400 MHz) includes δ 7.17 (1H, t, J=8 Hz), 7.01 (1H, d, J=7 Hz), 6.80 (1H, s), 6.79-6.73 (2H, m), 6.26-6.22 (2H, m), 4.03 (2H, m), 3.67 (2H, m), 3.25-3.20 (1H, m), 2.89-2.66 (4H, m), 2.60 (2H, t, J 6 Hz), 1.77-1.70 (2H, m), 1.66-1.55 (2H, m), 1.39-1.30 (1H, m), 1.11 (6H, d, J 6 Hz). Analytical chiral SFC on a Chiralcel OD-H column (250 mm×4.6 mm) RT=4.87 min, 87.3%, $CO_2$, 40% co-solvent (0.5% diethylamine in MeOH), 5 g/min, 100 Bar, 29.8° C., detecting at 324 nm.

Example 14

(S)-4-((R)-3-(2-(5,6,7,8-Tetrahydro-1,8-naphthyridin-2-yl)ethyl)pyrrolidin-1-yl)-3-(3-(((R)-tetrahydrofuran-2-yl)methoxy)phenyl)butanoic acid

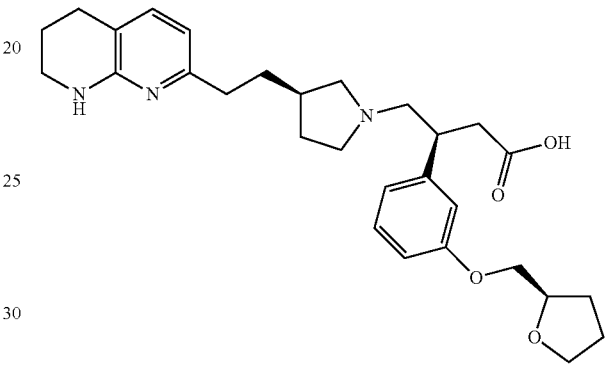

A stirred solution of methyl 4-((R)-3-(2-(5,6,7,8-tetrahydro-1,8-naphthyridin-2-yl)ethyl)pyrrolidin-1-yl)-3-(3-(((R)-tetrahydrofuran-2-yl)methoxy)phenyl)butanoate (Intermediate 48) (220 mg, 0.433 mmol) in THF (5 mL) was added lithium hydroxide (51.9 mg, 2.17 mmol) in water (1.25 mL) and the reaction mixture was stirred at 25° C. for 12 h. The reaction mixture was concentrated under reduced pressure. The residue was purified by HPLC on an Xbridge C18 column (150 mm×19 mm) eluting with a gradient of 10-60% MeCN in 10 mM aq. ammonium bicarbonate, flow-rate=18 mL/min, at ambient temperature. The fractions were evaporated in vacuo to give a diastereomeric mixture of the product (31:68). The diastereoisomers (108 mg) were separated by preparative chiral SFC on a Chiralcel OJ-H column (250 mm×30 mm) eluting with $CO_2$, 20% co-solvent (30 mM ammonia in MeOH), 60 g/min, 100 Bar, 30° C., detecting at 323 nm to give:
the major isomer (S)-4-((R)-3-(2-(5,6,7,8-tetrahydro-1,8-naphthyridin-2-yl)ethyl)pyrrolidin-1-yl)-3-(3-(((R)-tetrahydrofuran-2-yl)methoxy)phenyl)butanoic acid: (53 mg, 26%): MS ES+ve m/z 494 (M+H)$^+$; $^1$H NMR (DMSO-$d_6$, 400 MHz) includes δ 7.10 (1H, t, J=7.5 Hz), 7.00 (1H, d, J=7.5 Hz), 6.75-6.70 (2H, m), 6.66 (1H, d, J=7.5 Hz), 6.26-6.20 (2H, m), 4.17-4.10 (1H, m), 3.90-3.83 (2H, m), 3.80-3.74 (1H, m), 3.70-3.65 (1H, m), 3.25-3.12 (3H, m), 2.72 (1H, m), 2.65-2.53 (4H, m), 2.48-2.30 (5H, m), 2.10-1.52 (10H, m), 1.30-1.20 (1H, m). Analytical chiral SFC on a Chiralcel OJ-H column (250 mm×4.6 mm) RT=4.05 min, 95.5%, CO2, 25% co-solvent (30 mM ammonia in MeOH), 3 g/min, 100 Bar, 30° C., detecting at 323 nm, and
the minor isomer: (R)-4-((R)-3-(2-(5,6,7,8-tetrahydro-1,8-naphthyridin-2-yl)ethyl)pyrrolidin-1-yl)-3-(3-(((R)-tetrahydrofuran-2-yl)methoxy)phenyl)butanoic acid (22 mg, 11%) was also isolated: MS ES+ve m/z 494 (M+H)$^+$; $^1$H NMR

Example 15

(S)-4-((R)-3-(2-(5,6,7,8-tetrahydro-1,8-naphthyridin-2-yl)ethyl)pyrrolidin-1-yl)-3-(3-(((S)-tetra hydrofuran-2-yl)methoxy)phenyl)butanoic acid

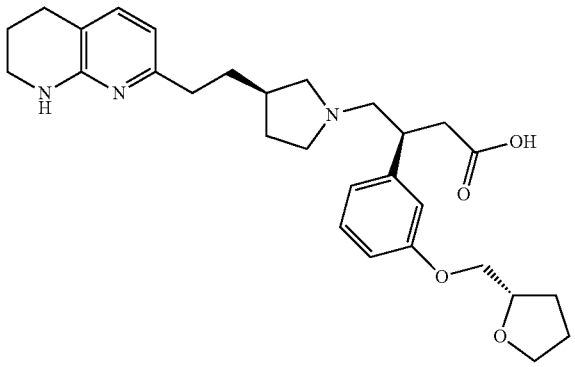 [SMILES: O=C(O)C[C@H](CN1CC[C@@H](CCc2ccc3c(n2)NCCC3)C1)c1cccc(OC[C@@H]2CCCO2)c1]

A stirred solution of (S)-methyl 4-((R)-3-(2-(5,6,7,8-tetrahydro-1,8-naphthyridin-2-yl)ethyl)pyrrolidin-1-yl)-3-(3-(((S)-tetrahydrofuran-2-yl)methoxy)phenyl)butanoate (Intermediate 51) (250 mg, 0.492 mmol) in THF (7 mL) and MeOH (2 mL) was treated with a solution of lithium hydroxide monohydrate (59 mg, 2.46 mmol) in water (1 mL) and the resulting mixture was stirred at 25° C. for 18 h. The solvents were removed in vacuo, the residue was partitioned between water (4 mL) and diethyl ether (5 mL), the aqueous layer was washed with ether (2×5 mL), separated and concentrated in vacuo. The residue (250 mg) was purified by reverse-phase preparative HPLC on an Xbridge C18 column (150 mm×19 mm) eluting with a gradient of 10-65% MeCN in 10 mM aq. ammonium bicarbonate, flow-rate=18 mL/min, at ambient temperature. The fractions were evaporated in vacuo to give the product (100 mg) as a diastereomeric mixture (90.6:9). The diastereoisomers were separated by preparative chiral SFC on a Chiralcel OJ-H column (250 mm×30 mm) eluting with CO2, 20% co-solvent (30 mM ammonia in MeOH), 60 g/min, 100 Bar, 30° C., detecting at 323 nm to give:
the major isomer (S)-4-((R)-3-(2-(5,6,7,8-tetrahydro-1,8-naphthyridin-2-yl)ethyl)pyrrolidin-1-yl)-3-(3-(((S)-tetrahydrofuran-2-yl)methoxy)phenyl)butanoic acid (63 mg, 26%) as an off-white solid: MS ES+ve m/z 494 (M+H)+. Analytical chiral SFC on a Chiralcel OJ-H column (250 mm×4.6 mm) RT=4.90 min, 99.0%, CO2, 25% co-solvent (30 mM ammonia in MeOH), 60 g/min, 100 Bar, 29.8° C., detecting at 323 nm and
the minor isomer: (R)-4-((R)-3-(2-(5,6,7,8-tetrahydro-1,8-naphthyridin-2-yl)ethyl)pyrrolidin-1-yl)-3-(3-(((S)-tetrahydrofuran-2-yl)methoxy)phenyl)butanoic acid (6 mg, 2%) MS ES+ve m/z 494 (M+H)+.

(DMSO-d6, 400 MHz) includes δ 7.16 (1H, t, J=7.5 Hz), 7.00 (1H, d, J=7.5 Hz), 6.80-6.72 (3H, m), 6.26-6.20 (2H, m), 4.16-4.10 (1H, m), 3.94-3.85 (2H, m), 3.81-3.75 (1H, m), 3.70-3.64 (1H, m), 2.87-2.50 (8H, m), 2.42-2.29 (3H, m), 2.19-2.14 (1H, m), 2.04-1.56 (10H, m), 1.36-1.28 (1H, m). Analytical chiral SFC on a Chiralcel OJ-H column (250 mm×4.6 mm) RT=2.98 min, 97.7%, CO2, 25% co-solvent (30 mM ammonia in MeOH), 3 g/min, 100 Bar, 29.8° C., detecting at 323 nm.

Example 16

(S)-3-(2-Fluoro-5-(2-methoxyethoxy)phenyl)-4-((R)-3-(2-(5,6,7,8-tetrahydro-1,8-naphthyridin-2-yl)ethyl)pyrrolidin-1-yl)butanoic acid

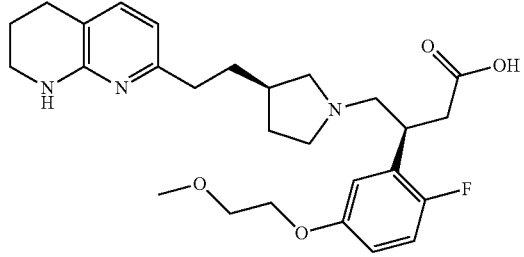 [SMILES: COCCOc1ccc(F)c([C@H](CC(=O)O)CN2CC[C@@H](CCc3ccc4c(n3)NCCC4)C2)c1]

A mixture of methyl 3-((S)-2-fluoro-5-(2-methoxyethoxy)phenyl)-4-((R)-3-(2-(5,6,7,8-tetrahydro-1,8-naphthyridin-2-yl)ethyl)pyrrolidin-1-yl)butanoate (prepared by similar procedures to those described above for Intermediate 10) (70.6 mg, 0.141 mmol) and an aqueous solution of NaOH (2M, 0.353 mL, 0.707 mmol) in MeOH (5 mL) was sealed and heated in a Biotage Initator microwave oven for 2 h at 80° C. The solvent was removed in vacuo, and the residue was purified by reverse-phase column chromatography eluting with 25-50% MeCN (containing 0.1% ammonia) in 10 mM ammonium bicarbonate, 8 CV). The appropriate fractions were combined and evaporated in vacuo to afford the title compound (14 mg, 20%): LCMS (System C) RT=0.53 min, 100%, ES+ve m/z 486 (M+H)+; 1NMR (DMSO-d6, 600 MHz) includes δ 7.03-6.97 (2H, m), 6.86-6.83 (1H, m), 6.76-6.72 (1H, m), 6.26 (1H, br s), 6.24 (1H, d, J 7.5 Hz), 4.04 (2H, m), 3.63 (2H, m), 3.49-3.43 (2H, m), 3.30 (3H, s), 3.23 (2H, m), 2.73 (1H, t, J=8 Hz), 2.65 (1H, dd, J=12, 8 Hz), 2.44-2.32 (3H, m), 2.13 (1H, t, J=8 Hz), 2.01-1.94 (1H, m), 1.89-1.81 (1H, m), 1.77-1.72 (2H, m), 1.63-1.53 (2H, m), 1.33-1.26 (1H, m).

Example 17

3-(3-((1,3-Dimethoxypropan-2-yl)oxy)phenyl)-4-((R)-3-(2-(5,6,7,8-tetrahydro-1,8-naphthyridin-2-yl)ethyl)pyrrolidin-1-yl)butanoic acid

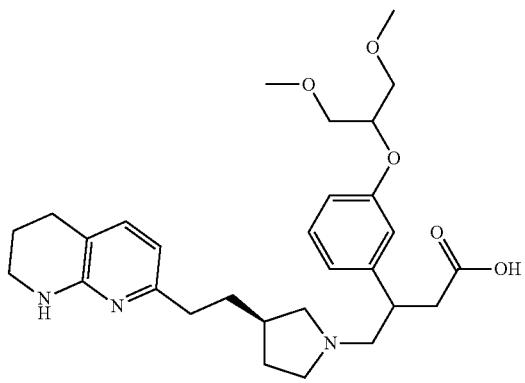 [SMILES: COCC(COC)Oc1cccc(C(CC(=O)O)CN2CC[C@@H](CCc3ccc4c(n3)NCCC4)C2)c1]

The title compound was prepared by a similar procedure to that described for Example 2 from the corresponding methyl ester (Intermediate 52). Obtained (55 mg, 56%): LCMS (System B) RT=0.87 min, 100%, ES+ve m/z 512 (M+H)+; Analytical chiral SFC on a Chiralcel OD-H column (250 mm×4.6 mm) RT=4.06 min, 58.3% and RT=4.98 min, 38.6% , $CO_2$, 40% co-solvent (0.5% diethylamine in MeOH), 5 g/min, 100 Bar, 29.8° C., detecting at 324 nm.

Example 18

3-(3-(2-Fluoroethoxy)-5-(2-methoxyethoxy)phenyl)-4-((R)-3-(2-(5,6,7,8-tetrahydro-1,8-naphthyridin-2-yl)ethyl)pyrrolidin-1-yl)butanoic acid

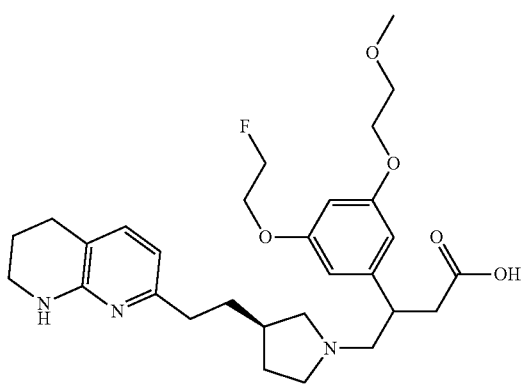 [SMILES: COCCOc1cc(OCCF)cc(C(CC(=O)O)CN2CC[C@@H](CCc3ccc4c(n3)NCCC4)C2)c1]

The title compound was prepared by a similar procedure to that described for Example 2 from the corresponding methyl ester (Intermediate 53). Obtained (30 mg, 25%): MS ES+ve m/z 530 (M+H)+. Analytical chiral SFC on a Chiralpak AD-H column (250 mm×4.6 mm) RT=2.89 min, 63.9% and RT=3.88 min, 35.4% , $CO_2$, 40% co-solvent (0.5% diethylamine in MeOH), 4 g/min, 100 Bar, 30° C., detecting at 324 nm.

Example 19

3-(3-(3-Methoxypropoxy)phenyl)-4-((R)-3-(2-(5,6,7,8-tetrahydro-1,8-naphthyridin-2-yl)ethyl)pyrrolidin-1-yl)butanoic acid

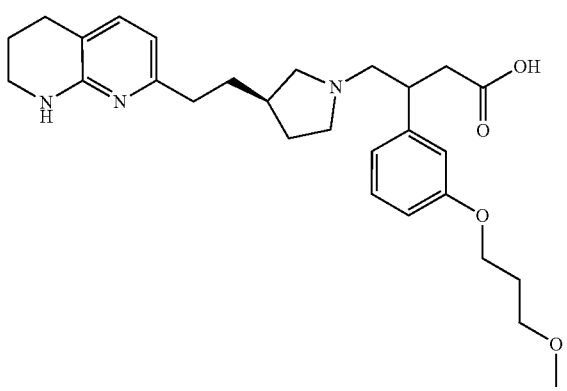 [SMILES: COCCCOc1cccc(C(CC(=O)O)CN2CC[C@@H](CCc3ccc4c(n3)NCCC4)C2)c1]

The title compound was prepared by a similar procedure to that described for Example 2 from the corresponding methyl ester (Intermediate 54). Obtained (20 mg, 11%): MS ES+ve m/z 482 (M+H)+. Analytical chiral SFC on a Chiralcel OD-H column (250 mm×4.6 mm) RT=2.30 min, 16.1% and RT=2.89 min, 81.7% , $CO_2$, 25% co-solvent (0.5% diethylamine in MeOH), 3 g/min, 100 Bar, 30° C., detecting at 321 nm.

Example 20

3-(3-(Oxetan-3-ylmethoxy)phenyl)-4-((R)-3-(2-(5,6,7,8-tetrahydro-1,8-naphthyridin-2-yl)ethyl)pyrrolidin-1-yl)butanoic acid

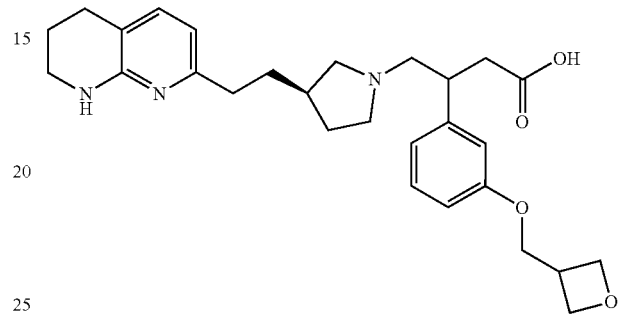

The title compound was prepared by a similar procedure to that described for Example 2 from the corresponding methyl ester (Intermediate 55). Obtained (41 mg, 42%): MS ES+ve m/z 480 (M+H)+. Analytical chiral SFC on a Chiralcel OD-H column (250 mm×4.6 mm) RT=3.53 min, 69.0% and RT=4.56 min, 29.3% , $CO_2$, 50% co-solvent (0.5% diethylamine in MeOH), 4 g/min, 100 Bar, 30° C., detecting at 323 nm.

Example 21

(S)-3-(3-(Oxetan-3-yloxy)phenyl)-4-((R)-3-(2-(5,6,7,8-tetrahydro-1,8-naphthyridin-2-yl)ethyl)pyrrolidin-1-yl)butanoic acid

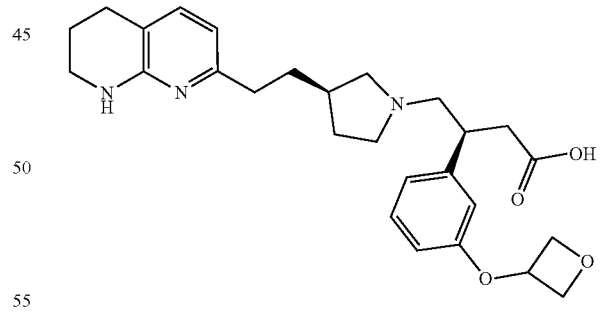

To (S)-methyl 3-(3-(oxetan-3-yloxy)phenyl)-4-((R)-3-(2-(5,6,7,8-tetrahydro-1,8-naphthyridin-2-yl)ethyl)pyrrolidin-1-yl)butanoate (Intermediate 61) (400 mg, 0.834 mmol) in THF (4 mL), MeOH (1.714 mL) & water (0.571 mL) was added LiOH monohydrate (175 mg, 4.17 mmol) and the reaction mixture was stirred at room temperature for 20 h. The solvent was evaporated in vacuo to afford the crude material which was purified by reverse-phase column chromatograhy using a 40 g column eluting with 40-50% MeCN and water. The appropriate fractions were combined to give an off-white solid which was subjected to preparative chiral HPLC purification on a Chiralcel AD-H column (250mm× 21mm), eluting with 50% (15mM methanolic ammonia in EtOH), flow-rate=50.0 g/min, detecting at 215 nm, the relevant fraction was collected and concentrated in vacuo to afford the title compound (150 mg, 38%) as a white solid; MS ES+ve m/z 466 (M+H)$^+$; $^1$H NMR (400MHz, DMSO-d$_6$) includes δ 7.19 (t, J8 Hz, 1H), 7.01 (d, J=7.5 Hz, 1H), 6.84 (d, J=8 Hz, 1H), 6.67 (m, 1H), 6.57 (dd, J=8, 2 Hz, 1H), 6.27-6.22 (m, 2H), 5.25 (quint, J=6 Hz, 1H), 4.91 t, J 7 Hz, 2H), 4.54-4.49 (m, 2H), 3.26-3.11 (m, 3H), 2.86-2.64 (m, 4H), 2.60 (t, J 6 Hz, 2H), 2.57-2.45 (m, obscured by DMSO), 2.43-2.26 (m, 4H), 2.07-1.97 (m, 1H), 1.95-1.84 (m, 1H), 1.78-1.71 (m, 2H), 1.65-1.55 (m, 2H), 1.39-1.29 (m, 1H); Analytical chiral HPLC RT=7.46 min, 99%, CO$_2$, 50% co-solvent on a (R,R)Whelk-01 column (250mm×4.6 mm), eluting with 30 mM methanolic ammonia in MeOH, 4.0 g/min, 100 Bar, at 23° C., detecting at 303 nm.

Example 22

(S)-4-((R)-3-(2-(5,6,7,8-Tetrahydro-1,8-naphthyridin-2-yl)ethyl)pyrrolidin-1-yl)-3-(3-((tetrahydro-2H-pyran-4-yl)oxy)phenyl)butanoic acid

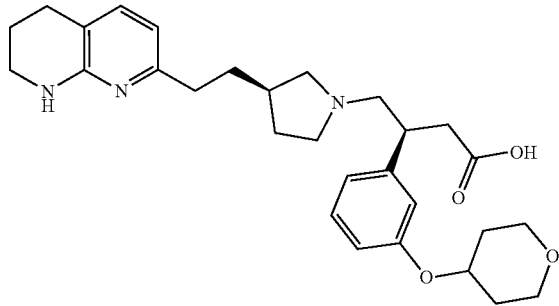 [SMILES: O=C(O)C[C@H](CN1CC[C@@H](CCc2ccc3c(n2)NCCC3)C1)c1cccc(OC2CCOCC2)c1]

To tert-butyl (S)-4-((R)-3-(2-(5,6,7,8-tetrahydro-1,8-naphthyridin-2-yl)ethyl)pyrrolidin-1-yl)-3-(3-((tetrahydro-2H-pyran-4-yl)oxy)phenyl)butanoate (Intermediate 64) (190.9 mg, 0.347 mmol) was added 2-methylTHF (2 mL) and conc. HCl (0.145 mL, 1.736 mmol) and the mixture was stirred rapidly at 40° C. for 18 h. The reaction mixture was diluted with water and the phases were separated. The organic phase was washed with water, and the aqueous phases were combined. 2N NaOH was added to the combined aqueous phases to pH 7.5 and this solution was extracted with DCM. The organic phase was then washed with brine, dried (MgSO$_4$) and evaporated in vacuo. The residue was subjected to preparative HPLC purification on a Xselect CSH C18 column (150mm×30mm), eluting with 15 to 99% MeCN in 10 mM ammonium bicarbonate solution over 15 min, flow rate=18 mL/min,. The required fractions were combined and evaporated in vacuo to give the title compound (66 mg, 39%) as an off-white foam; LCMS (System B) RT =0.85 min, 100%, ES+ve m/z 494 (M+H)$^+$; $^1$H NMR (CDCl$_3$) δ 7.24-7.16 (2H, m), 6.80-6.74 (3H, m), 6.30 (1H, d, J=7Hz), 4.51-4.44 (1H, m), 4.02-3.95 (2H, m), 3.62-3.54 (2H, m), 3.50-3.34 (3H, m), 3.15-3.05 (1H, m), 3.02-2.93 (1H, m), 2.79-2.67 (6H, m), 2.56-2.46 (1H, m), 2.28-2.16 (1H, m), 2.16-2.06 (1H, m), 2.06-1.97 (2H, m), 1.96-1.73 (6H, m), 1.71-1.60 (1H, m), 1.58-1.47 (1H, m).

Biological Assays
Cell Adhesion Assays

Reagents and methods utilised are as described [Ludbrook et al, Biochem. J. 2003, 369, 311 and Macdonald et al. ACS Med. Chem. Lett. 2014, 5, 1207-1212 for α$_v$β$_8$ assay), with the following points of clarification. The following cell lines are used, with ligands in brackets: K562-α$_v$β$_3$ (LAP-b$_1$), K562-α$_v$β$_5$ (Vitronectin), K562-α$_v$β$_6$ (LAP-b$_1$), K562-α$_v$β$_8$ (LAP-b$_1$), A549-α$_v$β$_1$ (LAP-b$_1$). The divalent cation used to facilitate adhesion is 2 mM MgCl$_2$. Adhesion is quantified by cell labelling with the fluorescent dye BCECF-AM (Life Technologies), where cell suspensions at 3×10$^6$cells/nnL are incubated with 0.33 uL/mL of 30 mM BCECF-AM at 37° C. for 10 minutes, then 50 μL/well are dispensed into the 96-well assay plate. At the assay conclusion cells that adhered are lysed using 50 μL/well of 0.5% Triton X-100 in H$_2$O to release fluorescence. Fluorescence intensity is detected using an Envision® plate reader (Perkin Elmer). For active antagonists in the assay, data is fitted to a 4 parameter logistic equation for IC$_{50}$ determinations.

All of the exemplified compounds were generally tested according to the above assays and were found to be α$_v$ β$_6$ integrin antagonists. Those of skill in the art will recognise that in vitro binding assays and cell-based assays for functional activity are subject to experimental variability. Accordingly, it is to be understood that the values given below are exemplary only and that repeating the assay run(s) may result in somewhat different pIC$_{50}$ values.

The mean affinities (pIC$_{50}$) of Example 1 in the Cell Adhesion Assays were, for α$_v$β$_6$ pIC$_{50}$=8.5; α$_v$β$_1$ pIC$_{50}$=6.8; α$_v$β$_3$ pIC$_{50}$=6.6; α$_v$β$_5$ pIC$_{50}$=8.0; α$_v$β$_8$ pIC$_{50}$=7.9.

The mean affinities (pIC$_{50}$) of Example 2 in the cell Adhesion Assays were, for α$_v$β$_6$ pIC$_{50}$=8.6; α$_v$β$_1$ pIC$_{50}$=7.0; α$_v$β$_3$ pIC$_{50}$=7.2; α$_v$β$_5$ pIC$_{50}$=7.8; α$_v$β$_8$ pIC$_{50}$=7.9.

The mean affinities (pIC$_{50}$) of Example 3 in the cell Adhesion Assays were, for α$_v$β$_6$ pIC$_{50}$=8.6; α$_v$β$_1$ pIC$_{50}$=6.9; α$_v$β$_3$ pIC$_{50}$=6.9; α$_v$β$_5$ pIC$_{50}$=7.8; α$_v$β$_8$ pIC$_{50}$=7.8.

The mean affinities (pIC$_{50}$) of Example 4 in the cell Adhesion Assays were, for α$_v$β$_6$ pIC$_{50}$=8.5; α$_v$β$_1$ pIC$_{50}$=6.8; α$_v$β$_3$ pIC$_{50}$=6.7; β$_v$β$_5$ pIC$_{50}$=7.7; α$_v$β$_8$ pIC$_{50}$=7.8.

The mean affinities (pIC$_{50}$) of Example 5 in the cell Adhesion Assays were, for α$_v$β$_6$ pIC$_{50}$=8.1; α$_v$β$_1$ pIC$_{50}$=6.6; α$_v$β$_3$ pIC$_{50}$=5.5; α$_v$β$_5$ pIC$_{50}$=ND (not determined); α$_v$β$_8$ pIC$_{50}$=ND.

The mean affinities (pIC$_{50}$) of Example 6 in the cell Adhesion Assays were, for α$_v$β$_6$ pIC$_{50}$=8.8; α$_v$β$_1$ pIC$_{50}$=7.3; α$_v$β$_3$ pIC$_{50}$=6.8; α$_v$β$_5$ pIC$_{50}$=7.7; α$_v$β$_8$ pIC$_{50}$=8.2.

The mean affinities (pIC$_{50}$) of Example 7 in the cell Adhesion Assays were, for α$_v$β$_6$ pIC$_{50}$=8.6; α$_v$β$_1$ pIC$_{50}$=6.9; α$_v$β$_3$ pIC$_{50}$=6.6; α$_v$β$_5$ pIC$_{50}$=7.6; α$_v$β$_8$ pIC$_{50}$=8.0.

The mean affinities (pIC$_{50}$) of Example 8 in the cell Adhesion Assays were, for α$_v$β$_6$ pIC$_{50}$=8.5; α$_v$β$_1$ pIC$_{50}$=6.7; α$_v$β$_3$ pIC$_{50}$=6.9; α$_v$β$_5$ pIC$_{50}$=7.5; α$_v$β$_8$ pIC$_{50}$=7.7.

The mean affinities (pIC$_{50}$) of Example 9 in the cell Adhesion Assays were, for α$_v$β$_6$ pIC$_{50}$=8.7; α$_v$β$_1$ pIC$_{50}$=7.2; α$_v$β$_3$ pIC$_{50}$=6.7; α$_v$β$_5$ pIC$_{50}$=7.4; α$_v$β$_8$ pIC$_{50}$=8.1.

The mean affinities (pIC$_{50}$) of Example 10 in the cell Adhesion Assays were, for α$_v$β$_6$ pIC$_{50}$=8.7; α$_v$β$_1$ pIC$_{50}$=7.2; α$_v$β$_3$ pIC$_{50}$=6.6; α$_v$β$_5$ pIC$_{50}$=7.3; α$_v$β$_8$ pIC$_{50}$=8.0.

The mean affinities (pIC$_{50}$) of Example 11 in the cell Adhesion Assays were, for α$_v$β$_6$ pIC$_{50}$=8.4; α$_v$β$_1$ pIC$_{50}$=7.3; α$_v$β$_3$ pIC$_{50}$=6.5; α$_v$β$_5$ pIC$_{50}$=7.2; α$_v$β$_8$ pIC$_{50}$=7.8.

The mean affinities (pIC$_{50}$) of Example 12 in the cell Adhesion Assays were, for α$_v$β$_6$ pIC$_{50}$=8.6; α$_v$β$_1$ pIC$_{50}$=7.1; α$_v$β$_3$ pIC$_{50}$=6.6; α$_v$β$_5$ pIC$_{50}$=7.2; α$_v$β$_8$ pIC$_{50}$=7.8.

The mean affinities (pIC$_{50}$) of Example 13 in the cell Adhesion Assays were, for α$_v$β$_6$ pIC$_{50}$=8.0; α$_v$β$_1$ pIC$_{50}$=ND; α$_v$β$_3$ pIC$_{50}$=7.0; α$_v$β$_5$ pIC$_{50}$=7.5; α$_v$β$_8$ pIC$_{50}$=7.7.

The mean affinities (pIC$_{50}$) of Example 14 in the cell Adhesion Assays were, for α$_v$β$_6$ pIC$_{50}$=8.3; α$_v$β$_1$pIC$_{50}$=6.4; α$_v$β$_3$ pIC$_{50}$=7.1; α$_v$β$_5$ pIC$_{50}$=7.4; α$_v$β$_8$ pIC$_{50}$=7.7.

The mean affinities (pIC$_{50}$) of Example 15 in the cell Adhesion Assays were, for α$_v$β$_6$ pIC$_{50}$=8.3; α$_v$β$_1$ pIC$_{50}$=6.3; α$_v$β$_3$ pIC$_{50}$=7.0; α$_v$β$_5$ pIC$_{50}$=7.4; α$_v$β$_8$ pIC$_{50}$=7.4.

The mean affinities (pIC$_{50}$) of Example 16 in the cell Adhesion Assays were, for α$_v$β$_6$ pIC$_{50}$=8.1; α$_v$β$_1$ pIC$_{50}$=ND; α$_v$β$_3$ pIC$_{50}$=6.5; α$_v$β$_5$ pIC$_{50}$=7.9; α$_v$β$_8$ pIC$_{50}$=7.0.

The mean affinities (pIC$_{50}$) of Example 17 in the cell Adhesion Assays were, for α$_v$β$_6$ pIC$_{50}$=7.9; α$_v$β$_1$ pIC$_{50}$=ND; α$_v$β$_3$ pIC$_{50}$=6.4; α$_v$β$_5$ pIC$_{50}$=ND; α$_v$β$_8$ pIC$_{50}$=7.7.

The mean affinities (pIC$_{50}$) of Example 18 in the cell Adhesion Assays were, for α$_v$β$_6$ pIC$_{50}$=8.3; α$_v$β$_1$ pIC$_{50}$=6.7; α$_v$β$_3$ pIC$_{50}$=6.4; α$_v$β$_5$ pIC$_{50}$=ND; α$_v$β$_8$ pIC$_{50}$=7.6.

The mean affinities (pIC$_{50}$) of Example 19 in the cell Adhesion Assays were, for α$_v$β$_6$ pIC$_{50}$=8.0; α$_v$β$_1$ pIC$_{50}$=ND; α$_v$β$_3$ pIC$_{50}$=6.8; α$_v$β$_5$ pIC$_{50}$=7.2; α$_v$β$_8$ pIC$_{50}$=7.9.

The mean affinities (pIC$_{50}$) of Example 20 in the cell Adhesion Assays were, for α$_v$β$_6$ pIC$_{50}$=8.1; α$_v$β$_1$ pIC$_{50}$=ND; α$_v$β$_3$ pIC$_{50}$=6.4; α$_v$β$_5$ pIC$_{50}$=ND; α$_v$β$_8$ pIC$_{50}$=7.7.

The mean affinities (pIC$_{50}$) of Example 21 in the cell Adhesion Assays were, for α$_v$β$_6$ pIC$_{50}$=8.9; α$_v$β$_1$ pIC$_{50}$=6.9; α$_v$β$_3$ pIC$_{50}$=6.8; α$_v$β$_5$ pIC$_{50}$=8.3; α$_v$β$_8$ pIC$_{50}$=ND.

The mean affinities (pIC$_{50}$) of Example 22 in the cell Adhesion Assays were, for α$_v$β$_6$ pIC$_{50}$=8.7; α$_v$β$_1$ pIC$_{50}$=7.0; α$_v$β$_3$ pIC$_{50}$=6.8; α$_v$β$_5$ pIC$_{50}$=ND; α$_v$β$_8$ pIC$_{50}$=ND.

The invention claimed is:

1. A compound of Formula (I) or a pharmaceutically acceptable salt thereof:

wherein:
R$_1$ and R$_2$ are each independently hydrogen or —O—CR$_5$R$_6$—CR$_7$R$_8$—O(C$_{1-3}$-alkyl),
wherein R$_1$ and R$_2$ are not both hydrogen;
or R$_2$ is hydrogen and R$_1$ is
(i) a group selected from or
(ii) a group selected from or
(iii) a group selected from or R$_2$ is hydrogen and R$_1$ is or R$_2$ is hydrogen and R$_1$ is —O(CH$_2$)$_3$OMe;
or one of R$_1$ and R$_2$ is —O(CH$_2$)$_2$OMe and the other is —O(CH$_2$)$_2$F;
R$_3$ is hydrogen or fluoro,
wherein R$_3$ is hydrogen when R$_1$ and R$_2$ are not hydrogen; and
R$_5$, R$_6$, R$_7$ and R$_8$ are each independently hydrogen or methyl;
or one of R$_5$ or R$_6$ is —CH$_2$OMe.

2. The compound or pharmaceutically acceptable salt thereof according to claim 1,
wherein:
R$_1$ and R$_2$ are each independently hydrogen or —O—CR$_5$R$_6$—CR$_7$R$_8$—O(C$_{1-3}$-alkyl),
wherein R$_1$ and R$_2$ are not both hydrogen;
or R$_2$ is hydrogen and R$_1$ is
(i) a group selected from or (ii) a group selected from

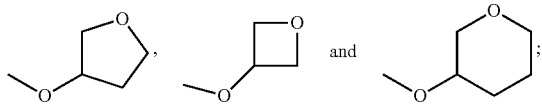

or (iii) a group selected from

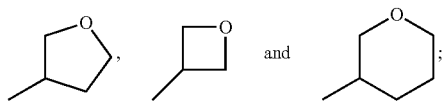

or $R_2$ is hydrogen and $R_1$ is

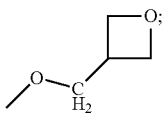

or $R_2$ is hydrogen and $R_1$ is —O(CH$_2$)$_3$OMe;
or one of $R_1$ and $R_2$ is —O(CH$_2$)$_2$OMe and the other is —O(CH$_2$)$_2$F;
$R_3$ is hydrogen or fluoro,
wherein $R_3$ is hydrogen when $R_1$ and $R_2$ are not hydrogen; and
$R_5$, $R_6$, $R_7$ and $R_8$ are each independently hydrogen or methyl;
or one of $R_5$ or $R_6$ is —CH$_2$OMe.

3. The compound or pharmaceutically acceptable salt thereof according to claim 1, wherein one of R1 and R2 is hydrogen and the other is —O—CR5R6—CR7R8—O(C1-3-alkyl), and R5, R6, R7 and R8 are each independently hydrogen or methyl.

4. The compound or pharmaceutically acceptable salt thereof according to claim 1, wherein one of R1 and R2 is hydrogen and the other is selected from 2-methoxyethoxy, 2-methoxypropoxy, 2-methoxy-2-methylpropoxy, (1-methoxypropan-2-yl)oxy, (1-methoxy-2-methylpropan-2-yl)oxy, and 2-isopropoxyethoxy group.

5. The compound or pharmaceutically acceptable salt thereof according to claim 4, wherein one of R1 and R2 is hydrogen and the other is selected from 2-methoxypropoxy and (1-methoxy-2-methylpropan-2-yl)oxy.

6. The compound or pharmaceutically acceptable salt thereof according to claim 1, wherein R1 and R2 are —O—CR5R6—CR7R8—O(C1-3-alkyl), and R5, R6, R7 and R8 are each independently hydrogen or methyl.

7. The compound or pharmaceutically acceptable salt thereof according to claim 6, wherein R1 and R2 are 2-methoxyethoxy.

8. The compound or pharmaceutically acceptable salt thereof according to claim 1, wherein R2 is hydrogen and R1 is (tetrahydrofuran-2-yl)methoxy.

9. The compound or pharmaceutically acceptable salt thereof according to claim 1, wherein R2 is hydrogen and R1 is (tetrahydrofuran-3-yl)oxy.

10. The compound or pharmaceutically acceptable salt thereof according to claim 1, wherein R2 is hydrogen and R1 is tetrahydrofuran-3-yl.

11. The compound or pharmaceutically acceptable salt thereof according to claim 1, wherein R2 is hydrogen and R1 is (oxetan-3-yl)oxy.

12. The compound or pharmaceutically acceptable salt thereof according to claim 1, wherein R2 is hydrogen and R1 is (tetrahydropyran-4-yl)-oxy.

13. The compound or pharmaceutically acceptable salt thereof according to claim 1, wherein R3 is hydrogen.

14. The compound or pharmaceutically acceptable salt thereof according to claim 1, wherein R3 is fluoro.

15. The compound or pharmaceutically acceptable salt thereof according to claim 14, wherein R2 is hydrogen.

16. The compound according to claim 1 which is: (S)-3-(3-(2-methoxyethoxy)phenyl)-4-((R)-3-(2-(5,6,7,8-tetrahydro-1,8-naphthyridin-2-yl)ethyl)pyrrolidin-1 -yl)butanoic acid;
(S)-3-(3-((R)-2-methoxypropoxy)phenyl)-4-((R)-3-(2-(5, 6,7,8-tetrahydro-1,8-naphthyridin-2-yl)ethyl)pyrrolidin-1-yl)butanoic acid;
(S)-3-(3-((S)-2-methoxypropoxy)phenyl)-4-((R)-3-(2-(5, 6,7,8-tetrahydro-1,8-naphthyridin-2-yl)ethyl)pyrrolidin-1-yl)butanoic acid;
(S)-3-(3-(2-methoxy-2-methylpropoxy)phenyl)-4((R)-3-(2-(5,6,7,8-tetrahydro-1,8-naphthyridin-2-yl)ethyl)pyrrolidin-1-yl)butanoic acid;
3-(3-(((S)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid;
(S)-4-((R)-3-(2-(5,6,7,8-tetrahydro-1,8-naphthyridin-2-yl)ethyl)pyrrolidin-1 -yl)-3-(3-(((S)-tetrahydrofuran-3-yl)oxy)phenyl)butanoic acid;
(S)-4-((R)-3-(2-(5,6,7,8-tetrahydro-1,8-naphthyridin-2-yl)ethyl)pyrrolidin-1 -yl)-3-(3-(((R)-tetrahydrofuran-3-yl)oxy)phenyl)butanoic acid;
(S)-3-(3,5-Bis(2-methoxyethoxy)phenyl)-4-((R)-3-(2-(5, 6,7,8-tetrahydro-1,8-naphthyridin-2-yl)ethyl)pyrrolidin-1-yl)butanoic acid;
(3S)-4-((R)-3-(2-(5,6,7,8-Tetrahydro-1,8-naphthridin-2-yl)ethyl)pyrrolidin-1 -yl)-3-(3 -(tetrahydrofuran-3-yl) phenyl)butanoic acid;
(3S)-4-((R)-3-(2-(5,6,7,8-Tetrahydro-1,8-naphthridin-2-yl)ethyl)pyrrolidin-1-yl)-3-(3 -(tetrahydrofuran-3-yl) phenyl)butanoic acid;
(S)-3-(3-(((1-methoxy-2-methylpropan-2-yl)oxy)phenyl)-4-((R)-3-(2-(5,6,7,8-tetrahydro-1,8-naphthyridin-2-yl) ethyl)pyrrolidin-1-yl)butanoic acid;
(S)-3-(3-(((R)-1-methoxypropan-2-yl)oxy)phenyl)-4-((R)-3-(2-(5,6,7,8-tetrahydro-1,8-naphthyridin-2-yl) ethyl)pyrrolidin-1-yl)butanoic acid;
(S)-3-(3-(2-Isopropoxyethoxy)phenyl)-4-((R)-3-(2-(5,6, 7,8-tetrahydro-1,8-naphthyridin-2-yl)ethyl)pyrrolidin-1-yl)butanoic acid;
(S)-4-((R)-3-(2-(5,6,7,8-Tetrahydro-1,8-naphthyridin-2-yl) ethyl)pyrrolidin-1 -yl)-3-(3-(((R)-tetrahydrofuran-2-yl)methoxy)phenyl)butanoic acid;
(S)-4-((R)-3-(2-(5,6,7,8-tetrahydro-1,8-naphthyridin-2-yl)ethyl)pyrrolidin-1 -yl)-3-(3-(((S)-tetrahydrofuran-2-yl)methoxy)phenyl)butanoic acid;
(S)-3-(2-Fluoro-5-(2-methoxyethoxy)phenyl)-4-((R)-3-(2-(5,6,7,8-tetrahydro-1,8-naphthyridin-2-yl)ethyl)pyrolidin-1-yl)butanoic acid;
3-(3-((1,3-Dimethoxypropan-2-yl)oxy)phenyl)-4-((R)-3-(2-(5,6,7,8-tetrahydro-1,8-naphthyridin-2-yl)ethyl)pyrrolidin-1-yl)butanoic acid;
3-(3-(2-Fluoroethoxy)-5-(2-methoxyethoxy)phenyl)-4-((R)-3-(2-(5,6,7,8-tetrahydro-1,8-naphthyridin-2-yl) ethyl)pyrrolidin-1-yl)butanoic acid;

3-(3-(3-Methoxypropoxy)phenyl)-4-((R)-3-(2-(5,6,7,8-tetrahydro-1,8-naphthridin-2-yl)ethyl)pyrrolidin-1-yl)butanoic acid; or 3-(3-(Oxetan-3-ylmethoxy)phenyl)-4-((R)-3-(2-(5,6,7,8-tetrahydro-1,8-naphthyridin-2-yl)ethyl)pyrrolidin-1-yl)butanoic acid;

or a pharmaceutically acceptable salt thereof.

17. The compound according to claim 1 which is:

(S)-3-(3-(Oxetan-3-yloxy)phenyl)-4-((R)-3-(2-(5,6,7,8-tetrahydro-1,8-naphthyridin-2-yl)ethyl)pyrrolidin-1-yl)butanoic acid; or (S)-4-((R)-3-(2-(5,6,7,8-Tetrahydro-1,8-naphthyridin-2-yl)ethyl)pyrrolidin-1-yl)-3-(3-((tetrahydro-2H-pyran-4-yl)oxy)phenyl)butanoic acid;

or a pharmaceutically acceptable s alt thereof.

18. A pharmaceutical composition comprising the compound or pharmaceutically acceptable salt thereof according to claim 1 and a pharmaceutic ally acceptable carrier, diluent, or excipient.

19. A method of treating fibrosis in a human in need thereof comprising administering to the human a therapeutically effective amount of a compound or pharmaceutically acceptable salt thereof according to claim 1.

20. The method according to claim 19, wherein the fibrosis is pulmonary fibrosis.

21. The method according to claim 19, wherein the fibrosis is idiopathic pulmonary fibrosis.

22. The method according to claim 19, wherein the fibrosis is hepatic fibrosis.

23. The method according to claim 19, wherein the fibrosis is renal fibrosis.

* * * * *